(12) United States Patent
Schwartz

(10) Patent No.: US 12,661,172 B2
(45) Date of Patent: *Jun. 23, 2026

(54) INSTRUMENT FOR THERAPEUTICALLY CYTOTOXICALLY ABLATING PARATHYROIDAL TISSUE WITHIN A PARATHYROID GLAND

(71) Applicant: Alan N. Schwartz, Edmonds, WA (US)

(72) Inventor: Alan N. Schwartz, Edmonds, WA (US)

( * ) Notice: Subject to any disclaimer, the term of this patent is extended or adjusted under 35 U.S.C. 154(b) by 1035 days.

This patent is subject to a terminal disclaimer.

(21) Appl. No.: 17/849,451

(22) Filed: Jun. 24, 2022

(65) Prior Publication Data

US 2022/0361937 A1    Nov. 17, 2022

Related U.S. Application Data

(63) Continuation of application No. 16/153,632, filed on Oct. 5, 2018, now Pat. No. 11,406,438, which is a
(Continued)

(51) Int. Cl.
    *A61B 18/06*        (2006.01)
    *A61B 18/02*        (2006.01)
    (Continued)

(52) U.S. Cl.
    CPC .............. *A61B 18/06* (2013.01); *A61B 18/02* (2013.01); *A61B 18/1477* (2013.01);
    (Continued)

(58) Field of Classification Search
    CPC ..... A61B 18/06; A61B 18/02; A61B 18/1477; A61B 2017/00743; A61B 2018/00017; A61B 2018/00196; A61B 2018/0022; A61B 2018/00279; A61B 2018/00428; A61B 2018/00577; A61B 2018/00613;
    (Continued)

(56) References Cited

U.S. PATENT DOCUMENTS

2007/0021458 A1*    1/2007    Ishikawa ............ A61K 31/4743
                                                          604/20

* cited by examiner

*Primary Examiner* — Laura A Bouchelle
*Assistant Examiner* — Sarah Dympna Grasmeder
(74) *Attorney, Agent, or Firm* — Leonid Kisselev

(57)        ABSTRACT

One embodiment provides a tightly targeted minimally invasive therapy (TTMIT) parathyroid tissue ablating instrument. A substance that cytotoxically ablates parathyroidal tissue during application in the parathyroidal tissue of therapeutically sufficient units of an electromagnetic energy having a frequency only ranging from ultraviolet to visible to near infrared. A substance delivery device is configured to introduce the substance into the parathyroidal tissue. An electromagnetic energy treatment device is configured to apply the therapeutically sufficient units of the electromagnetic energy within a thermal range that is non-cytotoxic to the parathyroidal tissue to the substance after the substance has been introduced by the substance delivery device. A sensor is configured to monitor activation of the substance as the therapeutically sufficient units of the electromagnetic energy are applied. The electromagnetic energy treatment device is further configured to modulate applying the therapeutically sufficient units of the electromagnetic energy once the substance has been activated.

20 Claims, 24 Drawing Sheets

Related U.S. Application Data continuation of application No. 15/785,278, filed on Oct. 16, 2017, now abandoned, which is a continuation of application No. 14/639,991, filed on Mar. 5, 2015, now Pat. No. 9,820,798, which is a continuation of application No. 13/624,841, filed on Sep. 21, 2012, now abandoned.

(60) Provisional application No. 61/538,708, filed on Sep. 23, 2011.

(51) Int. Cl.

| | |
|---|---|
| *A61B 18/14* | (2006.01) |
| *A61M 5/00* | (2006.01) |
| *A61M 5/14* | (2006.01) |
| *A61M 5/168* | (2006.01) |
| *A61M 5/32* | (2006.01) |
| *A61N 1/00* | (2006.01) |
| *A61N 2/00* | (2006.01) |
| *A61N 5/00* | (2006.01) |
| *A61N 5/10* | (2006.01) |
| *A61B 17/00* | (2006.01) |
| *A61B 18/00* | (2006.01) |
| *A61B 18/04* | (2006.01) |
| *A61B 90/00* | (2016.01) |
| *A61M 25/00* | (2006.01) |
| *A61N 1/40* | (2006.01) |
| *A61N 5/06* | (2006.01) |
| *A61N 7/02* | (2006.01) |

(52) U.S. Cl.
CPC .......... *A61M 5/007* (2013.01); *A61M 5/1407* (2013.01); *A61M 5/168* (2013.01); *A61M 5/32* (2013.01); *A61N 1/00* (2013.01); *A61N 2/004* (2013.01); *A61N 5/00* (2013.01); *A61N 5/1027* (2013.01); *A61B 2017/00743* (2013.01); *A61B 2018/00017* (2013.01); *A61B 2018/00196* (2013.01); *A61B 2018/0022* (2013.01); *A61B 2018/00279* (2013.01); *A61B 2018/00428* (2013.01); *A61B 2018/00577* (2013.01); *A61B 2018/00613* (2013.01); *A61B 2018/00642* (2013.01); *A61B 2018/00702* (2013.01); *A61B 2018/00708* (2013.01); *A61B 2018/00791* (2013.01); *A61B 2018/00839* (2013.01); *A61B 2018/00863* (2013.01); *A61B 2018/00875* (2013.01); *A61B 2018/00994* (2013.01); *A61B 2018/0262* (2013.01); *A61B 2018/0293* (2013.01); *A61B 2018/044* (2013.01); *A61B 2018/1472* (2013.01); *A61B 2090/378* (2016.02); *A61B 2090/3908* (2016.02); *A61B 2090/3966* (2016.02); *A61B 2218/002* (2013.01); *A61M 2025/0046* (2013.01); *A61M 25/0068* (2013.01); *A61N 1/406* (2013.01); *A61N 5/062* (2013.01); *A61N 2005/0626* (2013.01); *A61N 2005/0635* (2013.01); *A61N 2005/0659* (2013.01); *A61N 2005/0661* (2013.01); *A61N 7/02* (2013.01); *A61N 2007/025* (2013.01)

(58) Field of Classification Search
CPC ........... A61B 2018/00642; A61B 2018/00702; A61B 2018/00708; A61B 2018/00791; A61B 2018/00839; A61B 2018/00863; A61B 2018/00875; A61B 2018/00994; A61B 2018/0262; A61B 2018/0293; A61B 2018/044; A61B 2018/1472; A61B 2090/378; A61B 2090/3908; A61B 2090/3966; A61B 2218/002; A61M 5/007; A61M 5/1407; A61M 5/168; A61M 5/32; A61M 25/0068; A61M 2025/0046; A61N 5/062; A61N 2005/0626; A61N 2005/0635; A61N 2005/0661; A61N 1/00; A61N 2/004; A61N 1/406; A61N 5/00; A61N 5/1027; A61N 7/02; A61N 2005/0659; A61N 2007/025

See application file for complete search history.

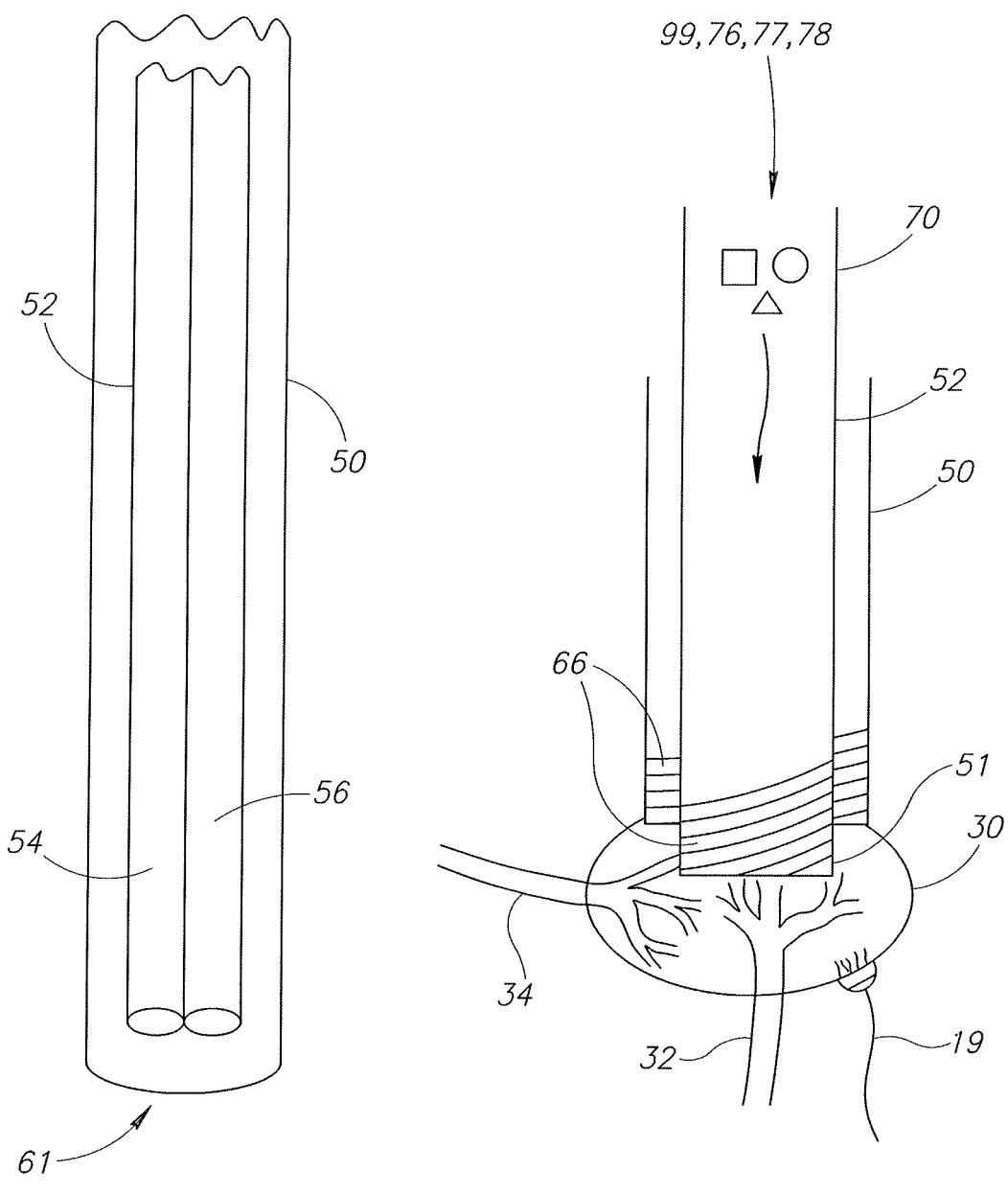
FIG.4                    FIG.5

*108*

0   30   40   50   60   70   80   100   °CELSIUS

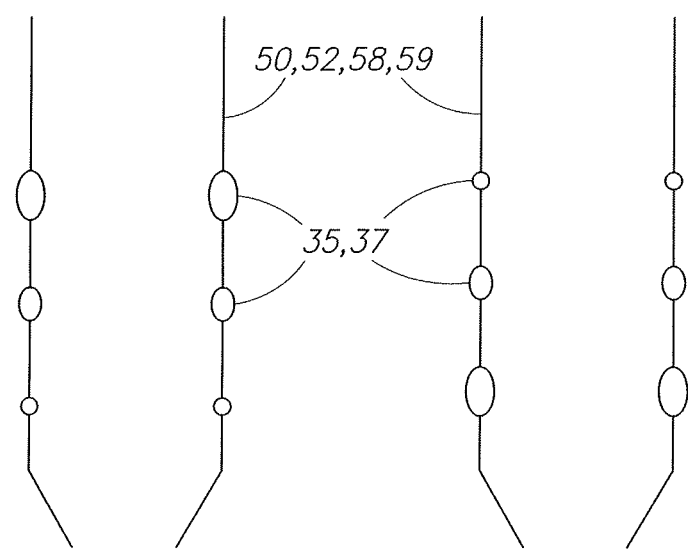
FIG.20
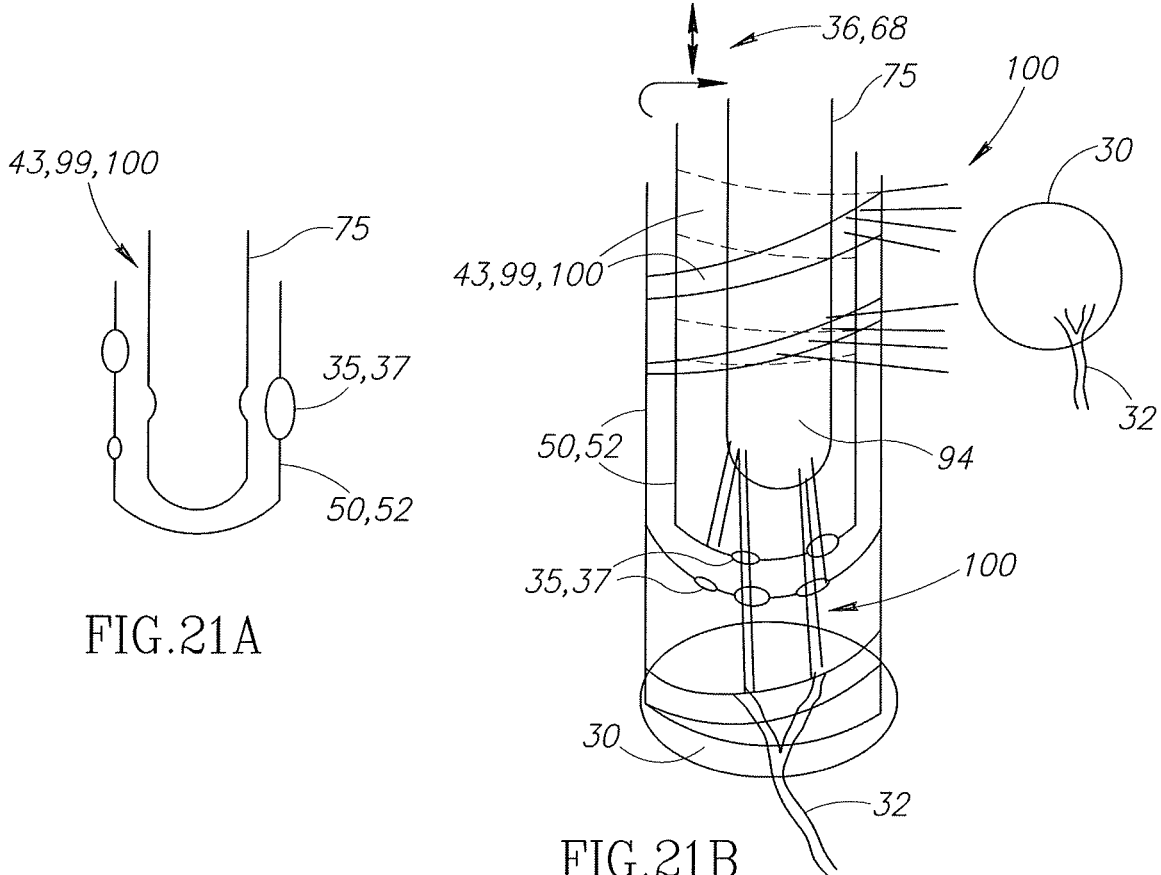
FIG.21A
FIG.21B

*50,52,58,57,70*

99

43

*50,52,58,57,70*

99

43

54

*50,52,58,57,70*

56

99

43

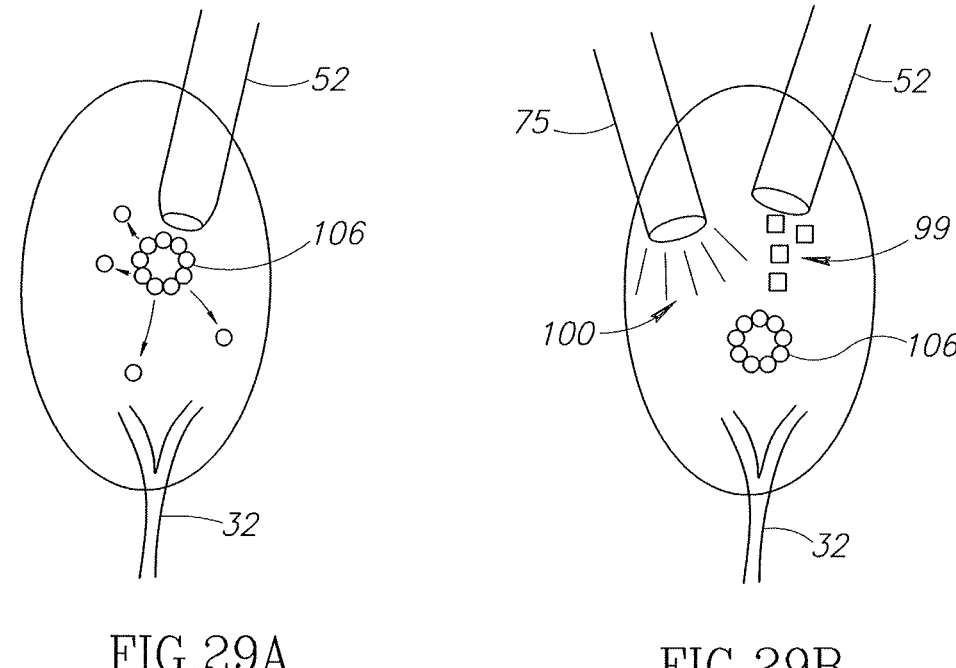
FIG.29A
FIG.29B
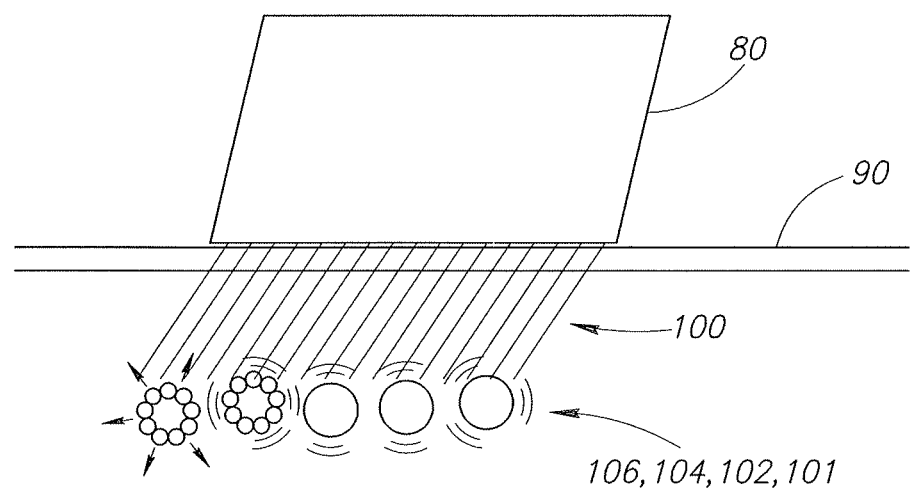
FIG.29C

INSTRUMENT FOR THERAPEUTICALLY CYTOTOXICALLY ABLATING PARATHYROIDAL TISSUE WITHIN A PARATHYROID GLAND

CROSS-REFERENCE TO RELATED APPLICATIONS

This patent application is a continuation of U.S. patent application Ser. No. 16/153,632, filed Oct. 5, 2018, pending, which is a continuation of U.S. patent application Ser. No. 15/785,278, filed Oct. 16, 2017, abandoned, which is a continuation of U.S. Pat. No. 9,820,798, issued Nov. 21, 2017, which is a continuation of U.S. patent application Ser. No. 13/624,841, filed Sep. 21, 2012, abandoned, which claims the benefit of U.S. Provisional Application No. 61/538,708 filed on Sep. 23, 2011, the disclosure of which are incorporated herein by reference in their entirety.

COPYRIGHT NOTICE

FIELD

The present invention relates generally to medical devices, methods and systems, and in particular for the treatment of parathyroid glands and parathyroid-based diseases, such as hyperparathyroidism, hypoparathyroidism and hypercalcemia.

BACKGROUND

In the human body there are four small parathyroid glands. Each gland typically weighs about thirty 30 to forty 40 mg and is located near the thyroid. The cells of the parathyroid glands release parathyroid hormone, which helps maintain serum and bone calcium homeostasis in the body. The two upper parathyroid glands are usually located adjacent to the posterior surface of the upper or middle part, of the thyroid lobe, just anterior to the recurrent laryngeal nerve as it enters the larynx. The two lower parathyroid glands are usually found on the lateral or posterior surfaces of the lower part of the thyroid gland or within several centimeters of the lower thyroid pole.

The thyroid gland generally receives innervations from both the sympathetic and parasympathetic divisions of the autonomic nervous system. The sympathetic fibers arise from the cervical ganglia and enter with blood vessels and the parasympathetic fibers arise from the vagus and reach the thyroid gland via branches of the laryngeal nerves. The parathyroid and thyroid glands relation to the recurrent laryngeal nerves and to the external branch of the superior laryngeal nerves is of major surgical significance because damage to these nerves can lead to a disability of phonation. Based on the close anatomic association of the thyroid and parathyroid glands, it is assumed that the parathyroids are innervated in a manner similar to that of the thyroid.

Disorders of the parathyroid gland include hyperparathyroidism, hypoparathyroidism, osteoporosis, as well as a myriad of other diseases. Primary hyperparathyroidism exists when a disorder of parathyroid tissue itself, or a "primary defect," results in the release of excessive amounts of Parathyroid hormone. Among the known causes of primary hyperparathyroidism, as well as examples of primary defects, are parathyroid adenoma, hyperplasia and carcinoma. Parathyroid adenomas and hyperplasia and carcinomas can all overproduce parathyroid hormone or precursors or active components of the parathyroid hormone. Secondary hyperparathyroidism is usually a reactive parathyroid hyperplasic phenomenon accompanying renal failure. Symptoms of secondary hyperparathyroidism can include nephrolithiasis, bone disease, peptic ulcer, fatigue, muscle aches, depression and hypertension. Untreated hyperparathyroidism can result in loss of bone mass due to hypercalcemia resulting from excessive levels of circulating Parathyroid. A high level of Parathyroid causes unbalanced osteoclastic bone reabsorption that can lead to multiple foci of bone destruction, osteitis fibrosa cystica, or von Recklinghausen's disease of bone. Excess parathyroid hormone is one of the leading causes of osteoporosis and it is a primary cause of kidney stones.

Current treatment for primary hyperparathyroidism generally involves surgical removal or resection of all or part of the abnormal parathyroid tissue. However, parathyroid surgery (parathyroidectomy) requires exceptional skill because the parathyroid glands are notoriously variable in location and intimate knowledge of the intrathyroidal, retroesophageal, lateral neck, and mediastinum anatomy is required. Accordingly, a number of preoperative tests are usually performed to better define the position of the abnormal gland or glands, including but not limited to: thallium-technetium subtraction scans, ultrasound, selective venous sampling, computed tomography (CT), magnetic resonance imaging (MRI), scintigraphy with technetium-99m sestamibi (sestamibi scanning), and arteriography. Despite this, many parathyroidectomies fail due to failure to localize the parathyroid on diagnostic examinations or because of surgical failure to identify and remove the dysfunctional parathyroid gland. Other complications and attendant risks of surgical treatment of hyperparathyroidism include excessive removal of parathyroid glands tissue, hematoma, vocal cord paralysis, hypocalcemia, and persistent hypercalcemia. Moreover, conventional surgical techniques typically do not allow for the accurate partial removal of abnormal parathyroid glands, thus, even when single glandular disease is involved, a multiple glandular parathyroidectomy is performed. Other parathyroid-based diseases include primary hypoparathyroidism, which is caused by deficient Parathyroid hormone secretions, and which in turn can cause low serum calcium due to a lack of Parathyroid hormone mediated bone resorption and calcium reabsorption by the kidneys. Symptoms of hypocalcemia can include neuromuscular irritability and tetany. Intravenous calcium is currently the treatment of choice for primary hypoparathyroidism, but Parathyroid hormone replacement has also been used to treat primary hypoparathyroidism. However, Parathyroid hormone replacement therapy is costly and most clinicians lack clinical experience with this treatment.

Therefore, what is needed are improved methods, devices and systems for treating parathyroid-based or related diseases and conditions. The present invention is directed to meeting these, as well as other, needs.

SUMMARY

Accordingly, the invention provides methods, devices and systems to treat various parathyroid-based diseases, including but not limited to calcium metabolism, hyperparathyroidism, hypercalcemia, osteoporosis and the secondary effects related to the balance of parathyroid hormone and its active elements.

One embodiment provides a tightly targeted minimally invasive therapy (TTMIT) parathyroid tissue ablating instrument. A substance that cytotoxically ablates parathyroidal tissue within a parathyroid gland of a living human during application in the parathyroidal tissue of therapeutically sufficient units of an electromagnetic energy having a frequency only ranging from ultraviolet to visible to near infrared, wherein the substance is at least one of a non-mitochondrial cell component agent, a bio-activation agent, a bio-degradation agent, a chemical change agent, a methylation agent, a carboxylation, an acetylation agent, a de-methylation agent, a de-carboxylation agent, a carbon monoxide agent, a carbon dioxide agent, an antibody agent, an antibody analog agent, nanotechnology, an enzymatic agent, an enzymatic analog agent, a protein agent, a peptide agent, a peptide analog agent, a peptide modification agent, a parathyroid receptor agent, a parathyroid receptor analog agent, a partial parathyroid hormone receptor agent, a full parathyroid hormone receptor agent, cinacalcet, a cinacalcet analog agent, sestamibi, a sestamibi analog agent, a parathyroid hormone agent, a parathyroid precursor agent, an active portion of the parathyroid hormone agent, a partial portion of the parathyroid hormone agent, a full portion of the parathyroid hormone agent, a calcium agent, a calcium analog compound agent, an organic compound agent that can bind to parathyroid receptors, an inorganic compound agent that can bind to parathyroid receptors, an organic compound agent that can bind to parathyroid calcium receptors, and an inorganic compound agent that can bind to parathyroid calcium receptors, is included. A substance delivery device is configured to introduce the substance into the parathyroidal tissue. An electromagnetic energy treatment device is configured to apply the therapeutically sufficient units of the electromagnetic energy within a thermal range that is non-cytotoxic to the parathyroidal tissue to the substance after the substance has been introduced by the substance delivery device into the parathyroidal tissue. A sensor is operationally coupled to the electromagnetic energy treatment device and the sensor is configured to monitor activation of the substance for the electromagnetic energy treatment device as the therapeutically sufficient units of the electromagnetic energy are applied. The electromagnetic energy treatment device is further configured to modulate applying the therapeutically sufficient units of the electromagnetic energy once the substance has been activated.

A further embodiment provides a tightly targeted minimally invasive therapy (TTMIT) parathyroid tissue ablating instrument. A substance that cytotoxically ablates parathyroidal tissue within a parathyroid gland of a living human during application in the parathyroidal tissue of therapeutically sufficient units of an electromagnetic energy having a frequency only ranging from ultraviolet to visible to near infrared is included. A substance delivery device is configured to introduce the substance into the parathyroidal tissue and to limit quantity and distribution of the substance being introduced, wherein the substance is at least one of a non-mitochondrial cell component agent, a bio-activation agent, a bio-degradation agent, a chemical change agent, a methylation agent, a carboxylation, an acetylation agent, a de-methylation agent, a de-carboxylation agent, a carbon monoxide agent, a carbon dioxide agent, an antibody agent, an antibody analog agent, nanotechnology, an enzymatic agent, an enzymatic analog agent, a protein agent, a peptide agent, a peptide analog agent, a peptide modification agent, a parathyroid receptor agent, a parathyroid receptor analog agent, a partial parathyroid hormone receptor agent, a full parathyroid hormone receptor agent, cinacalcet, a cinacalcet analog agent, sestamibi, a sestamibi analog agent, a parathyroid hormone agent, a parathyroid precursor agent, an active portion of the parathyroid hormone agent, a partial portion of the parathyroid hormone agent, a full portion of the parathyroid hormone agent, a calcium agent, a calcium analog compound agent, an organic compound agent that can bind to parathyroid receptors, an inorganic compound agent that can bind to parathyroid receptors, an organic compound agent that can bind to parathyroid calcium receptors, and an inorganic compound agent that can bind to parathyroid calcium receptors. An electromagnetic energy treatment device is configured to apply the therapeutically sufficient units of the electromagnetic energy within a thermal range that is non-cytotoxic to the parathyroidal tissue to the substance after the substance has been introduced by the substance delivery device into the parathyroidal tissue. A sensor is operationally coupled to the electromagnetic energy treatment device and the sensor is configured to monitor activation of the substance for the electromagnetic energy treatment device as the therapeutically sufficient units of the electromagnetic energy are applied. The electromagnetic energy treatment device is further configured to modulate applying the therapeutically sufficient units of the electromagnetic energy once the substance has been activated.

A still further embodiment provides a tightly targeted minimally invasive therapy (TTMIT) parathyroid tissue ablating instrument. An electromagnetic energy treatment device is configured to apply therapeutically sufficient units of an electromagnetic energy having a frequency only ranging from ultraviolet to visible to near infrared into parathyroidal tissue of a parathyroid gland of a living human. A substance that cytotoxically ablates parathyroidal tissue within the parathyroid gland during application in the parathyroidal tissue of the therapeutically sufficient units of the electromagnetic energy having a frequency only ranging from ultraviolet to visible to near infrared, wherein the substance is at least one of a non-mitochondrial cell component agent, a bio-activation agent, a bio-degradation agent, a chemical change agent, a methylation agent, a carboxylation, an acetylation agent, a de-methylation agent, a de-carboxylation agent, a carbon monoxide agent, a carbon dioxide agent, an antibody agent, an antibody analog agent, nanotechnology, an enzymatic agent, an enzymatic analog agent, a protein agent, a peptide agent, a peptide analog agent, a peptide modification agent, a parathyroid receptor agent, a parathyroid receptor analog agent, a partial parathyroid hormone receptor agent, a full parathyroid hormone receptor agent, cinacalcet, a cinacalcet analog agent, sestamibi, a sestamibi analog agent, a parathyroid hormone agent, a parathyroid precursor agent, an active portion of the parathyroid hormone agent, a partial portion of the parathyroid hormone agent, a full portion of the parathyroid hormone agent, a calcium agent, a calcium analog compound agent, an organic compound agent that can bind to parathyroid receptors, an inorganic compound agent that can bind to parathyroid receptors, an organic compound agent that can bind to parathyroid calcium receptors, and an inorganic compound agent that can bind to parathyroid calcium receptors, is included. A substance delivery device is configured to introduce the substance into the parathyroidal tissue. A sensor is operationally coupled to the substance delivery device and the sensor is configured to monitor activation of the substance for the substance delivery device as the therapeutically sufficient units of the electromagnetic energy are applied. The substance delivery device is further configured to limit the therapeutically sufficient units of the electromagnetic energy to a thermal range that is non-cytotoxic to the parathyroidal tissue and to control introducing the substance once the substance has been activated.

A yet further embodiment provides a tightly targeted minimally invasive therapy (TTMIT) parathyroid tissue ablating instrument. An electromagnetic energy treatment device is configured to apply therapeutically sufficient units of an electromagnetic energy having a frequency only ranging from ultraviolet to visible to near infrared into a targeted radius within parathyroidal tissue of a parathyroid gland of a living human. A substance that cytotoxically ablates parathyroidal tissue within the parathyroid gland during application in the parathyroidal tissue of the therapeutically sufficient units of the electromagnetic energy having a frequency only ranging from ultraviolet to visible to near infrared, wherein the substance is at least one of a non-mitochondrial cell component agent, a bio-activation agent, a bio-degradation agent, a chemical change agent, a methylation agent, a carboxylation, an acetylation agent, a de-methylation agent, a de-carboxylation agent, a carbon monoxide agent, a carbon dioxide agent, an antibody agent, an antibody analog agent, nanotechnology, an enzymatic agent, an enzymatic analog agent, a protein agent, a peptide agent, a peptide analog agent, a peptide modification agent, a parathyroid receptor agent, a parathyroid receptor analog agent, a partial parathyroid hormone receptor agent, a full parathyroid hormone receptor agent, cinacalcet, a cinacalcet analog agent, sestamibi, a sestamibi analog agent, a parathyroid hormone agent, a parathyroid precursor agent, an active portion of the parathyroid hormone agent, a partial portion of the parathyroid hormone agent, a full portion of the parathyroid hormone agent, a calcium agent, a calcium analog compound agent, an organic compound agent that can bind to parathyroid receptors, an inorganic compound agent that can bind to parathyroid receptors, an organic compound agent that can bind to parathyroid calcium receptors, and an inorganic compound agent that can bind to parathyroid calcium receptors, is included. A substance delivery device is configured to introduce the substance into the parathyroidal tissue. A sensor is operationally coupled to the substance delivery device and the sensor is configured to monitor activation of the substance for the substance delivery device as the therapeutically sufficient units of the electromagnetic energy are applied within the targeted radius. The substance delivery device is further configured to limit the therapeutically sufficient units of the electromagnetic energy to a thermal range that is non-cytotoxic to the parathyroidal tissue and to control introducing the substance once the substance has been activated.

In an alternative embodiment, the invention provides methods for the controlled partial or complete ablation of one or more parathyroid glands.

In an alternative embodiment, the invention provides a method for controlling the function of the parathyroid function. The parathyroid gland can include but is not restricted to the parathyroid tissue and cells, parathyroid vasculature, parathyroid nerves and the parathyroid local tissue.

Controlling the parathyroid gland function can include but is not restricted to ablating or destroying function or tissue of part or all of the parathyroid gland and can include methods for increasing or decreasing or modulating the function of the parathyroid gland, which can include but is not restricted to altering the release or function of the parathyroid hormone. Controlling the parathyroid gland function shall be referred to as treating the parathyroid gland.

Although the use of minimally invasive therapy (MIT) has been used to kill and treat aggressive or malignant tumors that arise or metastasize to many organs, the use of MIT to treat hyper-functioning glands has been limited but has been limited predominantly to the thyroid gland. Ethanol (alcohol) percutaneous injections have been used to ablate the parathyroid gland.

Some MIT devices include but are not restricted to Radiofrequency ablation (RF) and microwave (MW) and laser (L), Cryotherapy (CryT), High Intensity Focused Ultrasound (HIFU), Radioactive Therapy (Brachytherapy: BrT), Irreversible Electroporation (IRE), Electrical Current Therapies, Electrocautery, Medication delivery, Medication packets, blood flow reduction, Chemical and Medication Ablation, Activation and Deactivation and Modulation Therapy, Adhesives and Glues and Molecular Crystal and Lattice therapies, Target Tissue Delivery Device Therapies, Peptide and Biological Conversion Therapies, MR and RF and Magnetic External Heating Therapies, Hyperthermia with Adjuvant Therapy, Hypothermia with Adjuvant Therapy, Local protective therapy in the Vicinity of the Target Organ Therapy, Suction and Expansion Therapy, Positive Pressure and Expansion Therapy, Mechanical Ablation Therapy and Combinations of Therapies.

The use of MIT for the parathyroid gland (Parathyroid gland) has been limited. The use of alcohol ablation has been reported but is of limited acceptance in part because the use and contact of alcohol in biological tissue is extremely dangerous and is poorly controlled. Any leakage of alcohol outside of the target organ, which in this case is the Parathyroid gland can and will likely permanently destroy or damage tissue with which it makes contact. In the case of the parathyroid gland the tissue in the vicinity of the Parathyroid gland can include but is not restricted to local nerves such as the Vagus nerve and the Recurrent Laryngeal nerves and vascular structures such as the Carotid artery and the Jugular vein as well as local organ tissue such as the esophagus.

MIT other than alcohol (ETOH) is proposed as a method to treat the parathyroid gland and hyperparathyroidism. In order to make MIT most effective adjustments in the therapy are recommended that achieve full or partial ablation of abnormal parathyroid tissue or full or partial modulation of parathyroid tissue function. This means that the MIT must have enough precision that the targeted tissue such as the parathyroid tissue is treated effectively and the local tissue is preserved. This will result in the return of normal function to the parathyroid hormonal balance while preserving and not damaging the local tissues such as the nerves and arteries and organs that reside in the vicinity of the parathyroid glands.

This more highly focused treatment is referred to as Tightly Targeted Minimally Invasive Therapy (TTMIT). TTMIT has different strategies and requires adaptation of present devices and energy and treatment protocols and treatment delivery methods and patterns of treatment.

Minimally invasive therapy often is directed to destroy tissue such as malignant or aggressive tumors. One of the objectives is also to damage the local healthy tissue adjacent to the malignant or aggressive tumor. This is because the adjacent macroscopically normal tissue often contains microscopic malignant or aggressive tumor. This same approach is applicable to the heart and MIT of aberrant nerves and conductive tissue that are responsible for irregular heartbeats such as atrial fibrillation. The discrete location of the nerves to be treated is often poorly defined. As a result MIT is designed to create a penumbra of tissue damage that extends into the interface between normal and abnormal tissue.

The current invention and use of currently available MIT devices and newly invented MIT devices are designed to limit the damage or destruction or control or reduction of abnormally functioning tissue of the Parathyroid gland and minimize or eliminate the local tissue damage. The techniques and the use of these MIT devices are designed to restrict the MIT to the Parathyroid gland and reduce or eliminate the effects of MIT on local tissue or tissue adjacent to the parathyroid gland. Some of these techniques and uses will include but are not restricted to ablation of the vessels serving the abnormal parathyroid by restricting inflow and/ or outflow of blood from the Parathyroid; severing the neural connection to the Parathyroid gland; and eliminating some or all of the functioning Parathyroid gland tissue in the abnormal gland that is producing excess amounts of Parathyroid gland hormone. Partial or controlled ablation of the parathyroid glands will be an acceptable endpoint in some patients. The parathyroid gland is fairly unique in the body. Since there are four normal glands, an individual gland can be destroyed partially or fully, and normal parathyroid function can be preserved if at least one normal gland remains. In addition, in some renal failure patients all four glands can become abnormal. In those patients the desired treatment is to remove three of the glands and preserve a portion of the fourth gland. Over time this gland can grow and produce too much Parathyroid gland hormone. Ablation of a portion but not all of the remaining Parathyroid gland will become the objective in follow-up treatments. The desired outcome is not to remove all parathyroid tissue from the body which is the objective of malignant tumor removal, but rather the objective is to return the body to normal endocrine function such as but not restricted to returning the calcium blood levels and the parathyroid hormone levels and the parathyroid hormone function back to normal levels and to accomplish this some parathyroid tissue must persist in the body.

Therefore unlike most MIT the treatment objective in the Parathyroid gland is to be able to tightly titrate the ablation of parathyroid tissue so that it is controllable such that either a portion or all of the gland can be rendered non-functioning or render at least one but less than four of the glands non-functioning such that by treating one gland the local tissue is not damaged and the other parathyroid glands are not damaged unless treatment is directed specifically at that other specific Parathyroid gland or glands.

The treatment of the parathyroid gland is unique because most other hormone producing glands of the body are not duplicative, more than one gland and most glands do not have a local environment that contains such vital and neural and vascular and organ tissue in such close proximity, where the margin of error in treating that gland is as critical as that of the Parathyroid gland.

Tightly Targeted MIT (TTMIT) could theoretically be used for other hyper-functioning endocrine tissue and may be useful for ablation of even malignant or aggressive tumor tissue that lies near or adjacent to vital structures that cannot be damaged by a penumbra of collateral damage that can be caused by MIT.

Even the thyroid gland which can develop hyper-functioning nodules and which has been treated with MIT methods has very different characteristics than the Parathyroid gland. If the thyroid develops hyper-functioning nodules currently the treatment has a much greater latitude for error and the destruction of the local normal tissue surrounding that abnormal nodule is not a significant issue because there is usually enough normal thyroid tissue that is preserved that there is little to no negative effect in destroying normal tissue and the fact that the abnormal nodules are embedded in the normal thyroid protects the local neural and vascular and organ tissue to a much greater degree than treatment of the Parathyroid gland. The margin of error in the MIT of the Parathyroid gland is smaller and less forgiving than that of the thyroid and makes the objectives and treatment requirements very different between the thyroid and parathyroid glands.

Also the parathyroid gland has a relatively unique blood supply. The branch arteries and veins associated with Parathyroid gland are dedicated to that gland and if these Parathyroid gland vessels can be targeted specifically and ablated or coagulated or reduced in function than the functional tissue of the parathyroid can be manipulated and reduced in that specific Parathyroid gland without damaging the other parathyroid glands and without damaging the function of other local tissue or the local thyroid glands.

The Parathyroid gland is fairly unique because it is encapsulated and has four stand-alone endocrine glands and one parathyroid or even a portion of one parathyroid gland can be adequate to produce enough parathyroid hormone to keep the body in parathyroid hormone normal homeostasis. Therefore, tightly targeted MIT with smaller or no penumbra of collateral damage is the goal and is optimal for the Parathyroid gland but is less desirable or even not desired for the standard MIT used to treat aggressive benign or malignant tumors, which are the primary focus of current MIT treatment. Such TTMIT may even be less optimal for some other endocrine hyper-functioning nodules or adenomas such as the thyroid where the margins of the hyper-functioning nodules or adenomas integrate themselves into the normal thyroid tissue than it is for the abnormal parathyroid gland.

Other endocrine glands that can be hyper-functioning but in which the preservation of normal functioning tissue is important can include the adrenals and adenomas of the most superficial cortical layer, the zona glomerulosa and its production of mineralocorticoids (e.g., aldosterone); middle cortical layer, the zona fasciculata and its production of glucocorticoids (e.g., cortisol); and the deepest cortical layer, the zona reticularis and its production of weak androgens (e.g., dehydroepiandrosterone, adrenosterone).

Non-endocrine tissue but tissue that is involved with the production or stimulation or suppression of endocrine tissue can include neural tissue such as the pituitary and adenomas of the pituitary such as but not restricted to prolactinomas. Reduction of the volume of the prolactinoma can both reduce the over-production of prolactin and reduce the compression of normal pituitary tissue which is compromised by the large size of the prolactinoma in the sella which is a limited space and which reduces function of normal tissue function in the pituitary of other hormone releasing factors such as but not restricted to thyroid stimulating hormone, and anti-diuretic hormone.

Lesions in the brain that are not malignant or aggressive tumors can include but are not restricted to abnormal foci of neural activity to include but not restricted to seizure foci, aggressive behavior sexual and violent and verbal, and traumatic memories such as memories creating post-traumatic stress disorder and infectious foci could also be benefited by TTMIT.

Tissues that over produce hormones and peptides and chemicals such as but not restricted to over-production of acid in the stomach by chief cells, or insulin or glucagon as related to the pancreas could be treated with TTMIT.

One goal of TTMIT is return to normal function such as but not restricted to hormonal return to normal function of parathyroid function. This can be achieved by functional reduction of hormone producing cells such that ablation or modulation of the tissue preserves vital normal function but eliminates the excess or non-vital function especially in hormonal or peptide producing tissues. It can also be the return of normal function of other tissues such as neural tissue and remove or reduce the presence of damaged tissue such as but not restricted to seizure foci or destructive memories such as but not restricted to traumatic memories. TTMIT is designed for pinpoint or more restricted and controlled ablation or down-regulation or decrease in cell function without creating larger zones of collateral damage.

Currently, most MIT is designed to fully ablate the tissue target and often is designed to ablate a margin of tissue often 5 to 10 mm beyond the primary target.

The parathyroid is unique in that the fact that there are four parathyroid glands that control calcium metabolism through the parathyroid hormone. When the parathyroid glands develops dysfunction, in general one or two glands become abnormal. TTMIT can be used to treat the abnormal gland and reduce the amount of abnormal tissue. With renal failure there can be up to four glands that become abnormal and TTMIT can be used to control abnormal hormonal secretion and can replace the use of Sensipar, which is a pharmacologic method for treating hyperparathyroidism and can replace surgery in which 4 glands need to be surgically approached which can lead to hypoparathyroidism. The preferred embodiments can to be used for treating the parathyroid gland and controlling excess chemical peptide or hormonal secretion. In other embodiments, the current treatment can be used to control excess secretion of other hormone or peptide or chemical secreting organs. The parathyroid glands are relatively unique compared to most peptide or hormone secreting organs because of their multiplicity and their tendency to become hyperplastic or adenomatous and offers an opportunity to control function.

BRIEF DESCRIPTION OF THE DRAWINGS

FIG. 4 is a rendering of a guiding device with a blunt end. Inside of the guiding device is a tube/conduit that can have one or more than one channel.

FIG. 5 is a rendering of a guiding device penetrating the parathyroid tissue. In one embodiment the tube can be a needle can have a thread-like configuration that penetrates the parathyroid with a screw-like motion or mechanism.

FIG. 17A demonstrates MIT with a zone of ablation that affects both the parathyroid target tissue and the vicinity tissue whereas, with FIG. 17B TTMIT only the parathyroid gland is ablated.

FIG. 20 is a delivery device that can include but is not restricted to a tube or catheter or conduit, needle or guide that can have side-holes or fenestrations of variable size that can be greater in diameter proximal than distal or greater in diameter distal than proximal or any combination of sizes of side-holes.

FIG. 21A is a tube or catheter or conduit, needle or guide, which can have a variable sized distal end hole or the end of a conduit can be closed and contain no end-hole and be closed at the distal end. The conduits can be partially or fully composed of insulation and the insulation can include but is not restricted to insulation from electromagnetic, thermal, kinetic or mechanical forces or energy. In one embodiment a laser energy delivery device can reside within an insulator tube/catheter or conduit, which can have a variable sized holes and can modulate or alter the lasers' effect upon the target tissue, including the parathyroid gland. In FIG. 21B in one embodiment this can use side-holes or fenestrations that can be of variable size and shape including geometric and non-geometric and logarithmic and logarithmic paper shapes or cut-outs on a logarithmic pattern and can include one or more than one a tube/catheter or conduit, needle or guide, which can have a variable sized distal hole and a guide or sheath that is closed at the distal end and these insulating tubes or conduits can move or rotate to expose greater or lesser amounts of the energy treatment or substance for treatment to the target tissue, parathyroid gland. This embodiment can include a laser treatment device and two conduits that contain openings that can include but are not restricted to slits or holes that serve as fenestrations or windows to the laser light. When the conduit fenestrations are not aligned the amount of light or heat escaping the two conduits and reaching the target tissue is more limited than when the fenestrations are aligned. This can also be organized on a logarithmic graph pattern with cut out slits that can tightly control the amount of light that is emitted to the target tissue.

FIG. 25A depicts a stylet that when exposed to cold becomes rigid and straight and when exposed to a designated heat becomes flexible. FIG. 25B depicts a hook that when exposed to cold becomes rigid and straight and when exposed to a designated heat becomes flexible.

FIG. 29A is an embodiment in which a form of delivery packets or agitating substance can be delivered percutaneously or non-percutaneously and can be used to deliver a substance such as medication to ablate the target tissue. In FIG. 29A the substance delivered through the delivery packet does not require a second substance or energy source for activation. In FIG. 29B the substance delivered through the agitation substance or delivery packet does require a second substance or energy source for activation. In FIG. 29C the substance delivered through the agitation substance or delivery packet does require a second substance or energy source for activation and the energy source can be a transcutaneous device such as but not restricted to ultrasound.

DETAILED DESCRIPTION

Figure 1:
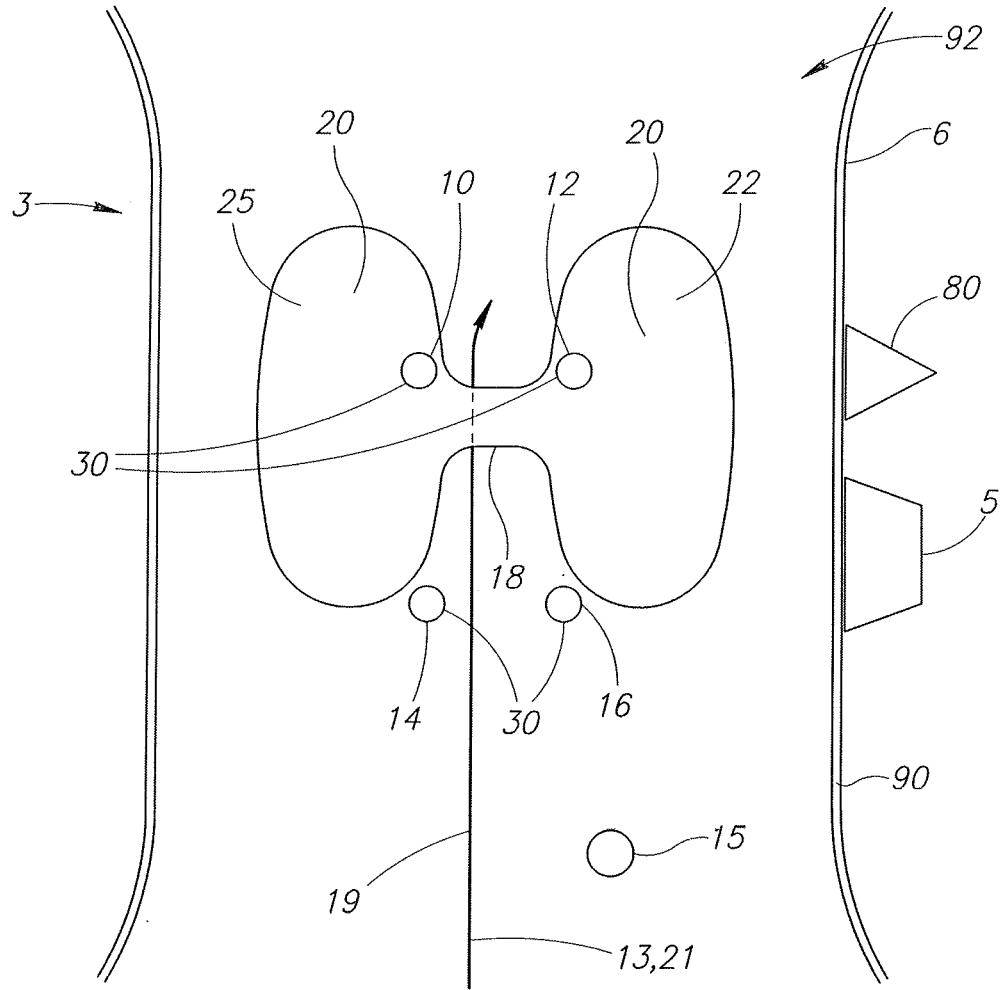
FIG. 1 is a frontal view, anatomic rendering of the thyroid and parathyroid glands in the anterior mid neck.

In the current invention, methods for more pinpoint and precise targeting without heating may be achieved by irreversible electroporation (IRE) and this may prove an optimal method for treating the abnormal Parathyroid gland. Methods for more pinpoint and precise targeting with heating may be effectively used on the Parathyroid gland using high-intensity focused ultrasound (HIFU). IRE and HIFU as well as other MIT and TTMIT methods including but not restricted to MW, RF, L, CryoT, and chemical ablative techniques, adjuvant therapy, chemo therapy or radiation or any combination of these methods can be used in conjunction with but not restricted to small local incisions or laparoscopy or percutaneous needle placement in or near or adjacent to the tissue such as but not restricted to the Parathyroid gland.

Ischemic ablation is a primary mechanism of Parathyroid gland treatment. Thrombosing the arterial inflow leads to ischemia and cell death, while eliminating venous outflow results in Parathyroid gland interstitial tissue increased pressure and resultant cell death by osmotic and toxic means and by secondary ischemia and cell death if the Parathyroid gland intra-gland pressure exceeds arterial inflow pressure. Ischemic ablation can be achieved by using high-intensity focused ultrasound (HIFU). IRE and HIFU as well as other MIT and TTMIT methods include but are not restricted to MW, RF, L, CT, and chemical ablative techniques, adjuvant therapy, chemo therapy or radiation or any combination of these methods or methods described within this patent.

Strategies for optimally treating the parathyroid gland may include but are not restricted to modifications of the antenna and electrode and can include but are not restricted to changing antenna and electrode length and changing insulation lengths, limiting the maximal heating of the probe with longer durations of the pulse, alternating pulses of short and long, creating a probe in which the insulation or the electrode can be made to vary to be shorter and longer, adjustments of the pulsing sequence with feedback from the damage rendered to the gland or the heating or the cooling in the vicinity tissue, enlargement of the electrode face or tines, individually retractable tines or electrodes which can adjust to target tissue shape and response to therapy of the target tissue and the local vicinity tissue, alternating and variable heating and cooling and a change and must frequently a reduction in the ratio of heat or electromagnetic or kinetic energy delivered to ablate the target tissue compared to heat or electromagnetic or kinetic energy delivered in the tissue in the vicinity of the target tissue.

One embodiment can include hooks to secure the parathyroid gland and these hooks can be non-heat conducting and insulated or heat conducting.

Direct and primary tissue destruction is another primary mechanism of Parathyroid gland treatment. Mechanisms utilized to directly destroy a cell can include but are not restricted to heat, cold, chemical, osmotic, pressure and suction and mechanical, electromagnetic including but not restricted to casing a current through the tissue, and nuclear energetic destruction. Delivery and treatment mechanisms can include but are not restricted to IRE, HIFU, MW, RF, L, CryoT, chemical and adhesive and osmotic and packet delivery systems can include but are not restricted to liposomes and microbubbles and activated and deactivated materials that can be deactivated or activated by a second substance or treatment to include but not restricted to de-carboxylation and de-methylation and activation and inactivation with electromagnetic energy to include but not-restricted to visible light and UV to control the degree of tissue damage in the target organ and in the local environment. Other methods for modulating tissue exposure to heat can include but are not restricted to exposing the tissue and the local tissue and non-target tissue to cooling solutions such as but not restricted to chilled such as chilled or frozen distilled water ionic solutions and non-ionic solutions; ionic solutions such as but not restricted to saline, non-ionic solution such as but not restricted to 5% Dextrose water or distilled water.

In general heating for hyperthermic device have a heat and a duration of exposure to that heat. Tissue damage can occur at heats above 46 degrees C. for 60 minutes but other embodiments can include but are not restricted to heating and duration to include successful ablation of tissue at 70 degrees C. for 60 seconds as a single exposure or two 70 degree C. exposures each for 30 seconds. Generated power can include many different power generated settings and another embodiment can include but is not restricted to 150 Watts producing 100 degrees for 10 minutes.

In another embodiment of radiofrequency ablation, a high-frequency, alternating current with a wavelength of 460-500 kHz can be emitted through an electrode placed within the targeted tissue. Grounding pads applied to the patient's thighs complete the electrical circuit. Deposition of radiofrequency energy results in frictional heating from flowing electrons in cells near the site of energy emission. When living human tissues are heated to more than 49° C., cell death occurs within minutes. Temperatures in excess of 60° C. can cause immediate cell death. The cell death is induced by the denaturation of proteins, which results in the loss of enzymatic function, melting of cell membranes, mitochondria function and destruction of cytoplasm. These events result in direct cyto-destruction of the affected cells. Although some cells are destroyed at temperatures less than 49° C., other cells can survive temperatures approaching 49° C. Alternatively, when temperatures exceed 105° C., cells boil, releasing gas vapor and causing tissue charring. Gas and charred tissue inhibit dispersion of radiofrequency energy, which decreases the effectiveness of some heating and penetration of lethal energy concentrations. Hence, radiofrequency ablation devices should ideally induce prolonged heating of target tissue with temperatures sustained between 50° and 105° C.

For percutaneous imaging-guided radiofrequency ablation, the energy is delivered into the target tissue by means of needlelike electrodes. Radiofrequency ablation electrodes can include but are not restricted to a range in a diameter from 15 to 17 gauge. Each of these devices uses a different strategy to maximize the size of thermal ablation. In one example a system by Radionics can have an electrode that can be shaped like a standard 17-gauge needle and delivered as a single electrode or as a unit of three electrodes arranged in a triangular cluster. The Radionics system increases ablation lesion size by using two enhancements: electrode cooling and pulsed energy delivery. The Radionics device consists of a generator and a 14- or 15-gauge electrode with numerous retractable tines, which are used to increase the area of ablation. The tines are advanced into the area of treatment. The LeVeen system uses a 14-gauge electrode with 12 retractable tines that are advanced into the area of treatment. Each device also uses a slightly different approach to energy delivery and monitoring for thermal destruction.

The theoretical maximum size of the treatment zone has been calculated in vitro for radiofrequency ablation. In vitro, the theoretical maximum size of the ablated area is two times the length of the energy-emitting segment of the electrode for the long axis of the treatment zone. The transverse axis maximum can be up to two-thirds of the length of the long axis of the treatment zone. In vivo, the treatment zone varies and is usually smaller than the theoretical maximum. The maximum size of the treatment zone can be increased by inducing ischemia or by treating devascularized tissue. Alternatively, flowing blood, large fluid-containing spaces, or circulating air can decrease the effective size of the treatment zone. The available radiofrequency devices use generators that deliver 150-200 W of energy.

These heating characteristics may vary from device to device but the general principles of cell death apply to multiple forms of treatment.

Calculating which treatment is optimal for the given target tissue, such as based on the size and location of the Parathyroid gland adenoma, will require a case-by-case individual analysis. A Parathyroid gland adenoma that is 30×12×18 mm and is not near vital arteries or neural structures will need to be treated with different wattage, and power and maximal heating and time duration and number of applications or pulses of the treatment than a Parathyroid gland adenoma that is 10×8×12 mm and lies in close proximity to vital arteries or neural structures.

Thermal Ablation Therapies can include but are not restricted to the following.

Thermal ablation requirements for benign tissue that over-produce hormone such as but not limited to the parathyroid gland differ from carcinomas and malignant behaving tumors because if some functioning or over functioning cells remain this does not pose a serious threat to the survival of the organism being treated. One example is a parathyroid gland that is 90% ablated may be acceptable and may reduce Parathyroid gland hormone levels back to a normal or acceptable range, whereas a 90% kill rate of malignant or aggressive tumor cells would not be acceptable. In addition, if a Parathyroid gland is found to be over-producing parathyroid hormone after one treatment, then a second treatment can be employed whereas that same strategy if applied to an organism with malignant or aggressive tumors carries increased risk to that organism when failing to eradicate malignant or aggressive tumor malignant cells on the first treatment and thus is significantly different and carries greater risk to an organism with a malignant or aggressive tumor than the failure to eradicate some percentage of cells in a benign tumor or mass or adenoma or non-malignant or aggressive cell population. In fact, treatment of the Parathyroid and other benign cells that are over-producing hormone may be treated effectively if not more effectively with multiple treatments, so as to limit or reduce the risk of damage to the structures in the vicinity of the target tissue such as but not restricted to the parathyroid gland. If multiple parathyroid adenomas are present or if there is a mixture of parathyroid hyperplasia and adenomas then treating the parathyroid adenoma first and observing the organisms return to normal calcium homeostasis and parathyroid gland production may warrant a 'watch and wait' policy and not demand any further treatment until the organism's calcium homeostasis or parathyroid gland hormone levels become abnormal. In summary, the treatment of benign parathyroid tissue that is hyper-producing parathyroid hormone can be treated with MIT such that the balance of aggressiveness of treatment is on the side of caution and protection of non-target tissue whereas with a malignant tumor the balance of aggressiveness is more heavily weighted toward destroying the malignant or aggressive tumor.

In one embodiment thermal ablation therapies can either increase or decrease the temperature of the tissue being treated of which the two basic strategies are cryotherapy and hyperthermic therapy, respectively. These therapies induce cell cytotoxicity, irreversible cell destruction and death and necrosis.

The parathyroid gland is unique in that parathyroid hormone levels can return to normal in 10 to 30 minutes after effective removal or treatment of the abnormal parathyroid tissue.

Hyperthermic therapies that induce cytotoxicity are believed to begin at about 46 degrees Celsius (C) for about 60 minutes within the tissue.

Thermal ablation therapies can include but are not restricted to radiofrequency ablation (RF) and microwave (MW) and laser (L), utilizing an optimal temperature of 50 degrees C., and heating of tissue to 50 to 54 degrees C. for 4-6 minutes is a common endpoint for irreversible cytotoxicity. But higher temperatures are generated by the RF or MW or L devices to include 100 degrees, such that the tissue adjacent to the device can experience temperatures of 100 degrees C. which coagulates the adjacent tissue and higher temperatures such as 105 degrees C. to vaporize the adjacent tissue.

In the current invention heat-sinking can be used to reduce local tissue damage. Heat-sinks from blood vessels reduce tissue damage and reduce tissue temperature. Heat-sinking in the current techniques is a drawback and reduces effectiveness of MIT. Or a heat-sink can be created by but not restricted to bathing the target tissue in cooler solutions. Also the target tissue can be isolated or insulated from the non-target tissue. Or the target tissue can be surrounded by a material that reflects or locks-in the heat on the target but spares surrounding tissue such as but not restricted to a heat-conducting material on the inside facing the target and an insulating material on the outside facing the local tissue to be protected.

Hypothermic or Cold Therapy or Cryotherapy (CryoT) can include but is not restricted to:

In one embodiment hypothermic or Cold or Cryotherapy (CryoT) is the treatment of tissue with lower than normal organic temperatures. Temperatures below 0 degrees C. can create freezing to target tissues. Temperatures of minus 20 to minus 40 degrees C. represent the lethal isotherm although the temperatures often used by cryotherapy devices range as low as minus 140 degrees C. inside the ice ball used for treatment or heat-sink of 9 kJ (kilojoules). Many of the limitations such as clefts that exist with malignant or aggressive tumor ablation are not relevant with Parathyroid gland treatment. Needles and probes for treating the Parathyroid gland can be small, as small as 13-gauge (2.4 mm) or smaller because of the Parathyroid gland target requirements but larger probes with size equal to or greater than 15-gauge (1.7 mm) probes may prove effective in the Parathyroid gland. Cryoprobes are designed to create a heat sink and gasses and materials such as but not restricted to Argon, helium and nitrogen can be utilized.

In another embodiment the use of liquid materials such as Nitrogen that cool when allowed to return to a gaseous state can also be percutaneously delivered to the target organ such as the Parathyroid gland.

Various cryoprobes exist that include but are not restricted to reservoirs that contain coolant materials such as but not restricted to nitrous oxide and needles that serve as heat-sinks that can use but are not restricted to argon gas.

In one embodiment, the balloon portion of the catheter is filled with a coolant which applies subzero Celsius temperatures to tissue. In another embodiment the temperature can be less than subzero or alternating temperatures of subzero, zero and above zero can be applied to control the amount of damage to the target tissue, such as but not restricted to the Parathyroid gland.

In another embodiment one or more probes can be used and separated by a distance to maximize tissue death between the probes but also taking into account the zone and radius of ablation.

Or the target tissue can be surrounded by a material that reflects or locks-in the heat on the target but spares surrounding tissue such as but not restricted to a heat-conducting material on the inside facing the target and an insulating material on the outside facing the local tissue to be protected.

Chemical and Medication Therapy can include but is not restricted to the following.

In one embodiment ethanol has been used to ablate parathyroid glands but the risk to local tissue damage such as the neural and vascular and organ tissue is significant because of the uncontrolled nature of injecting Ethanol because it denatures living tissue.

In another embodiment methods whereby substances are injected around the Parathyroid gland can include but are not restricted to water, saline, weak bases such as but not restricted to calcium or sodium bicarbonate can be used to dilute or the tissue surrounding the Parathyroid gland can be neutralized by ethylene glycol or propylene glycol or glycerol or glycerin.

Other chemicals or sclerosants which have not been used but may prove more effective because of their less toxic nature and their greater capacity to be neutralized and can include but are not restricted to acetic acid and other moderate and weaker acids, weaker forms of alcohol or diluted forms of alcohol or other Sotradecol.

Substances that can be injected can be in the solid, liquid, gel or gaseous states or can form a slurry or a mixture or combination of the solid, liquid, gel or gaseous states. Other substances may include but are not restricted to carbon monoxide, saline or dextrose solutions that are saturated in a manner that damages the target tissue which can also be optimized or constructed or delivered to protect the non-target tissue.

In another embodiment the tissue adjacent to the target tissue can be treated with a substance that is protective or can dilute the non-target tissue environment and can include but is not restricted to the solid, liquid, gel or gaseous states or can form a slurry or a mixture or combination of the solid, liquid, gel or gaseous states and that substance is non-toxic and will serve as an antidote or dilute or neutralize the effects of the toxic substance injected into the target tissue such that if the toxic substance leaks out of the target tissue or region being treated such as but not restricted to the Parathyroid gland. One example is injecting carbon monoxide into the Parathyroid gland and placing oxygen in the adjacent tissue. Another example is injecting ammonia or urea into the target organ while flooding the adjacent tissue with saline to dilute the effect of the ammonia or urea.

Substances that can be injected can be in the solid, liquid, gel or gaseous states or can form a slurry or a mixture or combination of the solid, liquid, gel or gaseous states. Other substances may include but are not restricted to carbon monoxide, saline or dextrose solutions that are saturated in a manner that damages the target tissue. Also the tissue adjacent to the target tissue can be treated with a substance that is in the solid, liquid, gel or gaseous states or can form a slurry or a mixture or combination of the solid, liquid, gel or gaseous states and that substance is non-toxic and will serve as an antidote or dilute or neutralize the effects of the toxic substance injected into the target tissue such that if the toxic substance leaks out of the target tissue or region the being treated such as but not restricted to the Parathyroid gland. One example is injecting carbon monoxide into the Parathyroid gland and placing oxygen in the adjacent tissue. Another example is injecting ammonia or urea into the target organ while flooding the adjacent tissue with saline to dilute the effect of the ammonia or urea.

Other forms of chemicals for cauterizing tissue, specifically blood vessels can include but are not restricted to silver nitrate, trichloroacetic acid and cantharidin, an extract of the blister beetle that causes epidermal necrosis and blistering.

Electromagnetic therapy can include but is not restricted to the following.

Radioactive (Brachytherapy)

Radioactive materials, brachytherapy, can be used to percutaneously place electromagnetic energy into the target tissue to modulate control of biological function in tissue that is functioning in an aberrant manner. In one embodiment bachytherapy can be used in a hyperactive Parathyroid gland. In one embodiment the radioactive seeds can be implanted and left in place and the isotope which uses a low dose of radiation (brachytherapy) with a limited zone of radiation can be used and can include but is not restricted to iodine-125 or palladium-103. In another embodiment a high radiation dose isotope can be inserted into the Parathyroid gland for a limited period and then removed and this can include iridium-192 which would be inserted into the Parathyroid gland percutaneously for less than 15 minutes. The dose is dependent upon the size of the Parathyroid gland adenoma and the tissue in the vicinity that may be sensitive to the irradiation. In the preferred embodiment the radiation would be introduced through a percutaneous guide and guiding system.

Radiofrequency Therapies

In one embodiment during Radiofrequency probe ablation an electrical current oscillates through the ion channels that are inherently present in biological tissue. Since biological tissue is an imperfect generator of electrical current, frictional agitation and heat are produced. This is known as the Joule effect. Tissue heating is greatest nearest the probe and more distant tissue receives a thermal conduction and thus heat drops off away from the probe. Augmentation of the RF effect can be performed by increasing the probe surface area, pulsing the input power and injecting saline/ionic solutions.

RF ablation can use a single or multiple tines. The needles can be insulated and cooled by water. Tines come in many shapes and configuration and multiple gauge sizes approximating 14 gauge (2.1 mm) to 17 gauge (1.5 mm). For the purpose of the Parathyroid gland smaller gauge probes, one or two tines and smaller tines may provide a smaller and more controlled zone of tissue damage.

The multipolar or bipolar RF probe may prove more effective than the monopolar probe in the Parathyroid gland.

With the multipolar and bipolar RF probe the current oscillates between the two electrodes. Saline can be instilled within the Parathyroid gland to augment the tissue damage between these two electrodes each of which can be placed at the superior and inferior aspect of the abnormal parathyroid gland while monitoring needle placement using imaging guidance techniques to include but not restricted to real-time ultrasound. Initially, levels of power begin in the 20 to 50 W range but may need to increase dependent on the impedance of the tissue being treated and the adjuvant such as saline and ionic solutions administered. Also by pulsing the generator the size of the tissue lesion can be controlled. Since pulsing algorithms have been shown to increase ablation zone size and decrease the time for treatment, the Parathyroid gland may be better treated with an algorithm that decreases the ablation zone and is less concerned with treatment time.

RF can be applied in a unipolar or a bipolar or multipolar fashion and the inter-electrode distances can vary depending on the tissue and electrode characteristics (e.g. 5 mm, 10 mm) and the size of the parathyroid target tissue. RF energies can vary (e. g. 500 kHz) that are delivered to the target tissue to include but not restricted to 100 J, 101-200 J, 201-300 J, 301-400 J, 401-500 J, 501-600 J, 601-1000 J, and >1000 J. Results of tissue damage show that when RF energy is applied in a bipolar fashion, the lesions are located between and around the electrode and when applied in a unipolar fashion lesions were found in the catheter/tissue interface. Bipolar mode increased the length of ablation and can but is not restricted to allow for one treatment pulse.

In another embodiment the tip of the electrode can be varied. The larger electrode tip appears to create a larger lesion. Therefore depending on the size of the target tissue such as but not restricted to the Parathyroid gland the size of the electrode tip will be determined by the size of the needle desired for the percutaneous approach with a gauge size of 21 (0.72 mm) being optimal and a size as large as 15 gauge (1.5 mm) approaching the maximal size for safe percutaneous procedures. The electrode tip may be limited by these parameters. In another embodiment a bipolar or multipolar device can be used where the tines spread out as they exit the percutaneous introducer.

In one embodiment anchors or fixation hooks can be employed to stabilize the target tissue such as the parathyroid gland during treatment.

In one example of target tissue ablation the RF energy sufficient to maintain a highest temperature of 100° C. can be delivered for 8-10 minutes for each ablation. The impedance values ranged from 30 to 60Ω. The diameters of the deployed hooks varied between 1 and 3 cm, depending on the target tissue's size and location. The temperature of each hook can be maintained above 90° C. For masses or lesions smaller than 2 cm in diameter, the needle tip was placed in the center of the lesion and the hooks were deployed to reach the deepest margin of the malignant or aggressive tumor or lesion. One ablation was usually enough to destroy the entire target tissue. For larger target tissue, multiple overlapping ablations can be performed (range, two to six ablations) according to the size and shape of the target tissue.

With multi-tined probes a target zone of 3 m can be produced by three tines 17 gauge spaced 5 mm apart at 200 w for 12 minutes. This is likely greater than would be safe for a Parathyroid gland even if it were 3 cm given the collateral zone injury that may occur and decreased duration or energy would likely be indicated in vivo for a large Parathyroid gland (3 cm).

Microwave Ablation

In one embodiment, in the biological system the term microwave ablation describes electromagnetic energy typically at either 915 MHz to 2450 MHz, although microwave refers to electromagnetic energy between 300 MHz and 300 GHz. If microwave energy is continuously applied it can result in temperatures >150 degrees C. in biological tissues. Antennas are needlelike or looped. Current biological systems in general are monopole, dipole or slotted with the smallest gauge system being 13 gauge.

Microwave ablation refers to the use of all electromagnetic methods for inducing lesion or tumor destruction by using devices with frequencies of at least 900 MHz). Microwave radiation refers to the region of the electromagnetic spectrum with frequencies from 900 to 2450 MHz. This type of radiation lies between infrared radiation and radio waves. Water molecules ($H_2O$) are polar; that is, the electric charges on the molecules are not symmetric. The alignment and the charges on the atoms are such that the hydrogen side of the molecule has a positive charge, and the oxygen side has a negative charge. Electromagnetic radiation has electric charge as well; the "wave" representation is actually the electric charge on the wave as it flips between positive and negative.

For a microwave oscillating at 9.2, 108 Hz, the charge changes signs nearly 2 billion times a second (9.2 108 Hz). When an oscillating electric charge from radiation interacts with water molecule, it causes the molecule to flip. Microwave radiation is specially tuned to the natural frequency of water molecules of the parathyroid gland to maximize this interaction. As a result of the radiation hitting the molecules, the electrical charge on the water molecule flips back and forth 2-5 billion times a second depending on the frequency of the microwave energy. Temperature is a measure of how fast molecules move in a substance, and the vigorous movement of water molecules raises the temperature of water. Therefore, electromagnetic microwaves heat matter by agitating water molecules in the surrounding tissue, producing friction and heat, thus inducing cellular death via coagulation necrosis.

One embodiment can include but is not restricted to a thin (14.5-gauge) microwave antenna that is placed directly into the target tissue, such as the Parathyroid gland. When the antenna is attached to the microwave generator with a coaxial cable, an electromagnetic microwave is emitted from the exposed, non-insulated portion of the antenna. Each generator is capable of producing 60 W of power at a frequency of 915 MHz and one such percutaneous microwave ablation system (Vivant Medical, Mountain View, CA).

Different configurations exist for MW antennas, which include but are not restricted to triaxial, slotted and choked. Given that the choked antenna is 99% efficient and given its profile of ablation and that it can be produced in 9-10 gauge antennas this may prove the current optimal antenna for the Parathyroid gland adenoma.

Laser Ablation

In one embodiment laser sources include but are not restricted to neodymium-doped yttrium aluminum garnet and semi-conductor diodes that emit approximately 600-1000 nm wavelength light energy. Laser may be ideal for the Parathyroid gland ablation. Limitations and disadvantages that exist for lasers with lesions and tumors and other tissue applications may prove beneficial for the Parathyroid gland. Laser light is efficient and precise for tissue heating. Laser light when it strikes body tissue becomes scattered and absorbed rapidly this causes lasers to have limited energy penetration and thus produce smaller zones of ablation (10 to 20 mm) than other devices. Light also does not penetrate charred and damaged tissue. The Parathyroid gland adenomas are commonly 15 mm or less making laser treatment ablation optimal for the Parathyroid gland adenomas.

Medical lasers that can include but are not restricted to $CO_2$ lasers, diode lasers, dye lasers, excimer lasers, fiber lasers, gas lasers, free electron lasers, and optical parametric oscillators.

In one embodiment laser irradiation can be performed with a 1.064-nm Nd:YAG laser and variable wattage can include 2, 3, 5, or 7 W and total delivered energy of 500, 1,000, 1,500 or 2,000 J, respectively. One or multiple illuminations can be performed. Between 600 and 1600 J for a lesion of approximate size of 10 mm maximal length may prove optimal for the Parathyroid gland of that length but the treatment parameters will ultimately be dependent on the actual size of the Parathyroid gland adenoma and its location to vital neural and arterial structures. Low-energy output (2-5 W per fiber) close to the implanted fiber tip, the temperature exceeds 100° C. and results in vaporization of the core of the lesion. Laser advantages include a precise zone of tissue damage.

Ultrasound Ablation

HIFU Ultrasound devises are greater than 13 gauge. HIFU can be used to transcutaneously ablate lesions. One embodiment can include but is not restricted to a 1.06 MHz HIFU transducer which can be used over a treatment diameter of approximately 45.2×18.3-mm rectangular opening. The HIFU transducer was spherically focused, with a 63t 3 mm geometric focus, 64-mm active diameter, and an 18×45-mm2 rectangular cutout to enable coaxial placement of a linear array and the transducer can be driven continuously at its operating frequency increasing uniformly from 3.6 to 8.0 MPa at variable exposure durations (e. g. 2, 5, or 10 seconds). Typically the HIFU can generate temperatures between 65 and 85 degrees Celsius. Typical diagnostic ultrasound transducers deliver ultrasound with time-averaged intensities of approximately 0.1-100 mW/cm2 or compression and rarefaction pressures of 0.001-0.003 MPa, depending on the mode of imaging (B-mode, pulsed Doppler sonography, or continuous wave Doppler sonography). In contrast, HIFU transducers deliver ultrasound with intensities in the range of 100-10,000 W/cm2 to the focal region, with peak compression pressures of up to 30 MPa and peak rarefaction pressures up to 10 MPa.

Electrical current therapy and Irreversible Electroporation (IRE) and Electrocautery Therapy can include but are not restricted to the following.

In one embodiment Irreversible Electroporation (IRE) may prove the most effective means of treating Parathyroid gland adenomas because it produces no excess heat. Cells are eradicated by using several micro to millisecond pulses of electrical current and generate fields up to 3 kV/cm, which irreversibly damage cell membranes and generate apoptosis. IRE is little affected by heat sinks and creates less damage to collagen tissue and nerves and, thus, is optimal for the Parathyroid gland which has the Recurrent Laryngeal nerve and the Vagus in its close vicinity. IRE also can use a thin 19 gauge needle (1.1 mm) that is insulated, larger needles are also available. A single needle bipolar electrode is available or multiple electrodes can be implanted. The electrical current can involve high voltage pulses, which are less frequently applied or lower voltage pulses which may require several hundred pulses.

Coagulation may be limited with IRE and this injection of coagulation factors into the Parathyroid gland after the application of IRE to the Parathyroid gland may be useful adjunct medication.

In another embodiment an electrocautery device can be used similar to those used in surgery to cauterize blood vessels whereby an electrical current heats the cautery device and the heated tip is place on or in the Parathyroid gland and destroys the living tissue, specifically this can be targeted to the blood vessels of the Parathyroid gland and can cause electrocoagulation of the Parathyroid gland blood vessels.

In another embodiment Electrocautery can be combined with other treatment modalities to include but not restricted to Irreversible Electroporation (IRE). IRE does not coagulate vessels in the same manner as thermal methods of treatment and to decrease the risk of bleeding from the target tissue such as but not restricted to the parathyroid gland blood vessels, electrocautery may be needed to control bleeding.

Parathyroid Arterial Blood flow reduction can include but is not restricted to the following.

In one embodiment injection of arterial and arteriolar vasospastic agents such but not restricted to as epinephrine and epinephrine-like medications can assist with MIT and TTMIT of the Parathyroid gland. Additionally other pharmacologic agents designed to reduce tissue perfusion can include but are not restricted to halothane and arsenic trioxide and antiangiogenic therapies such as but not restricted to sorafenib can be used in combination with TTMIT or alone to treat Parathyroid gland adenomas. All the MIT and TTMIT modalities can be used alone or in combination to control and target the target tissue arterial and venous blood flow as the primary or secondary site for resultant ablation.

Medication Carrying Packets Therapy can include but is not restricted to the following.

In one embodiment medication agents can include but are not restricted to organic or inorganic agents and pharmacologic agents and biological agents can be carried in packages that can deliver these agents to target tissues. This can include but is not restricted to delivery through the bloodstream, CSF or through catheters, or needles or other percutaneous methods.

Carrying packages can include but are not restricted to liposomes which can include but are not restricted to multilamellar vesicles, small unilamellar and large unilamellar vesicles and microbubbles which are bubbles smaller than a millimeter. Microbubbles can be filled with perfluorocarbon or air or other gasses or can be filled with other materials to include but not restricted to medication agents and pharmacology agents and biological agents. The microbubble shell can consist of but is not restricted to lipids or proteins that can include but are not restricted to serum albumin.

Carrying packets can be but are not restricted to being sensitive to mechanical and vibration or electromagnetic energy including but not restricted to UV or infrared or visible light sensitive or they can be temperature dependent (hyper or hypothermic) exposure or pH or solids or they can be sensitive to exposure to liquids or gasses or a combination of the above which can cause the carrying packets to release the contents of the carrying packet. This may allow the Parathyroid gland tissue to be effectively treated with a lower energy deposition because the carrying packet agent/s are augmenting the destruction of the target tissue to include but not restricted to the Parathyroid gland tissue, while allowing the local tissue to be exposed to an energy dose below the local tissues threshold for damage.

In another embodiment microbubbles can be used to treat the target tissue. The instillation of microbubbles into the target tissue can include but is not restricted to direct percutaneous instillation of the microbubbles into the target tissue, the Parathyroid gland. Using mechanical or vibrational or ultrasonic stimulation the microbubbles can interact with the Parathyroid gland tissue intact or they can release their contents and this process can modulate the ablation of the Parathyroid gland tissue by either acting as a secondary adjuvant, or a repressor of the primary treatment modality. In one example the microbubbles can interact with the vibrational effect of ultrasound or HIFU and augment the heating or destruction of the Parathyroid gland. This may allow the target tissue to include but not restricted to the Parathyroid gland tissue, to be effectively treated with a lower energy deposition because the microbubbles are augmenting the destruction of the tissue, while allowing the local tissue to be exposed to an energy dose below the local tissues threshold for damage. Microbubbles can be formed with various materials to include but not restricted to galactose and other related organic carbohydrates, proteins and fats as well as other organic and inorganic compounds.

Activation and Deactivation and Modulation of the treatment therapy or device can include but is not restricted to the following.

In one embodiment medication agents can include but are not restricted to electromagnetic and mechanical or kinetic energy and organic or inorganic agents and pharmacologic agents and biological agents can be modulated by either activating or deactivating the agent using one or more additional modulating agents to include but not restricted to electromagnetic energy such as but not restricted to ultraviolet light, or radiation; kinetic or thermal energy to include but not restricted to hyper-thermic delivery systems, ultrasound energy or vibrational forces; cryotherapy or hypothermic delivery systems; or liquids, fluids, gels or solids that can include but are not restricted to medications or solvents.

Light is a type of electromagnetic radiation and can be used to activate and deactivate substances. This is a form of photochemical reaction, and follows the Grothuss-Draper law. Photo/Electromagnetic and mechanical/vibration energy can also change the configuration of a molecule or molecular configuration and change its properties enabling an otherwise inaccessible molecule to become accessible (Woodward-Hoffman selection rules) or creating an accessible molecule and making it inaccessible. Some of the most widely used sections of the electromagnetic spectrum are UV 100-400 nm, visible light 400-700 nm and Near Infrared 700-2500 nm. Examples of photo activation can include but are not restricted to photosynthesis, Vitamin D conversion, bioluminescence, phenol and tetraphenylporphyrin, hydrocarbon solvents that use short wavelengths and solvents containing unsaturated bonds that may require higher wavelengths, cyclohexane, acetone and singlet oxygen reactions in general. Cis and Trans rotations of the molecule that can occur in alkenes. Other reactions can include mercaptans, toluene-chlorine, and metallic reactions like UV irradiation of THF solution of molybdenum hexacarbonyl. Transformation of a liquid into a crystal can be used to alter the internal structure of the Parathyroid gland. One reaction can include but is not restricted to photolysis of iron pentacarbonyl. Also carbon nanotubes can be placed into the target tissue and exposed to an intense pulsed light from a laser or an arc lamp. This will produce combustion and temperatures as high as 700 to 1500 degrees C. Another crystal reaction can include alpha-santonin when exposed to sunlight wavelengths.

The electromagnetic source can include a multichromatic light source such as mercury vapor lamps or monochromatic light sources such as LED or Rayonet lamps.

Some activation examples can include but are not restricted to ultraviolet activated persulfate oxidation of phenol in the basic pH conditions. Carbon foam using a coal tar pitch as a precursor can serve as a support for titanium oxide for the catalytic degradation of phenol. Activation of medications with electromagnetic energy or mechanical energy from an activated form to a deactivated or from a deactivated form to an activated form can modulate the rate and speed of the reaction inside of the target tissue specifically the Parathyroid gland or outside of the target tissue.

Adhesives and Glues and Molecular Crystal and Lattice therapies can include but are not restricted to the following.

In one embodiment the injection of medical grade adhesive into the Parathyroid gland can be an effective means for ablating a part or all of the Parathyroid gland. In the preferred embodiment the adhesive can be percutaneously instilled into Parathyroid gland or into the adjacent tissue or the blood vessels associated with the Parathyroid gland and can include but is not restricted to cyanoacrylate adhesive, UV-curable adhesive (e.g. Cyberlite U303), two part filled epoxy (e. g. Cyberpoxy 5895), anaerobic threadlocking adhesive, which is thixotropic (e.g. Titan 7222), methyl methacrylate.

In one embodiment a substance which can include but is not restricted to a solid, liquid, gel or gas can be injected into the target tissue that can include but is not restricted to the Parathyroid gland that is inactive in its primary state but can become activated if a second substance which can include but is not restricted to a solid, liquid, gel or gas is added such as but not restricted to epoxy glues such as but not restricted two part filled epoxy (e.g. Cyberpoxy 5895).

In another embodiment electromagnetic energy can be added to the primary substance, which can include but is not restricted to a solid, liquid, gel or gas and can be activated by an energetic source that can include but is not restricted to electromagnetic energy, radiation, heat, kinetic and mechanical energy and can include UV activated compounds such as but not restricted to UV-curable adhesive (e.g. Cyberlite U303). Other embodiments can include combinations of substances and energetic sources as primary or secondary or additional additives.

The absence of a substance, which can include but is not restricted to a solid, liquid, gel or gas can also activate a primary substance and can include but is not restricted to the absence of one or more gases such as with anaerobic adhesive.

In another embodiment is a lattice or compound that can be placed percutaneously within the target tissue that can contain a substance which can include but is not restricted to a solid, liquid, gel or gas which can suppress or activate or treat the target tissue. One embodiment can include a substance that is placed into the Parathyroid gland and can include but is not restricted to a lattice such as hydroxyapatite, Ca5(PO4)3(OH), Ca10(PO4)6(OH)2, or bone meal, calcium carbonate, hydroxylapatite, hydroxylapatite hydrogel or cinacalcet (Sensipar) or a related calcimimetic substance or a Parathyroid gland suppressing agent.

Target Tissue Delivery Device Therapies can include but are not restricted to the following.

In another embodiment a delivery device can be used to percutaneously deliver a compound that can be directly delivered within the target tissue such as but not restricted to the Parathyroid gland and the substance can include but is not restricted to a solid, liquid, gel or gas and can suppress or activate or treat the target tissue.

In one embodiment a delivery system for the target organ such as but not restricted to the Parathyroid gland can emulate a diabetic insulin pump that measures glucose blood levels and delivers insulin to the blood stream. For the Parathyroid gland the pump would measure Parathyroid gland hormone levels or a form of calcium levels to include but not restricted to ionized calcium or bound or unbound calcium in the blood stream and deliver calcium or a form of calcium or a suppressor or activator of the Parathyroid gland such as cinacalcet or related calcimimetic substance or a Parathyroid gland suppressing agent.

Other embodiments can include but are not restricted to a scaffold or holding structure or slow dissolving or time release substance that can include but is not restricted to a lattices or crystals that can be injected percutaneously adjacent of within a lesion or tumor and the crystals or lattices can contain medications to treat the medical malady or lesion or tumor through the slow release of the compound. In one embodiment the medication can be placed in the healthy tissue adjacent to the lesion or tumor and as the tumor attempts to grow the lesion or tumor encounters the lattice and treating or suppressing or activating medication that can include but is not restricted to a chemotherapeutic or anti-angiogenic agent that limits the growth of the malignant or aggressive tumor beyond or outside its current or natural confines.

Another embodiment can include but is not restricted to a scaffold or holding structure or slow dissolving or time release substance that can include but is not restricted to a lattices or crystals that can be injected percutaneously adjacent to or within a lesion or tumor and the crystals or lattices can contain medications to treat the medical malady or adenoma or lesion or tumor through the slow release of the compound. In one embodiment the medication can be placed in the healthy tissue adjacent to the lesion or malignant or aggressive tumor and as the lesion or tumor attempts to grow the lesion or tumor encounters the lattice and treating or suppressing or activating medication that can include but is not restricted to a chemotherapeutic or anti-angiogenic agent that limits the growth of the lesion or tumor beyond or outside its current or natural confines Peptide and Biological Conversion Therapies can include but are not restricted to the following.

In another embodiment substances or peptides or peptide analogs to include but not restricted to portions of the parathyroid molecule which can include the active portion of the molecule. Molecule or minerals such as Calcium or organic or inorganic compounds that can bind to receptors such as sestimibi, Sensapar (cinacalcet) or Calcium analog compounds that are related to the parathyroid receptors can be used for the parathyroid binding receptors and can utilize methods for reversible or irreversible attachment.

Biological compounds that simulate Parathyroid gland hormone or its precursors or calcium, Sensapar (cinacalcet) or sestimibi related compounds or compound that do not egress the parathyroid can be constructed with biological or chemical denaturing agents or lytic qualities or tissue destructive qualities can be injected percutaneously into the parathyroid and create Parathyroid gland cell death. These compounds or substances can include biological agents that bind to cellular elements to include but not restricted to cell membranes, nucleus, mitochondria, DNA, RNA, parathyroid hormone or its precursors, or other cellular structures or cellular products. This can include but is not restricted to acetylation with carboxylic acid, formic, acetic, benzoic or other acids and can include toxic materials such as thalidomide or arsenic. For peptide modification this can include but is not restricted to modification at the C-end or the N component of the peptide.

MR and RF and Magnetic External Heating Therapies can include but are not restricted to the following.

In one embodiment ferromagnetic particles can percutaneously be placed into the Parathyroid gland and the MRI machine sequences can then be engaged. If Electromagnetic and mechanical and Radiofrequency Excitation (RF) and SAR (heat depositing sequences) are used then the ferromagnetic particles will heat up and can reach temperatures that can be modulated to reach greater than 46 degrees C. Also there will be movement of the ferromagnetic particles that will create Brownian motion or mechanical movement of the particles that will mechanically damage the Parathyroid gland cells. The size of the ferromagnetic particles can be microscopic and as small as particles that are angstroms or nanometers to particles that are macroscopic and in the order of size from micrometers to millimeters. These ferromagnetic particles can be in the solid, liquid, gel or gaseous states or can form a slurry or a mixture or combination of the solid, liquid, gel or gaseous states.

Hyperthermia with Adjuvant Therapy can include but is not restricted to the following.

In another embodiment, non-ferromagnetic substances can be injected into the Parathyroid gland and the natural heating of the MRI from the Electromagnetic and mechanical and RF and SAR (heat depositing sequences) are utilized and focused in the region of the Parathyroid gland then the target tissue, specifically the Parathyroid gland can experience heating that damages the Parathyroid gland.

Another concept is to lower the boiling point of a substance such that the substance is injected into the target tissue and then a hyperthermic source is administered to the target such as the Parathyroid gland and the amount of heat that is needed to damage the target tissue because of the presence of the adjuvant substance which can include but is not restricted to a solid or liquid or gel or gas is a temperature that creates minimal or no damage to the adjacent tissue. In another embodiment the a substance can be injected adjacent to the target tissue that can keep the target tissue safe from the effects of hyperthermia.

In one embodiment water or saline can be percutaneously injected into the target tissue, the Parathyroid gland and the heating by the MRI RF will heat the tissue of the Parathyroid gland and destroy the gland. In another example a substance which can include but is not restricted to a solid or liquid or gel or gas with a boiling point lower that water can be injected and the MRI or external RF can be focused onto the Parathyroid gland. At one atmosphere some of the compounds with boiling points lower than water that can be injected include but are not restricted to Acetaldehyde CH3CHO, Acetone CH3COCH3, Acetylene, Alcohol— ethyl (grain, ethanol) C2H5OH, Ammonia, Benzene (Benzol) C6H6, Bromine, Carbon bisulfide, Carbon dioxide, Carbon disulfide CS2, Carbon tetrachloride CCl4, Chloroform, Cyclohexane, Diethyl ether, Ether, Ethanol, Ethyl acetate CH3COOC2H3, Ethyl bromide C2H3Br, Hexane-n, Hydrogen, Methanol (methyl alcohol, wood alcohol), Methyl acetate, Propane, and Propylene. The heating of the target tissue, the Parathyroid gland, can include but is not restricted to external sources as with MRI RF or HIFU or percutaneous or internal body sources such as but not restricted to RF and microwave. The internal source of heating can be within the target tissue or in the vicinity or adjacent to the target tissue.

In another embodiment the desired goal may be to expose the target tissue probes or delivery systems and adjuvant substances that exceed the boiling point of water. This is more likely to cause damage to the biological tissue. Some examples of injected substances can include saline water, glycerin, and ethyl bromide.

In another embodiment the flashpoint can be used to treat the target tissue such as but not restricted to the Parathyroid gland, which can be injected with a substance which can include but is not restricted to a solid or liquid or gel or gas and when heated will attain a flashpoint at or below a temperature that does not damage tissue adjacent to the target tissue such as but not restricted to the Parathyroid gland. Substances with low flashpoints that are still in the safe range for adjacent biological tissue can include but are not restricted to ethanol.

Hypothermia with Adjuvant Therapy can include but is not restricted to the following.

In another embodiment the concept is to inject a substance that can include a solid, a liquid, a gel or a gas that can lower the freezing point above that of water (e.g. substance and tissue freezes at 10 degrees C. rather than 0 degrees C. as occurs with water) such that the substance is injected into the target tissue and then a hypothermic therapy is administered to the target tissue such as the Parathyroid gland and the amount of cold that is needed to damage the target tissue because of the presence of the adjuvant substance is a temperature that creates minimal or no damage to the adjacent tissue. In another embodiment a substance can be injected adjacent to the target tissue that can keep the target tissue safe from the effects of hypothermia.

In one embodiment water or saline can be percutaneously injected into the target tissue, the Parathyroid gland and cooling or freezing by cryotherapy and hypothermia of the tissue of the Parathyroid gland will destroy the gland. In another example a substance with a freezing point higher that water can be injected into the targeted tissue and the cryotherapy can be focused onto or placed into the Parathyroid gland. At one atmosphere some of the compounds with freezing points higher than water that can be injected include but are not restricted to Helium, Hydrogen, neon, fluorine, oxygen, nitrogen, Argon Chlorine, Bromine, acetic acid, benzene, and phenol.

In another embodiment the desired goal may be to be lower than freezing point of water. This is more likely to cause damage to the biological tissue. Some examples of injected substances can include but are not restricted to ethanol and water and glycerol.

Local protective therapy in the Vicinity of the Target Organ Therapy can include but is not restricted to the following.

Multiple examples have been given of local protective therapies around the target tissue.

Examples can include but are not restricted to, one example in which hyperthermia is applied to the target tissue and the tissue adjacent to the targeted tissue can be bathed in 5% or greater Dextrose Water.

In one example a toxic material injected into the target tissue such as the Parathyroid gland will be a material where the optimal injected material will yield low or no toxicity to the local biological tissue when the local biological tissue is not the target. If the local non-target tissue is diluted or given an antidote material or if it is heated to a safe level the local tissue will remain safe even if the toxic material leaks out of the Parathyroid gland it will have minimal negative biological effects such as but not restricted to injection of ammonia into the Parathyroid gland but injection of saline into adjacent tissue; heating of local tissue to less than cytotoxic levels of heat while the Parathyroid gland at the same heat levels will experience cytotoxicity because it received an adjuvant substance. These injected substances can be in the solid, liquid, gel or gaseous states or can form a slurry or a mixture or combination of the solid, liquid, gel or gaseous states and can include ferromagnetic substances, saline, water, ammonia, bromine, carbon dioxide, carbon disulfide.

In another embodiment if hypothermia or cryothermia are used, then the local environment in the vicinity of the target tissue, which can include but is not restricted to the Parathyroid gland, can be infused with solutions or substances that depress the freezing point such as but not restricted to sorbitol, glycerol, glycogen, glucose, sodium chloride or substances with increased molality compared to water. These can also include supersaturated solutions or combinations of these substances.

Mechanical Ablation Therapy can include but is not restricted to the following.

In another embodiment a percutaneous technique can include placing a needle into the target tissue, such as but not restricted to the Parathyroid gland. This can include but is not restricted to a mechanical cutting or ablating or cutting tool or cell maceration and tissue damaging device. The mechanism of mechanical damage can include but is not restricted to a blade, a needle, a burr, a compressive force, a stream or flow of focused material to include a solid or liquid or a gas or gel to include water, oxygen, a hydrogel or hot metal or liquid nitrogen.

Methods of delivering the mechanical force can include but are not restricted to a needle with one or more end-holes, side-holes, or combination of these end and side holes and a cutting device that can include a blade, a needle, a burr, a compressive force, a rotating force, a stream or flow of focused material to include a solid or liquid or a gas or gel to include water, oxygen, a hydrogel or hot metal or liquid nitrogen.

Negative suction that is continuous or pulsed can remove tissue that enters the core of the needle.

Suction and Expansion Therapy can include but is not restricted to the following.

In another embodiment a percutaneous technique can include placing a hollow needle or catheter or guide that lies within or intimately adjacent to the target tissue, such as but not restricted to the Parathyroid gland. Negative pressure can be applied within the needle hollow needle or catheter or guide such that the blood flow to the parathyroid gland is inhibited and or ceases and thus creates an ischemic state within the parathyroid tissue and thus results in cell death and cytolysis.

This negative pressure can be combined with a cutting tool that can include a side-hole in the needle and a cutting or mechanical device that can include a burr or a blade that can remove tissue that enters the core of the needle. The needle or guide or catheter can have one or more channels and each channel can be dedicated to the same or different tasks.

Positive Pressure and Expansion Therapy can include but is not restricted to the following.

In another embodiment a percutaneous technique can include placing a needle into the target tissue, such as but not restricted to the Parathyroid gland. Positive pressure can be applied within the needle. This will create positive pressure within the target tissue such as but not restricted to the Parathyroid gland. To create the positive pressure a substance can include but is not restricted to a solid, liquid, gel or gas or a combination can form a slurry or a mixture or combination of the solid, liquid, gel or gaseous states can be instilled though the needle into the target tissue. The objective is to create enough positive pressure within the tissue of the Parathyroid gland to exceed systolic pressure and prevent the inflow of blood into the parathyroid gland and secondarily create ischemia within the Parathyroid. In one embodiment this supra-systolic pressure, pressure above systole in the target tissue, will be maintained until the target tissue ischemia is sufficient to achieve cytolysis and target tissue cell death.

This positive pressure can be combined with a cutting tool that can include a side-hole in the needle and a cutting device or mechanical device that can include a burr or a blade that can remove tissue that enters the core of the needle. The needle or guide or catheter can have one or more channels and each channel can be dedicated to the same or different tasks.

Combinations of Therapies can include but are not restricted to the following.

Therapies can be used in isolation or in combination. Multiple therapies can be combined such as but not restricted to hyperthermia with adjuvant therapy and MR heating with ferromagnetic or HIFU with adjuvant therapy and local protective therapy.

A Nerve Sensory Device can include but is not restricted to the following.

Prior to the procedure a nerve stimulator can be activated then the therapeutic needle tip or guide or probe is positioned and prior to therapeutic treatment, the stimulator is designed to determine whether the local nerves adjacent or near to the Parathyroid gland including but not restricted to the Laryngeal nerves, the Recurrent Laryngeal nerves and the Sympathetic and parasympathetic nerves as well as other visceral and pain nerves will be affected by the treatment. In one example a low voltage stimulation can be applied with a lesion generator (e.g. 0.1-0.2 V at 50 Hz, RFG-3CF, Radionics, Burlington Mass) to insure that the adjacent an critical nerves are not stimulated. Motor stimulation can be applied to the region (e.g. 0.1-0.2 V at 2 Hz).

Monitoring of laryngeal nerves can also be monitored using standard forms of intraoperative laryngeal and laryngeal nerve monitoring and Intraoperative EMG.

Temperature probes can be utilized to assess the local tissue environment by percutaneous insertion of a probe or temperature measuring device. Said measuring device can have the capacity to turn off the treatment generator and discontinue or limit or modulate treatment. The probe can also be located in or on or adjacent to the trachea, larynx and airway.

In another embodiment another form of sensory probe can be a device that senses electromagnetic signals to include but not restricted to electric current. These can include but are not restricted to modifications of Hall sensors with field concentrators, AMR current sensors, magneto-optical and superconducting current sensors, Hall effect IC sensor, Resistor, whose voltage is directly proportional to the current through it, Fiber optic current sensor, using an interferometer to measure the phase change in the light produced by a magnetic field, Rogowski coil, electrical device for measuring alternating current (AC) or high speed current pulses, a galvanometer is a type of ammeter: an instrument for detecting and measuring electric current and an electrometer is an electrical instrument for measuring electric charge or electrical potential difference. The sensory probe can be placed in the vicinity of the target tissue and in the case of the Parathyroid gland can be place adjacent or near the Parathyroid gland specifically near the neural structures such as the laryngeal nerves or major blood vessels.

Needles or percutaneous penetrating cylinder or solid or hollow tube device can include but is not restricted to the following.

In another embodiment includes a needle or probe or percutaneous cylinder or tube (which can be hollow or solid) device (all can be referred to here as a needle) that can be composed of a metallic substance that can include but is not restricted to stainless steel, aluminum, iron, titanium or other ferrous materials and alloy.

A device that penetrates the skin or passes through human tissue can be but is not restricted to a needle or probe or tines or percutaneous tube device and hereafter will be referred to as a needle. The needle can be made to consist of fully or partially of optimal insulating materials or can be insulated with a material on the outside portion of the needle, on the inside portion of the needle if the needle is hollow, a combination of inside and outside of the needle, the needle can be composed of multiple metallic and non-metallic materials to include but not restricted to good insulators and poor conductors of heat and can also be composed of materials that can include but are not restricted to ceramic materials, high aluminum ceramics (Alumina Ceramic), beryllium, fiberglass, Zirconium, High Zirconium, adhesives and nansulators, reinforced carbon-carbon fiber construction (aka carbon-carbon, abbreviated C/C), which is a composite material consisting of carbon fiber reinforcement in a matrix of graphite, Carbon fiber-reinforced silicon carbide (C/SiC), which is a development of pure carbon-carbon (C/SiC utilizes silicon carbide with carbon fiber, and this compound is thought to be more durable than pure carbon-carbon), Fibrous refractory composite insulation (FRCI), LI-900 silica tiles, made from essentially very pure quartz sand, High-temperature reusable surface insulation (HRSI), Reaction Cured Glass (RCG) of which tetrasilicide and borosilicate glass are some of several ingredients to waterproof the coating dimethylethoxysilane and are injected into the coating (densifying the tile with tetraethyl orthosilicate (TEOS) also helps to protect the silica and waterproof), RCC (a laminated composite material made from graphite rayon cloth and impregnated with a phenolic resin). After curing at high temperature in an autoclave, the laminate is pyrolyzed to convert the resin to carbon. This is then impregnated with furfural alcohol in a vacuum chamber, then cured and pyrolyzed again to convert the furfural alcohol to carbon. This process is repeated three times until the desired carbon-carbon properties are achieved and the outer layers of the RCC are converted to silicon carbide. The silicon-carbide coating protects the carbon-carbon from oxidation.

In one embodiment the needle can contain a diamond or zirconium tip.

The needle with chambers can circulate substances to form a heat sink, which can include are but not restricted to solids, liquids and gels and gasses or a vacuum. These substances can include but are not restricted to water, argon, nitrogen, and nitrous oxide or a vacuum.

In another embodiment the needle have chambers that contain substances or a vacuum that are non-circulating.

These needles can be used for additional applications where insulation is not a requirement.

In another embodiment the needle can be coated or composed with a nansulatecoating which can include but is not restricted to an insulation technology that incorporates a nanocomposite called Hydro-NM-Oxide, a product of nano-technology. This material is documented as having one of the lowest measured thermal conductivity values. (0.017 W/mK). Nansulate, when fully cured, contains approximately 70% Hydro-NM-Oxide and 30% acrylic resin and performance additive. It does not function as a metallic UV radiator (reflection). The nano-particles in Nansulate act to inhibit the heat flow much like traditional insulation.

In another embodiment the needle can have but is not restricted to an outer or inner coating that provides for decreased resistance or decreased friction from the tissue through which it penetrates. This can include but is not restricted to a coating or composition that can include but is not restricted to a Polytetrafluoroethylene (PTFE) or fluoropolymer of tetrafluoroethylene or a hypophillic or hydrophobic material, ultra-high-molecular-weight polyethylene (UHMWPE) or mineral oil or molybdenum disulfide embedded as additional lubricants in the needles matrix.

In another embodiment the needle can have but is not restricted to a variable or non-uniform flexibility and tensile strength within its length or width.

In another embodiment the needle can have but is not restricted to a variable width of its wall or lumen. In one example the wall can be thicker proximally than distally such that the needle or catheter has the configuration of a triangle or arrowhead that allows for easier penetration.

In another embodiment the needle can have but is not restricted to a chamber that can be filled with a substance that can include a solid or liquid or gel or gas that can be filled to include but not restricted to it being under pressure and causing the needle or catheter wall to harden or become more firm such that it can pierce the skin more easily. Once it has reached its target the chamber material can be withdrawn fully or incompletely or the nature of the material can be altered. In an example the catheter or needle chamber can be a nitinol or alloy metal that when cooled is firm but when heated is soft and pliable and flexible.

In another embodiment the needle can be composed of but not restricted to a material to include but not restricted to material such as nitinol or alloy metal that when cooled is firm but when heated is soft and pliable and flexible or other materials that have variable hardness or softness under differing thermal conditions such as hot or cold, or electromagnetic conditions such as UV light or the presence or absence of an electric current of a magnetic force to include but not restricted to Ferrofluids such as colloidal liquids made of nanoscale ferromagnetic, or ferrimagnetic, particles suspended in a carrier fluid such as an organic solvent or water, magnetorheological fluids (MR fluids), nanoelectromechanical systems; magnetorheological fluid (MRF) refers to liquids similar to ferrofluids (FF) that solidify in the presence of a magnetic field. These materials can contain and include but are not restricted to material that contain magnetite, hematite or some other compound containing iron that are small enough for thermal agitation to disperse them evenly within a carrier fluid, and for them to contribute to the overall magnetic response of the fluid and can include but is not restricted to the composition of a typical ferrofluid at about 5% magnetic solids, 10% surfactant and 85% carrier, by volume. In other embodiments the ferromagnetic particles can be arranged in a manner that can be circular or spiral or other geometric or non-geometric arrangements that can alter or vary the shape or firmness or flexibility of the needle.

One of the uses for this type of needle can include but is not restricted to serving as a rigid penetrating device to reach the target tissue as it penetrates the skin or organs or vessels but then can become flexible and not damage the tissue any further when it is changes to a non-rigid device.

The variable stiffness can include all or only one or more portions of the needle.

The needle can include multiple configurations and its cross section can include a geometric or non-geometric or variable configuration that can include but is not restricted to a curved or circle, or ellipse configuration or an angled or straight or, triangle, rectangle, pentagon, hexagon etc., configuration.

A stylet or guide or introducers can include but are not restricted to the following.

The stylet or guide or introducer in the preferred embodiment can include but is not restricted to a device that can be placed within the inside hollow of device such as but not restricted to a needle or catheter or it can be placed on the outside of a needle or catheter. Some of the functions of the stylet or guide or introducer can include but are not restricted to stiffening the path, protecting, guiding, introducing, or filling the hollow of the device or needle or catheter or any combination of uses.

In another embodiment is a stylet or guide or introducer or probe or percutaneous cylinder or tube (which can be hollow or solid) device that can be composed of a metallic substance that can include but is not restricted to stainless steel, aluminum, iron, titanium or other ferrous materials and alloy.

A device that penetrates the skin or passes through human tissue and stiffening the path, protecting, guiding, introducing, or filling the hollow of the device or needle or catheter or any combination of uses but not restricted to these uses and can be but is not restricted to a stylet or guide or introducer or probe or tines or percutaneous tube device and hereafter will be referred to as a stylet or guide or introducer. The stylet or guide or introducer can be made to consist of fully or partially of optimal insulating materials or can be insulated with a material on the outside portion of the stylet or guide or introducer, on the inside portion of the stylet or guide or introducer if the stylet or guide or introducer is hollow, a combination of inside and outside of the stylet or guide or introducer, the stylet or guide or introducer can be composed of multiple metallic and non-metallic materials to include but not restricted to good insulators and poor conductors of heat and can also be composed of materials that can include but are not restricted to ceramic materials, high aluminum ceramics (Alumina Ceramic), beryllium, fiberglass, Zirconium, High Zirconium, adhesives and nansulators, reinforced carbon-carbon fiber construction (aka carbon-carbon, abbreviated C/C), which is a composite material consisting of carbon fiber reinforcement in a matrix of graphite, Carbon fiber-reinforced silicon carbide (C/SiC), which is a development of pure carbon-carbon (C/SiC utilizes silicon carbide with carbon fiber, and this compound is thought to be more durable than pure carbon-carbon), Fibrous refractory composite insulation (FRCI), LI-900 silica tiles, made from essentially very pure quartz sand, High-temperature reusable surface insulation (HRSI), Reaction Cured Glass (RCG) of which tetrasilicide and borosilicate glass are some of several ingredients to waterproof the coating dimethylethoxysilane and are injected into the coating (densifying the tile with tetraethyl orthosilicate (TEOS) also helps to protect the silica and waterproof), RCC (a laminated composite material made from graphite rayon cloth and impregnated with a phenolic resin). After curing at high temperature in an autoclave, the laminate is pyrolyzed to convert the resin to carbon. This is then impregnated with furfural alcohol in a vacuum chamber, then cured and pyrolyzed again to convert the furfural alcohol to carbon. This process is repeated three times until the desired carbon-carbon properties are achieved and the outer layers of the RCC are converted to silicon carbide. The silicon-carbide coating protects the carbon-carbon from oxidation.

In one embodiment the stylet or guide or introducer can contain a diamond or zirconium tip.

Stylet or guide or introducer with chambers that can circulate substances to form a heat sink can include are but not restricted to solids, liquids and gels and gasses or a vacuum. These can substances can include but are not restricted to water, argon, nitrogen, and nitrous oxide or a vacuum.

In another embodiment the stylet or guide or introducer have chambers that contain substances or vacuum that are non-circulating.

The stylet or guide or introducer can be used for additional applications where insulation is not a requirement.

In another embodiment the stylet or guide or introducer can be coated or composed with a nansulatecoating which can include but is not restricted to an insulation technology that incorporates a nanocomposite called Hydro-NM-Oxide, a product of nanotechnology. This material is documented as having one of the lowest measured thermal conductivity values. (0.017 W/mK). Nansulate, when fully cured, contains approximately 70% Hydro-NM-Oxide and 30% acrylic resin and performance additive. It does not function as a metallic UV radiator (reflection). The nano-particles in Nansulate act to inhibit the heat flow much like traditional insulation.

In another embodiment the stylet or guide or introducer can have but is not restricted to an outer or inner coating that provides for decreased resistance or decreased friction from the tissue through which it penetrates. This can include but is not restricted to a coating or composition that can include but is not restricted to a Polytetrafluoroethylene (PTFE) or fluoropolymer of tetrafluoroethylene or a hypophillic or hydrophobic material, ultra-high-molecular-weight polyethylene (UHMWPE) or mineral oil or molybdenum disulfide embedded as additional lubricants in the stylet or guide or introducers matrix.

In another embodiment the stylet or guide or introducer can have but is not restricted to a variable or non-uniform flexibility and tensile strength within its length or width.

In another embodiment the stylet or guide or introducer can have but is not restricted to a variable width of its wall or lumen. In one example the wall can be thicker proximally than distally such that the stylet or guide or introducer or catheter has the configuration of a triangle or arrowhead that allows for easier penetration.

In another embodiment the stylet or guide or introducer can have but is not restricted to a chamber that can be filled with a substance that can include a solid or liquid or gel or gas that can be filled to include but not restricted to it being under pressure and causing the stylet or guide or introducer or catheter wall to harden or become more firm such that it can pierce the skin more easily. Once it has reached its target the chamber material can be withdrawn fully or incompletely or the nature of the material can be altered. In one example the catheter or stylet or guide or introducer chamber can be a nitinol or alloy metal that when cooled is firm but when heated is soft and pliable and flexible.

In another embodiment the stylet or guide or introducer can be composed of but not restricted to a material to include but not restricted to material such as nitinol or alloy metal that when cooled is firm but when heated is soft and pliable and flexible or other materials that have variable hardness or softness under differing thermal conditions such as hot or cold, or electromagnetic conditions such as UV light or the presence or absence of an electric current of a magnetic force to include but not restricted to Ferrofluids such as colloidal liquids made of nanoscale ferromagnetic, or ferri-magnetic, particles suspended in a carrier fluid such as an organic solvent or water, magnetorheological fluids (MR fluids), nanoelectromechanical systems; magnetorheologi-cal fluid (MRF) refers to liquids similar to ferrofluids (FF) that solidify in the presence of a magnetic field. These materials can contain and include but are not restricted to material that contain magnetite, hematite or some other compound containing iron that are small enough for thermal agitation to disperse them evenly within a carrier fluid, and for them to contribute to the overall magnetic response of the fluid and can include but is not restricted to the composition of a typical ferrofluid at about 5% magnetic solids, 10% surfactant and 85% carrier, by volume. In other embodi-ments the ferromagnetic particles can be arranged in a manner that can be circular or spiral or other geometric or non-geometric arrangements that can alter or vary the shape or firmness or flexibility of the stylet or guide or introducer.

One of the uses for this type of stylet or guide or introducer can include but is not restricted to serving as a rigid penetrating device to reach the target tissue as it penetrates the skin or organs or vessels but then can become flexible and not damage the tissue any further when it is changes to a non-rigid device.

The variable stiffness can include all or only one or more portions of the stylet or guide or introducer.

The stylet or guide or introducer can include multiple configurations and its cross section can include a geometric or non-geometric or variable configuration that can include but is not restricted to a curved or circle, or ellipse configu-ration or an angled or straight or, triangle, rectangle, penta-gon, hexagon etc., configuration.

A catheter can include but is not restricted to the follow-ing.

A catheter can be include but is not restricted to a solid or hollow cylinder or tube device for use with but not restricted to percutaneous or transcutaneous or filling or being trans-mitted or transported in or within or through a hollow viscous or vascular structure or an organic or inorganic structure within or outside of the body.

In another embodiment a catheter can be composed of a non-metallic substance such as but not restricted to rubber, or plastic or latex or cloth, carbon fibers or carbon-carbon fibers or a metallic substance that can include but is not restricted to stainless steel, aluminum, iron, titanium or other ferrous materials and alloy or any combination of these materials.

A catheter can be used for but not restricted to the transportation of substances such as but not restricted to solids or liquids or gels or gases and can penetrate the skin or pass through human tissue or transport within human tissue to include but not restricted to a hollow viscous stricture that can include but is not restricted to the esopha-gus, small and large intestine, stomach, colon, rectum, mouth, trachea, biliary ducts and nostrils or vascular struc-ture that can include arteries and veins and lymphatics, or can stiffen the path, protect, guide, introduce, or fill the hollow of a device or needle or another catheter or any combination of uses but is not restricted to these uses.

The catheter can be made to consist of fully or partially of optimal insulating materials or can be insulated with a material on the outside portion of the stylet or guide or introducer, on the inside portion of the catheter if the catheter is hollow, a combination of inside and outside of the stylet or guide or introducer, the catheter can be composed of multiple metallic and non-metallic materials to include but are not restricted to good insulators and poor conductors of heat and can also be composed of materials that can include but are not restricted to ceramic materials, high aluminum ceramics (Alumina Ceramic), beryllium, fiber-glass, Zirconium, High Zirconium, adhesives and nansula-tors, reinforced carbon-carbon fiber construction (aka car-bon-carbon, abbreviated C/C), which is a composite material consisting of carbon fiber reinforcement in a matrix of graphite, Carbon fiber-reinforced silicon carbide (C/SiC), which is a development of pure carbon-carbon (C/SiC utilizes silicon carbide with carbon fiber, and this compound is thought to be more durable than pure carbon-carbon), Fibrous refractory composite insulation (FRCI), LI-900 silica tiles, made from essentially very pure quartz sand, High-temperature reusable surface insulation (HRSI), Reac-tion Cured Glass (RCG) of which tetrasilicide and borosili-cate glass are some of several ingredients to waterproof the coating dimethylethoxysilane and are injected into the coat-ing (densifying the tile with tetraethyl orthosilicate (TEOS) also helps to protect the silica and waterproof), RCC (a laminated composite material made from graphite rayon cloth and impregnated with a phenolic resin). After curing at high temperature in an autoclave, the laminate is pyrolyzed to convert the resin to carbon. This is then impregnated with furfural alcohol in a vacuum chamber, then cured and pyrolyzed again to convert the furfural alcohol to carbon. This process is repeated three times until the desired carbon-carbon properties are achieved and the outer layers of the RCC are converted to silicon carbide. The silicon-carbide coating protects the carbon-carbon from oxidation.

In one embodiment the catheter can contain a diamond or zirconium tip.

Catheter with chambers that can circulate substances to form a heat sink can include are but not restricted to solids, liquids and gels and gasses or a vacuum. These substances can include but are not restricted to water, argon, nitrogen, and nitrous oxide or a vacuum.

In another embodiment the catheter can have chambers that contain substances or a vacuum that are non-circulating.

The catheter can be used for additional applications where insulation is not a requirement.

In another embodiment the catheter can be coated or composed with a nansulatecoating which can include but is not restricted to an insulation technology that incorporates a nanocomposite called Hydro-NM-Oxide, a product of nano-technology. This material is documented as having one of the lowest measured thermal conductivity values. (0.017 W/mK). Nansulate, when fully cured, contains approxi-mately 70% Hydro-NM-Oxide and 30% acrylic resin and performance additive. It does not function as a metallic UV radiator (reflection). The nano-particles in Nansulate act to inhibit the heat flow much like traditional insulation.

In another embodiment the catheter can have but is not restricted to an outer or inner coating that provides for decreased resistance or decreased friction from the tissue through which it penetrates. This can include but is not restricted to a coating or composition that can include but is not restricted to a Polytetrafluoroethylene (PTFE) or fluo-ropolymer of tetrafluoroethylene or a hypophillic or hydro-phobic material, ultra-high-molecular-weight polyethylene (UHMWPE) or mineral oil or molybdenum disulfide embed-ded as additional lubricants in the stylet or guide or intro-ducers matrix.

In another embodiment the catheter can have but is not restricted to a variable or non-uniform flexibility and tensile strength within its length or width.

In another embodiment the catheter can have but is not restricted to a variable width of its wall or lumen. In one example the wall can be thicker proximally than distally such that the catheter or catheter has the configuration of a triangle or arrowhead that allows for easier penetration.

In another embodiment the catheter can have but is not restricted to a chamber that can be filled with a substance that can include a solid or liquid or gel or gas that can be filled to include but not restricted to it being under pressure and causing the catheter or catheter wall to harden or become more firm such that it can pierce the skin more easily. Once it has reached its target the chamber material can be withdrawn fully or incompletely or the nature of the material can be altered. In one example the catheter or catheter chamber can be a nitinol or alloy metal that when cooled is firm but when heated is soft and pliable and flexible.

In another embodiment the catheter can be composed of but not restricted to a material to include but not restricted to material such as nitinol or alloy metal that when cooled is firm but when heated is soft and pliable and flexible and other materials that have variable hardness or softness under differing thermal conditions such as hot or cold, or electromagnetic conditions such as UV light or the presence or absence of an electric current of a magnetic force to include but not restricted to Ferrofluids such as colloidal liquids made of nanoscale ferromagnetic, or ferrimagnetic, particles suspended in a carrier fluid such as an organic solvent or water, magnetorheological fluids (MR fluids), nanoelectromechanical systems, magnetorheological fluid (MRF) refers to liquids similar to ferrofluids (FF) that solidify in the presence of a magnetic field. These materials can contain and include but are not restricted to material that contain magnetite, hematite or some other compound containing iron that are small enough for thermal agitation to disperse them evenly within a carrier fluid, and for them to contribute to the overall magnetic response of the fluid and can include but are not restricted to the composition of a typical ferrofluid at about 5% magnetic solids, 10% surfactant and 85% carrier, by volume. In other embodiments the ferromagnetic particles can be arranged in a manner that can be circular or spiral or other geometric or non-geometric arrangements that can alter or vary the shape or firmness or flexibility of the stylet or guide or introducer.

One of the uses for this type of catheter can include but is not restricted to serving as a rigid penetrating device to reach the target tissue as it penetrates the skin or organs or vessels but then can become flexible and not damage the tissue any further when it is changes to a non-rigid device.

The variable stiffness can include all or only one or more portions of the stylet or guide or introducer.

The catheter can include multiple configurations, and its cross section can include a geometric or non-geometric or variable configuration that can include but is not restricted to a curved or circle, or ellipse configuration or an angled or straight or, triangle, rectangle, pentagon, hexagon etc, configuration.

A combined Hyper and Hypothermic Device can include but is not restricted to the following.

In another embodiment a Hyper and Hypothermic devices can be coupled to control the heating and cooling of tissue. In addition, the forces and architecture responsible for cell death differ and the forces and architecture resistant to cell death differ.

In one embodiment alternating heating and cooling can create a synergy that can decrease both the temperature and duration required for hyper and hypothermia which can prove beneficial to the adjacent non-targeted tissue thus preserving the living tissue in the vicinity of the targeted tissue, which can include but is not restricted to the Parathyroid gland being the targeted tissue and the neural and vascular structures adjacent to the Parathyroid gland being spared.

Markers and Localization Devices and Wires and filaments can include but are not restricted to the following.

Currently surgeons that remove Parathyroid gland adenomas rely on pre-surgical imaging to approximate the location of the parathyroid gland. Markers can be placed onto the skin but with flexion and extension of the neck the location of the Parathyroid gland can move deeper within the neck relative to the skin surface. This flexion and extension occurs during anesthetic intubation and can vary from the position that is used for diagnostic imaging and localization and skin marker placement.

Methods for marking and localizing the Parathyroid gland can prove useful. In one embodiment the Parathyroid gland to be removed can be percutaneously injected into the Parathyroid gland with a marking material that can include but is not restricted to a solid or liquid or gel or gas such as but not restricted to methylene blue and gentian violet, tattoo inks, fluorescent light or UV sensitive dyes which can include but are not restricted to nanoparticles to include but are not restricted to Sol-gel derived silica, which is an excellent host material for creating fluorescent nanoparticles by the inclusion of covalently-bound organic dyes, Fluorophores that can be organic or inorganic, Fluorite (also called fluorspar), which is a halide mineral composed of calcium fluoride, $CaF2$. Gemstones, minerals, may have a distinctive fluorescence or may fluoresce differently under short-wave ultraviolet, long-wave ultraviolet, or X-rays, calcite and amber will fluoresce under shortwave UV. Rubies, emeralds, and the Hope Diamond exhibit red fluorescence under short-wave UV light; diamonds also emit light under X ray radiation, Vitamin B2 (fluoresces yellow), quinine (blue), ninhydrin, and fluorescein.

In another embodiment the injected material can be metal radio-opaque and can be viewed with x-ray and can include but is not restricted to calcium, iodine, iron and other metals such as titanium, tungsten, barium sulfate, and zirconium oxide.

In another embodiment the marker or localizing device or substance can be a radioactive material that is low dose and used for diagnostic radiology that can include but is not restricted to technetium 99m, Iodine 123 and Iodine131 or Sestamibi99mTc, which can be percutaneously injected directly into the Parathyroid gland. A percutaneous injection would have the advantage over intravenous sestamibi because of the lack of background counts in organs other than the Parathyroid gland such as the thyroid and fatty tissue and muscles. A radiation sensitive probe such as a pencil probe can be used to locate the Parathyroid gland during surgery more easily.

The markers and localization devices can contain a GPS device or contain a material that emits or provides for GPS detection.

To place the marker or localizing device a guide/wire/placement device, a stylet or a tube or needle or a hollow or solid tube can be used to place the marker or localizing device in the target tissue, parathyroid. In one embodiment the marker or localizing device can contain a transitional zone that contains a transitional state sensitive substance that can be converted from a solid or liquid/gel material that when exposed to a substance or an energy source such as but not restricted to electromagnetic energy, kinetic or mechanical or thermal energy or forces changes its state and can separate from the a more solid or gel state to a state where the placement device is separated from the marker or localizing device. In one embodiment the placement material and the transitional material and the marker or localizing device can all be metallic and if energy such as an electrical current or a thermal force is transmitted though the placement wire the transitional zone will separate from the marker or localizing device. In another embodiment the placement device material can be composed of a phase transitional gel that when cold remains solid but when heated the transitional zone will melt or dissolve after a given period of time and separate from the marker or localizing device. In another embodiment phase transitional gels or other materials that can alter the physical state of the gel. Solvents can be used to alter the physical state of the material.

The placement device can have grooves/threads that when turned or moved in the proper manner that will release/unthread. In one embodiment the gel can take on crystalline characteristics and become more rigid or less rigid when exposed to electromechanical or kinetic or mechanical energy such as liquid crystal (LC) gels with a radial or twisted-radial molecular orientation that are fabricated using a radial electric field generated by an indium-tin-oxide hole electrode in the bottom substrate. If the top substrate is not buffed, the radial-type LC gel is formed which can convert linearly polarized light into axially polarized light. On the other hand, if the top substrate is homogeneously buffed, then a twisted-radial LC gel is produced which can convert linearly polarized light into radially polarized light. These polarization converters are useful for diffractive optics and optical imaging systems.

The placement device can be a tube, which is hollow and can transport a filament that can be organic and include but not be restricted to silk or cotton or hemp or can be inorganic and can be composed or synthetic polymers such as but not restricted to nylon, rayon, or a carbon or carbon-carbon synthetic filament or a metallic filament. The filament should be flexible enough that it does not damage the tissue through which it passes such as but not restricted to the thyroid, fat and skin. The marker or localizing device can then be attached to the filament and put in place percutaneously within the target tissue, the parathyroid gland.

In another embodiment a percutaneous localization device can be used to assist in removing a parathyroid gland. This technique is used commonly in breast localizations but the breast tissue is composed of fat and breast parenchyma and stromal tissue that is predominantly non-vascular. A localization device for the parathyroid will likely have to pass through the thyroid gland, which is highly vascularized. Therefore the guide will have to be both anchored securely to the parathyroid gland and the wire between the parathyroid to the skin will have to be both durable and stout and pliable.

The localizing wire material can include but is not restricted to stainless steel, nitinol, titanium, and other metals and metal alloys that can be both Magnetic Resonance Imaging (MRI) compatible or not MRI compatible, carbon-carbon fibers, organic and inorganic material which can be combined or added to create and maximize flexibility and strength and the localization wire can be composed different segments that can contain one or a combination of materials for each segment.

In one embodiment the wire can be composed with a transitional material that resides between the skin component and the target tissue parathyroid gland such that when heat or an electric current of other electromagnetic or mechanical or kinetic energy or force is administered to the wire the transitional component the two segments detach or disengage, leaving the parathyroid component of the localizing wire separate from the percutaneous skin component.

In one preferred embodiment the wire can be composed of a carbon-carbon matrix that is a segment that is highly flexible and a more rigid segment that can include but is not restricted to a hook or anchor that is embedded into or surrounds a portion or the entirety of the parathyroid gland. These segments can be composed of the same material or different materials or a combination of materials.

The localizing device can include and be composed to include but not restricted to a solid wire, a braided or woven wire. The localizing device and wire and the parathyroid anchoring component can be textured or beaded to increase its detection with ultrasound. The localizing device and wire and anchor can be MRI or CT scan visible. The localizing device can be coated with a material that can provide for improved imaging visualization or for insulation.

The localizing device can be can be oriented and configured from any arc between a 12 o'clock to 12 o'clock full 180 degree arc or rotation, the anchor can consist of one or multiple tines or projections, the localizing device can consist of but is not restricted to a threaded, beaded, barbed, looping, angled, curved spiral or circular or straight structure. In one embodiment the localizing device can be screwed into or out of the target tissue such as the parathyroid gland. In another embodiment the localizing device can be coated with a material that is organic and dissolvable or which can be metabolized by the organism over time and which can also be stripped from the localizing device by a guiding mechanism preferably percutaneous such that when the localizing device is implanted it fixes itself in the target tissue such as the parathyroid gland but if needed the localizing device can be removed by stripping the localizing device or the localizing devices coating material with the guiding mechanism and the stripped material can either be dissolved, metabolized or can be made of an inert material that can be left in the body without significant risk to the organism. Some of the coatings can include but are not restricted to proteins, carbohydrates, fats, minerals, and other organic or inorganic materials.

The localizing device can also be used for treatment if the coating that is stripped from the localizing device is composed of a material that can suppress the function of the target tissue such as the parathyroid gland and can consist of but is not restricted to substances or peptides or peptide analogs to include but not restricted to portions of the parathyroid molecule which can include the active portion of the target tissue hormonal gland such as the parathyroid molecule. For parathyroid function and homeostasis, molecules or minerals such as Calcium or organic or inorganic compounds that can bind to receptors such as Sestamibi, Sensapar (cinacalcet) or Calcium analog compounds that are related to the parathyroid receptors can be used to the parathyroid binding receptors and can utilize methods for reversible or irreversible attachment.

The marker or localization device can contain a GPS device or contain a material that emits or provides for GPS detection.

The marker can include an LED device.

The marker or localizing device can have a shape that will pierce the target tissue but will offer resistance when it is attempted to remove the marker or localizing device. This can include but is not restricted to a corrugated shape, a friction producing shape or a shape where target tissue becomes embedded in the marker. The resistance can be controlled such that it is not engaged or activated until the marker or localizing device lies within the target tissue, parathyroid Hooks One embodiment can include hooks to secure the parathyroid gland and these hooks can be non-heat conducting and insulated or heat conducting. The hooks can include but are not restricted to a curved single or multi-pronged device that can exit a guiding needle or catheter and snap open and can also return into the guiding needle or catheter.

The hook anchor can be can be oriented and configured from any arc between a 12 o'clock to 12 o'clock full 180 degree arc or rotation, the anchor can consist of one or multiple tines or projections, the hook can consist of but is not restricted to a threaded, beaded, barbed, looping, angled, curved spiral or circular or straight structure. In one embodiment the hook can be screwed into or out of the target tissue such as the parathyroid gland. In another embodiment the hook can be coated with a material that is organic and dissolvable or which can be metabolized by the organism over time and which can also be stripped from the hook by a guiding mechanism preferably percutaneously such that when the hook is implanted it fixes itself in the target tissue such as the parathyroid gland but if needed the hook can be removed by stripping the hook or the hooks coating material with the guiding mechanism and the stripped material can either be dissolved, metabolized or can be made of an inert material that can be left in the body without significant risk to the organism. Some of the coatings can include but are not restricted to proteins, carbohydrates, fats, minerals, and other organic or inorganic materials.

Insulating Materials can include but are not restricted to the following.

Insulating materials can be used but are not restricted to the thermal devices, energy delivery, cryo-devices, wires or hooks or localization devices, or needles, or guiding catheters or needles or electrodes or antennas and other therapy devices or assisting devices and can include but are not restricted to vacuums, circulating solids or liquids or gels or gasses, ceramic materials, high aluminum ceramics (Alumina Ceramic), beryllium, fiberglass, Zirconium, High Zirconium, adhesives and nansulators, reinforced carbon-carbon fiber construction (aka carbon-carbon, abbreviated C/C), which is a composite material consisting of carbon fiber reinforcement in a matrix of graphite, Carbon fiber-reinforced silicon carbide (C/SiC), which is a development of pure carbon-carbon (C/SiC utilizes silicon carbide with carbon fiber, and this compound is thought to be more durable than pure carbon-carbon), Fibrous refractory composite insulation (FRCI), LI-900 silica tiles, made from essentially very pure quartz sand, High-temperature reusable surface insulation (HRSI), Reaction Cured Glass (RCG) of which tetrasilicide and borosilicate glass are some of several ingredients to waterproof the coating dimethylethoxysilane and are injected into the coating (densifying the tile with tetraethyl orthosilicate (TEOS) also helps to protect the silica and waterproof), RCC (a laminated composite material made from graphite rayon cloth and impregnated with a phenolic resin). After curing at high temperature in an autoclave, the laminate is pyrolyzed to convert the resin to carbon. This is then impregnated with furfural alcohol in a vacuum chamber, then cured and pyrolyzed again to convert the furfural alcohol to carbon. This process is repeated three times until the desired carbon-carbon properties are achieved and the outer layers of the RCC are converted to silicon carbide. The silicon-carbide coating protects the carbon-carbon from oxidation.

Combination and Multiple Devices can be used and can include but are not restricted to the following.

In another embodiment multiple devices can be combined to include but not restricted to hyperthermic devices, hypothermic devices, mechanical devices, substance delivery such as through a hollow bore needle, sensory feedback devices and local environment therapy delivery.

A Display Screen and/or Protective goggles can include but are not restricted to the following.

A viewing screen 105 that can be created to move with and/or track with the viewers' eyes or head or body and in one embodiment can include but is not restricted to glasses/goggle/mask 105 that can serve as but is not restricted to a display, screen or visual representation 110, 102. The visual representation can be but is not restricted to displaying the images 102 or data 104 from an imaging device/s 5 or the treatment device/s 75 or diagnostic devices 81. Imaging sources can include imaging from but not are restricted to ultrasound, MRI, CT scans, thermal or laser imaging. Data sources can include but are not restricted to energy 100 deposition, dimensional data such as length and width and depth, temporal data, devices engaged and sensory feedback 31. The data can be transmitted by hard-wiring 107 such as but not restricted to cables and fiber-optics and metal wires or by non-wire sources 103 such as but not restricted to WI-FI. In addition, the display 105 can have the form of glasses/goggle/mask 105 that can also protect a portion of the body or face from in one embodiment the viewers' face or portions of the face 109 from energy 100 or substances 99 that can include but are not restricted to organic or inorganic substances 99 or energy 100. In one embodiment the protective device 105 and the viewing device 105 can be combined or can be separate and can contain unique protections such as but not restricted to electromagnetic or thermal protections 43. In another embodiment the protective device 105 and/or the viewing device 105 can incorporate a seal 112 that can be airtight or watertight or can be breathable and non-airtight or watertight. The display can be worn on a portion of the body 107 that can include the face and can be worn like a helmet of pair of glasses or goggle. In another embodiment it can be worn and extend from another portion of the body such as the shoulders or torso or a combination of body parts. A portion or all of the display/screen/goggles/glasses 105 can be opaque, transparent or translucent.

Organisms can include but are not restricted to the following.

These methods and procedures and uses and devices can be used for and on and with human and non-human organisms.

One method for treating the parathyroid gland includes the use of non-invasive techniques to include but are not restricted to transdermal HIFU and electromagnetic focused energy treatments.

Another method for treating the parathyroid gland includes the use of minimally invasive techniques to include are but not restricted to percutaneous techniques that can include but are not restricted to MW, HIFU, RF, and radioactivity, hot and cold lasers. Medication delivery to include but not restricted to sclerotherapy, electromagnetic energy and mechanical energy.

A further object is to provide methods to ablate and control the parathyroid glands while preserving, or minimally damaging, adjacent anatomical structures, including vital organs and cellular tissue, nerves and vessels. In one embodiment, various medications, radiofrequency (RF) devices and systems, as well as various therapeutic ultrasound devices and systems can be used alone or together for the non-invasive or minimally invasive ablation of parathyroid glands are provided.

Another method for preserving local tissue while treating the parathyroid gland can include sensitizing the parathyroid gland or desensitizing the local tissue with medication and then subjecting the parathyroid gland to electromagnetic energy that preferentially treats the parathyroid gland and preserves the adjacent anatomic structures.

Another object of the present invention involves the application of energy or medication or a combination of both to one or more parathyroid glands to reduce or promote or induce increased or decreased activity of the treated parathyroid gland as a means for regulating a patient's hormone and calcium levels and osteoporosis this can include but is not restricted to placing pacer wires on the parathyroid gland, placing a catheter in the parathyroid gland that can increase or decrease blood supply to and from the parathyroid and thus alter the sensitivity of the parathyroid hormone release and production.

Another embodiment includes the localization of the parathyroid gland for surgery or for non-surgical treatment. One method can include but is not restricted to the percutaneous placement of an RF device, a GPS device or a combination of both for tracing the location of an organ to include but not restricted to the parathyroid gland. In another method the percutaneous placement of an electromagnetic energy source, such as a radiopharmaceutical which can include but is not restricted to free technetium or technetium bound to Sestamibi or other nucleotides to include but not restricted to I-123 or I-131, onto or near the target organ can then be localized using a device to include but not restricted to a radioactivity detector such as but not restricted to a pencil probe Geiger counter. In another method the radioactivity can be combined with another imaging device which can include but is not restricted to a SPECT-CT or a SPECT-MM or a PET-CT. This technique can be used to direct treatment to an organic structure that can include but is not restricted to the parathyroid gland.

Throughout this disclosure the term "treatment" can include activation, deactivation, modulation, and destruction of organic or inorganic material. Energy can include any suitable form of energy, including radiofrequency ablation (RF) and microwave (MW) and laser (L), Cryotherapy (CryT), High Intensity Focused Ultrasound (HIFU), Radioactive Therapy (Brachytherapy: BrT), Irreversible Electroporation (IRE), Electrical Current Therapies, Electrocautery, Magnetic Resonance (MR), Ultrasound, (US). A deactivating solution is one that diminishes or stops treatment; an activating substance initiates, augments, or continues treatment; and a neutralizing substance is one that neutralizes treatments or eliminates conditions under which treatment may occur. Specific examples are given throughout without loss of generality. One example of this is a disclosure that dextrose water can be delivered via a thermal probe; however, this disclosure is not limited to the use of a thermal probe. Other suitable means of delivering dextrose water are also disclosed.

Throughout this disclosure the following terms are non-exclusively defined as follows. A sheath can include but is not restricted to a tube or conduit or guide or guide that may be hollow or solid. A member can include but is not restricted to a tube, cylinder, probe wire, guide wire, guide, device and it can be solid or hollow. A controller can include but is not restricted to a device that takes an action in response to an input. A measuring device can include but is not restricted to a sensor, or a device to measure a quality or quantity of a substance or energy or a phenomenon or a biological event. A biological function can include but is not restricted parathyroid hormone activity, temperature, calcium levels, ionizing calcium, electrolytes, local temperature around parathyroid, neuronal function (laryngeal nerves), larynx and innervation, respiratory function, sympathetic and parasympathetic (primary and secondary) function, arterial flow, venal flow, brain function, cardiac functions, blood pressure, chromatography, and vital and hormonal and physiologic measurements, signs and symptoms. Placement of a needle can include but is not restricted to placement by at least one organism with or without robotic assistance. The energy delivered and the insulation experienced at any given moment during treatment by the user's target and non-target tissue can both vary and can be variable to include but not restricted to duration, direction, exposure, periodicity or frequency. The techniques and methods in this disclosure can be applied to humans or non-human organisms. An inhibitor is an energy or substance that can alter, modulate, control, activate, deactivate, or neutralize an energy or a substance and can include but is not restricted to thermal energy where an RF device and the heat produced can be inhibited by a cold or cooled liquid or gel in the vicinity or perimeter tissue or target tissue; or cold from a cryoprobe device can be inhibited by a heated liquid or gel or by an RF device that warms the tissue; or radioactivity from brachytherapy is inhibited by lead or other elements that restrict radioactivity; or a laser device where the electromagnetic light energy is inhibited by an opaque or translucent or semi-opaque material; or an RF device where the RF transmission and penetration are inhibited by a substance that inhibits RF transmission and can include but is not restricted to Dextrose water or a hydrogel or a low- or non-osmolar or non-ionic compound; or an electrical current that is inhibited by a substance that prevents electrical transmission that can include but is not restricted to a non-ionic or low or non-osmolar substance; an acid that can be inhibited by a base or a base that can be inhibited by an acid; a sclerosant such as ethanol or Sotradecol that can be inhibited by dilution by saline or water; a carboxylated molecule that can be inhibited by a decarboxylating enzyme or substance; a wavelength that can be inhibited by a wavelength with a wavelength that is has a frequency and amplitude and periodicity that inhibits the primary or the secondary wavelengths produced that can include but is not restricted to a second wavelength that is the mirror of the first wavelength; a phase altering substance that can metamorphasize from a liquid to a gel and can capture a substance, which can include but is not restricted to an enzyme or anti-angiogenic compound that can be injected into the target tissue and if it leaks out of the target tissue can then captured and neutralized or inhibited or denatured; an adhesive that can be deactivated by UV light; the inhibitor can be at least one energy or a substance that inhibits the treating energy or a substance. A hormone in its classic definition refers to a chemical which can be released by a cell or a gland in one part of the body that sends out signals or messages or information that can affect cells or tissue or function in other parts of an organism. A hormone can include but is not restricted to an organic or inorganic substance or molecule that can include but is not restricted to a biological substance that can be produced in an organism from endocrine or exocrine glands, or from biological tissue that can be ectodermal, mesodermal or endodermal and which can be composed of or from but not restricted to any combination of organic substances such as but not restricted to a peptide, a protein, a fat, a carbohydrate, or a steroid, and examples can include but are not restricted to parathyroid hormone, insulin, gastrin, testosterone, estrogen, follicle stimulating hormone, growth hormone, prolactin; and the hormone can include inorganic substances that can include but are not restricted to a mineral that can include but is not restricted to Calcium, Zinc, Iron or Magnesium and said hormone can exhibit or produce or exert or influence an effect on both local and distance tissue within the organism. Preferred and alternative examples of the present invention are described in detail below with reference to the following drawings:

FIG. 1 is a frontal view, anatomic rendering of the thyroid and parathyroid glands in the anterior mid neck. There are two thyroid lobes, which include the right lobe of thyroid 25 and the left lobe of thyroid 22 and the isthmus of the thyroid 18. Any portion of the thyroid gland or tissue can be referred to as thyroid gland or tissue 20. There are four parathyroid glands, which include the right superior parathyroid gland 10; the right inferior parathyroid gland 14; the left superior parathyroid gland 12; and the left inferior parathyroid gland 16 or an ectopic parathyroid gland 15 any individual parathyroid gland or parathyroid tissue 10 can be referred to include but not restricted to a normal parathyroid gland or a parathyroid adenoma, hyperplasia, carcinoma or normal functioning or hypo-functioning or hyper-functioning parathyroid gland in a typical or an atypical, ectopic, location. A nerve 19 is depicted on the right specifically the Recurrent Laryngeal Nerve, but there are numerous nerves 19 bilaterally including the innervating sympathetic and parasympathetic nerves as well as the traversing Laryngeal Nerves 13 and the Vagus nerve 21, which reside near or in the vicinity 17 of the parathyroid glands 30. The thyroid 20 and parathyroid 30 reside within the neck 03 and are beneath the skin's surface 6 and are subcutaneous tissue 92. Treatment devices 80 and imaging devices 5 can be placed on the skin 6 (shown), or through the skin 90 percutaneously (not shown) or non-percutaneously such as but not restricted to transcutaneously (not shown) in order to treat and or visualize the target organs, specifically the parathyroid 30 and the parathyroid tissue 30. Thyroid gland tissue shall generically be referred to as 20 and Parathyroid tissue or gland shall generically be referred to as 30.

Figures 2, 3:
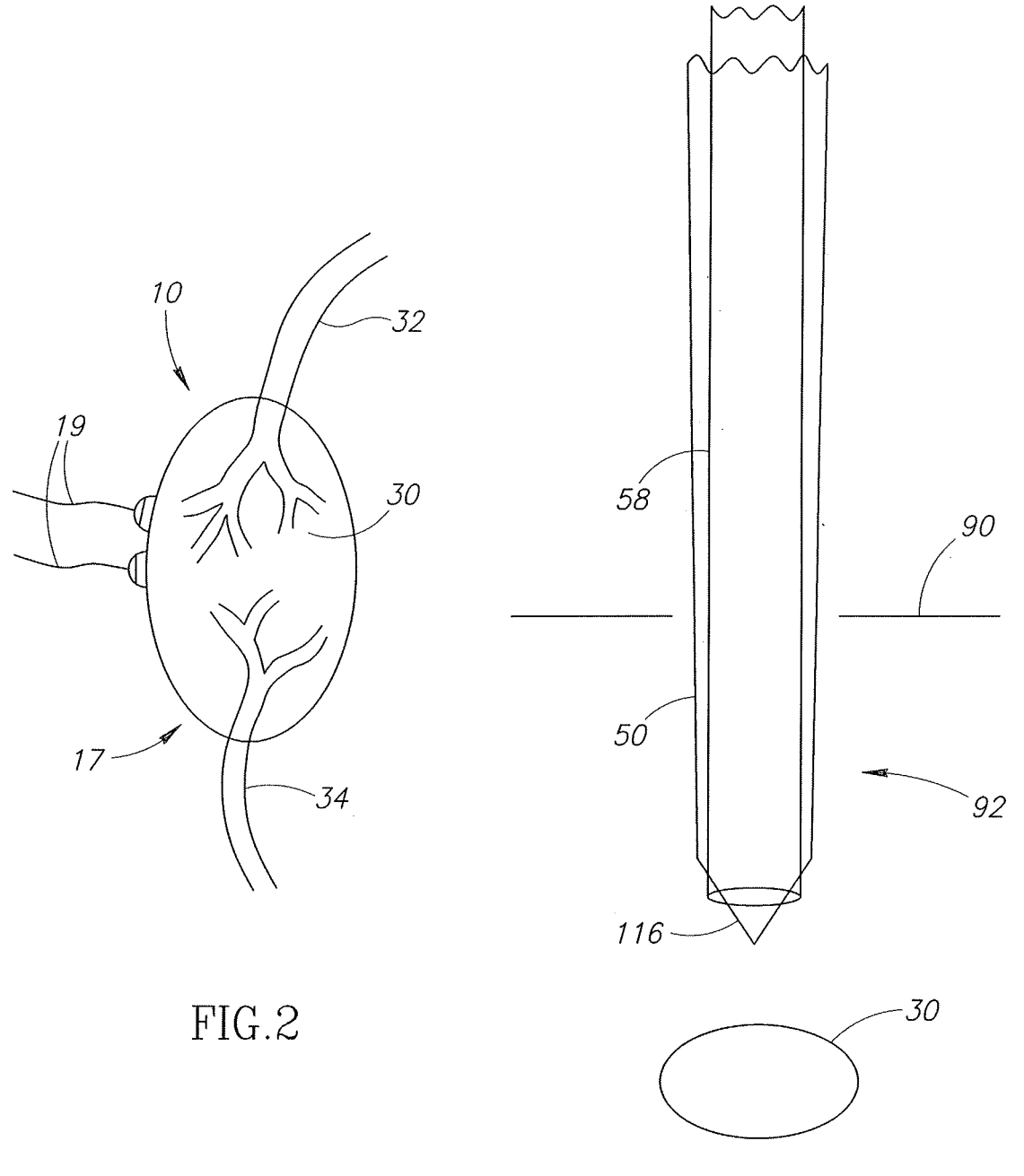
FIG. 2 is an isolated view of the parathyroid gland.
FIG. 3 is a rendering of a device that can be used to penetrate the skin and the subcutaneous tissue to reach the parathyroid gland.

FIG. 2 is an isolated parathyroid gland 30 that can represent but is not restricted to a normal parathyroid gland, an enlarged normal gland, a hyperplasic gland, an adenomatous gland and/or a hyper- or hypo or normally functioning gland 30 of the parathyroid 30 or a carcinoma 30. There are arterial blood vessels that create inflow 32 and veins 34 that provide outflow of blood from the parathyroid gland 30. The innervating nerves 19 of the parathyroid 30 are depicted. There is tissue that surrounds or is in the vicinity 17 of the parathyroid gland 30

FIG. 3 is a rendering of a device 58 that can be used to penetrate the skin 90 and the subcutaneous tissue 92 to reach the parathyroid gland 30. In this embodiment the penetrating device is configured as a needle, which is pointed or cutting or piercing tip 116 and has a guiding device 50, which can include but is not restricted to a sheath or catheter that allows repetitive access to the parathyroid tissue 30.

FIG. 4 is a rendering of a guiding device 50 with a blunt end 61 but not restricted to a blunt end. Inside of the guiding device 50 is a tube/conduit 52 that can have one 54 or more than one channel 56 for the introduction of substance 99 to include but not restricted to solids 76, liquids 78 or gasses 77 (not shown).

FIG. 5 is a rendering of a guiding device 50 penetrating the parathyroid tissue 30. There is tube 52, which provides for the passage of substances 99 to include but not restricted to solids 76, liquids/gels 78 or gases 77 (not shown). The tube/conduit 52 is in proximity to the parathyroid tissue 30 the artery 32 the nerve 19 and the vein 34. The tube/conduit 52 can include but is not restricted to a needle, catheter, or a delivery device. In one embodiment the guide 50, tube/conduit 52 can be a needle 52 and can have but is not restricted to having a groove or mechanical thread configuration 66 that penetrates the parathyroid 30 with a screw-like motion or mechanism. The threads/grooves 66 can be on the inside or the outside or be integral to the structure of all or a portion of the tube 52, such as but not restricted to the distal aspect 51 of the tube 52.

Figure 6:
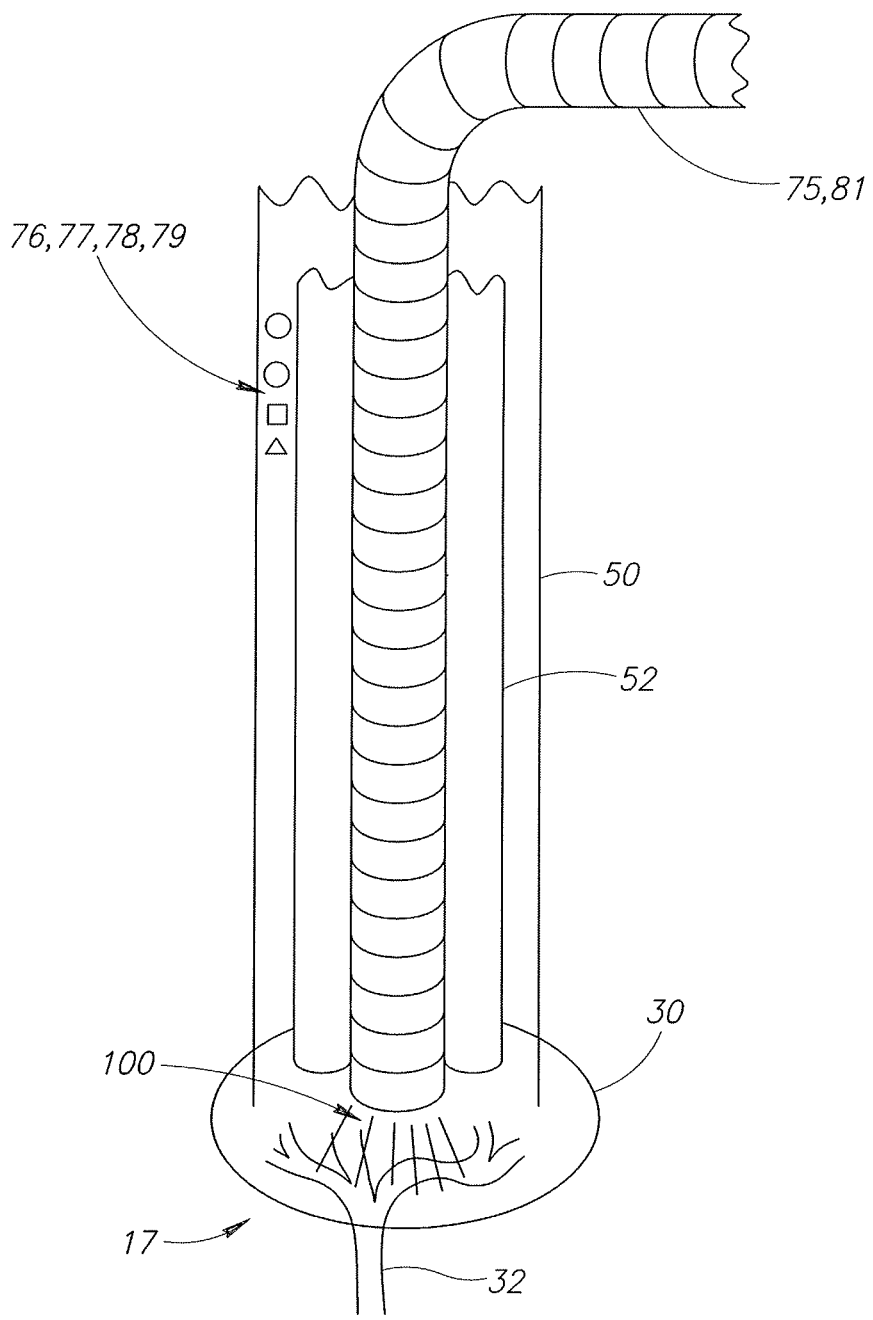
FIG. 6 is a rendering of a guiding sheath penetrating the parathyroid gland 30. There can be an additional tube or additional guiding sheaths, and these conduits can provide for the passage of a device and the guiding devices can serve multiple functions to include but not restricted to insulation for the local tissue and delivery of a substance to the target tissue.

FIG. 6 is a rendering of a guiding sheath 50 penetrating the parathyroid gland 30. There can be an additional tube 52, which provides for the passage of substances 99 such as solid 76 or liquid 78 or gas 77 material(s) and can serve multiple functions to include but not restricted to insulation for the local tissue. The tube/conduit 52 is in proximity or can be penetrating the parathyroid tissue 30) the artery 32 and the vein or nerve (not shown). The solid device/probe/member 75 can have multiple uses that include but are not restricted to treatment, localization and visualization of the parathyroid 30. Treatment device 75 can include but is not restricted to the delivery of energy 100 such as but not restricted to electromagnetic energy or mechanical energy or heat or cold and the viewing or visualizing device 75,81 can include but is not restricted to a fiber-optic or thermal viewing device. Traversing or being transported through the tube/conduit 52 can be a solid device/probe/member 75 that can be used to partially or fully ablate the parathyroid tissue 30 or selectively the parathyroid arteries 32 or veins or nerves (not shown).

Figure 7:
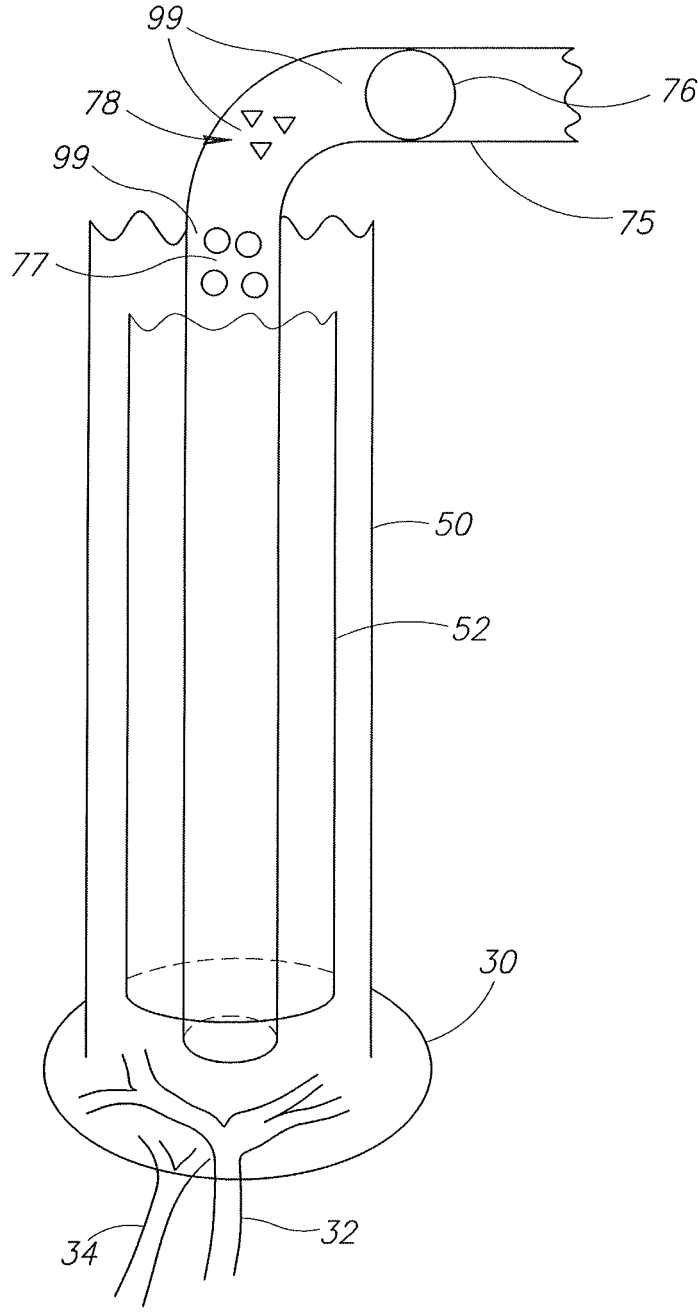
FIG. 7 is a rendering of a guiding device penetrating the parathyroid tissue. There can be an additional tube or guiding device, and these conduits can provide for the passage of a substance and can serve multiple functions to include but not restricted to insulation.

FIG. 7 is a rendering of a guiding device 50 penetrating the parathyroid tissue 30. There can be an additional tube 52, which provides for the passage of a substance 99 to include but not restricted to a substance to include but not restricted to solids 76, liquids/gels 78 or gases 77 material(s) and can serve multiple functions to include but not restricted to insulation. The tube 52 is in proximity to the parathyroid tissue 30 the artery 32 and the vein 34. Traversing the tube/conduit 52 can be a hollow or solid device 75 that can be used to partially or fully ablate the parathyroid 30 or the parathyroid arteries 32 or veins 34 or nerves 19 (not shown) that can deliver one or any combination of substances 99, solids 76, liquids 78 or gasses 77.

Figure 8:
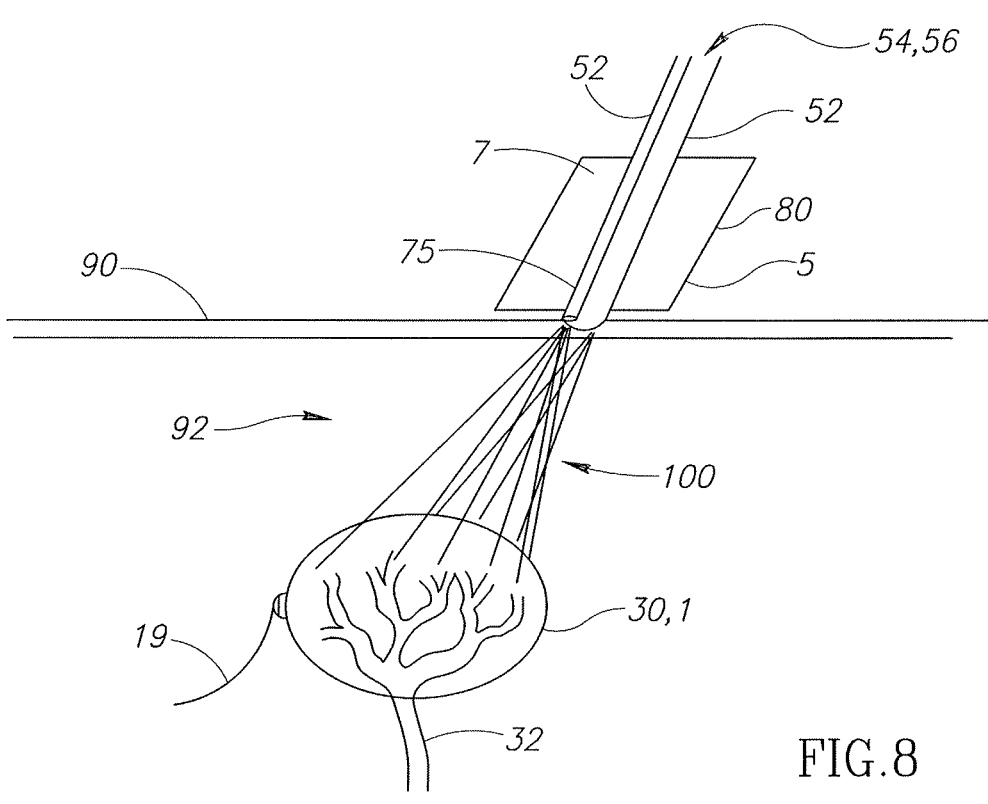
FIG. 8 is a rendering of one embodiment of a transcutaneous energy delivery device for ablating one or more parathyroid glands, which can contain a passageway or conduit through the transducer for the transport of a solid or hollow tube or device or probe or an additional conduit device. The passageway device through the transducer can be built into or separate from the transducer.

FIG. 8 is a rendering of one embodiment of a transcutaneous imaging 5 and or energy delivery device 80 for ablating one or more parathyroid glands 30. The energy transcutaneous delivery device 80 delivers energy 100 through the skin 90 through the subcutaneous tissue 92 and the target organ 1, the parathyroid gland 30 can be imaged with a transcutaneous imaging device 5 to ablate parathyroid tissue 30 preferably while the surrounding tissues 17, anatomical structures (including, e.g., nerves 19, vessels 32, 34, thyroids 20) are preserved. In one possible embodiment, the transcutaneous energy delivery device 80 can include but is not restricted to HIFU (which is deliverable though a transcutaneous device 80 allowing for the MIT, TTMIT, or non-invasive, ablation of the parathyroid glands 30). In this embodiment the device 80 uses energy 100 which can be electromagnetic or chemical or kinetic energy 100 for either diagnostic or therapeutic purposes. The treatment device 80 can be coupled with a diagnostic device 5 or the treatment and the diagnostic devices that are combined 7 or are not combined. The energy 100 is directed at the target tissue to include but not restricted to the parathyroid 30 and can be directed toward its vascular supply including the arteries 32, veins 34 (not shown) and the nerves 19. The electromagnetic energy can pass through the skin 90 and subcutaneous tissue 92. A tube or conduit 52, which can contain one 54 or more 56 channels can be placed through the transcutaneous imaging 5 or treatment device 80 and within the tube/conduit 52 can be an additional tube 52, which can be solid or hollow and can be used for delivery of a substance 99 or energy 100 or can be used for stability or guidance that can be or contain a device 75 that can deliver additional substances 99 or energy 100 to the target tissue 1, the parathyroid gland 30. The tube/conduit 52 can include and can refer to a but is not restricted to a needle 58, a stylet 57, a sheath 59, a hook 60, a guide wire 70 a guide sheath 50, a treatment delivery device 75, a sensor 31, a probe 94, or a percutaneous diagnostic device 81. The term tube 52 or conduit 52 can be used interchangeably and can relate both to a tube 52 or conduit 52 that can be solid or hollow or a combination of solid and hollow and can contain one 54 or more channels 56. It is recognized that a conduit more often can imply a tube that is hollow and can transport a substance 99 or energy 100 and that a tube can generically refer to an object that can be either solid or hollow or a combination of these two elements.

Figure 9:
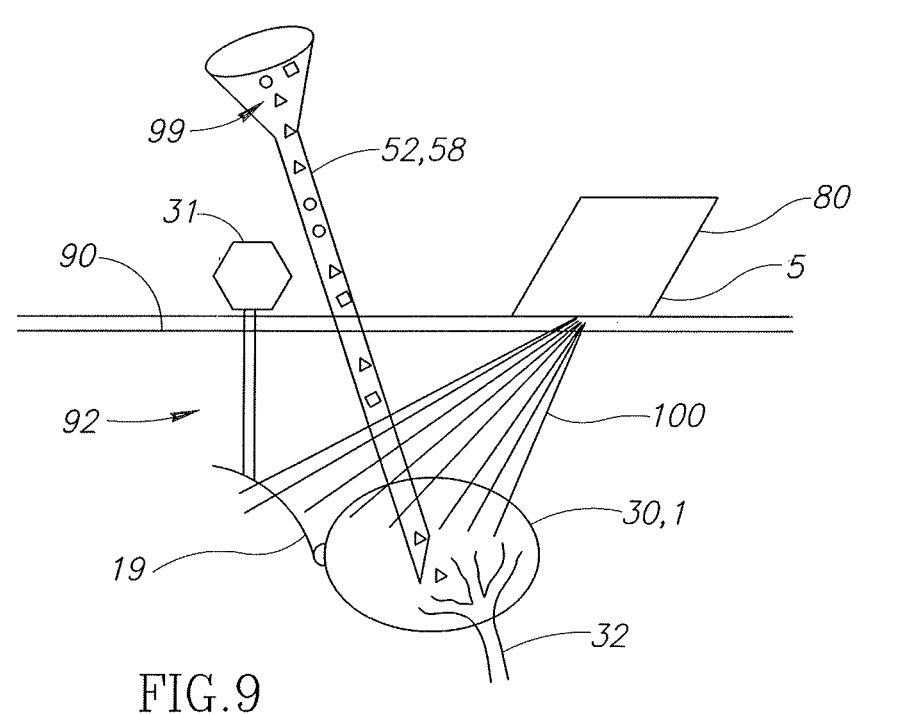
FIG. 9 is a rendering of a transcutaneous device and one or more tubes, devices, delivery systems, or conduits, such as a needle or probes, that can penetrate the skin and subcutaneous tissue to reach and that can penetrate the target tissue, its vascular supply, and nerves to treat the target tissue, the parathyroid gland, or non-target tissue in the vicinity of the target tissue.

FIG. 9 is a rendering of a transcutaneous device 80, 5 that uses electromagnetic or mechanical or kinetic energy, which can include but is not restricted to motion and heat thermal energy 100 for either diagnostic and imaging and visualization or therapeutic purposes. The energy 100 is directed at the target tissue to include but not restricted to the parathyroid 30 and can be directed toward its vascular supply which can include the arteries 32, the veins (not shown) or the nerves 19. The electromagnetic or mechanical or kinetic energy 100 can pass through the skin 6, 90 and subcutaneous tissue 92. A delivery tube 52 needle 58 or imaging or treatment device 75 can penetrate the skin 6, 90 and subcutaneous tissue 92 to reach and can penetrate the target tissue to include but not restricted to the parathyroid 30 and its vascular supply 32, and nerves to treat the parathyroid gland 30. A solid 76, liquid 78 or a gas 77 substance 99 or a combination of these substances can be delivered to the parathyroid 30. In one embodiment the guidance of the needle 28, 52 and substance placement is visualized or measured by the cutaneous 5 imaging device 80 that can include but is not restricted to an ultrasound, MR, CT, laser or thermal imager. In another embodiment the device 80 can activate or can deactivate the solid 76, liquid 78 or a gas 77 substance 99. One or more than one device 80 or delivery tube 52 needle 58 or imaging or treatment device 5, 80 (shown), 75, 81 can be used and one or more than one form of energy 100 can be used alone or in multiple combinations. The local tissue 17 and the subcutaneous tissue 92 and nerves 19 can be protected from the delivery of energy 82 or non-energetic methods or substances and can be delivered by multiple methods to include but not restricted to a delivery tube 52 needle 58 or imaging or treatment device 75 to protect the local tissue 17 in the vicinity of the target tissue parathyroid 30. A sensor 31 can be used to monitor the local vicinity non-target tissue 17 or the target tissue 130 (not shown).

Figure 10:
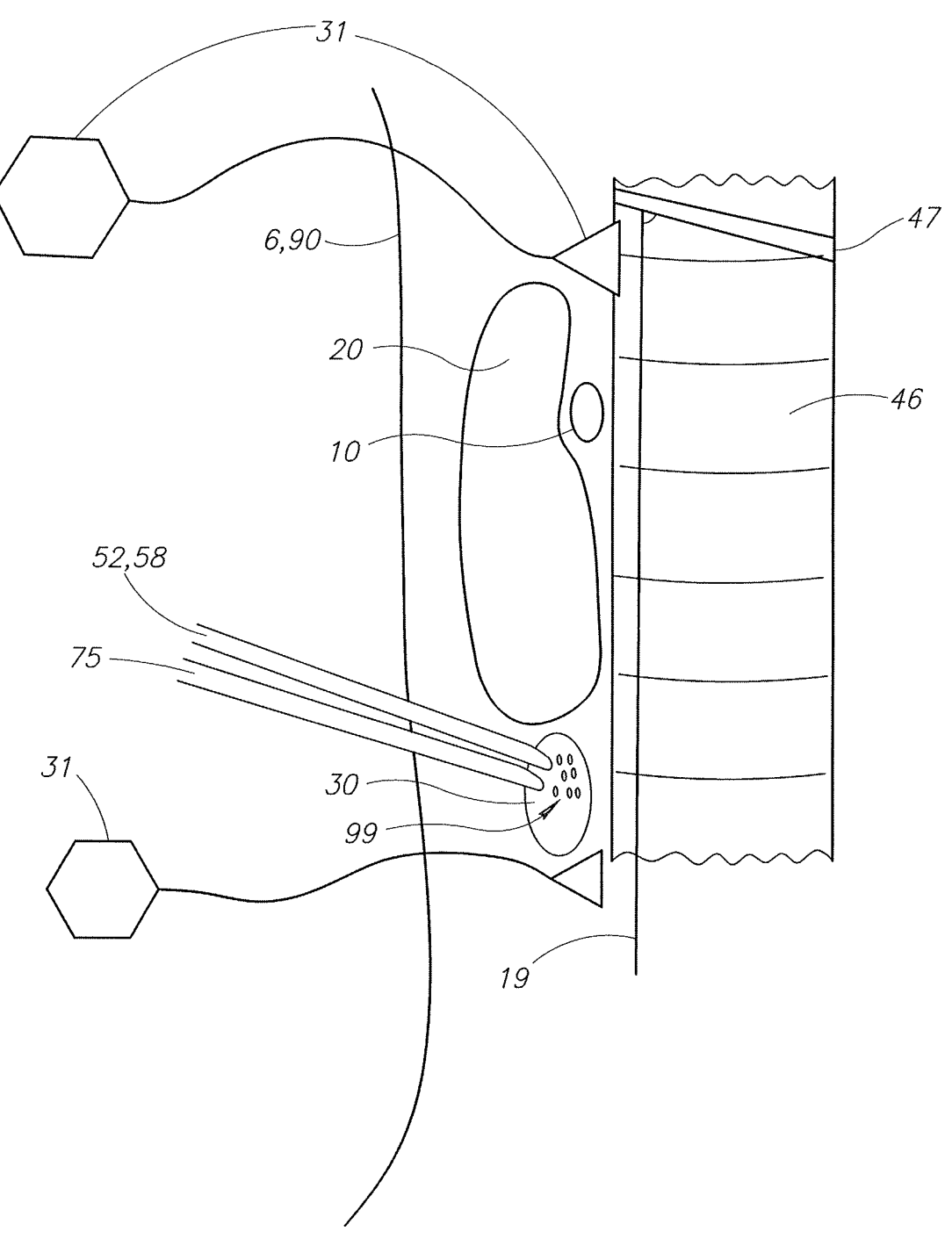
FIG. 10 is a sagittal cross-sectional rendering of the thyroid 20 and a normal superior parathyroid gland, target tissue and an abnormal inferior parathyroid gland. The trachea lies adjacent to and posterior to the thyroid and the two parathyroid glands. A delivery device can include or not include a sensor sensitive delivery device that can protect the non-target vicinity tissue and modulate treatment to the target tissue.

FIG. 10 is a sagittal cross-sectional rendering of the thyroid 20 and a normal superior parathyroid gland 30 and an abnormal inferior parathyroid gland 30. The trachea 46 lies adjacent to and posterior to the thyroid 20 and the two parathyroid glands 30. The Recurrent Laryngeal Nerve 13 which innervates the Larynx 47 and the local non-target vicinity tissue 17 and organs 46, 15 and nerves 19 can be monitored 31 or protected from the ablative substances or energetic or non-energetic methods delivered to the parathyroid gland 30 and the delivery can include but is not restricted to a tube or conduit 52, needle 58 or imaging or treatment device 75. A sensing device 31 can include or not include a sensor sensitive to the delivery device 31 output to include but not restricted to electromagnetic energy or kinetic or mechanical energy 100 that can include thermal or light or electrical measurements to include but not restricted to resistance (ohms) voltage or amperage and said sensor device 31 information and feedback can be used to protect the non-target vicinity tissue 17 and determine the treatment to the target tissue 1, 30.

Figures 11, 12:
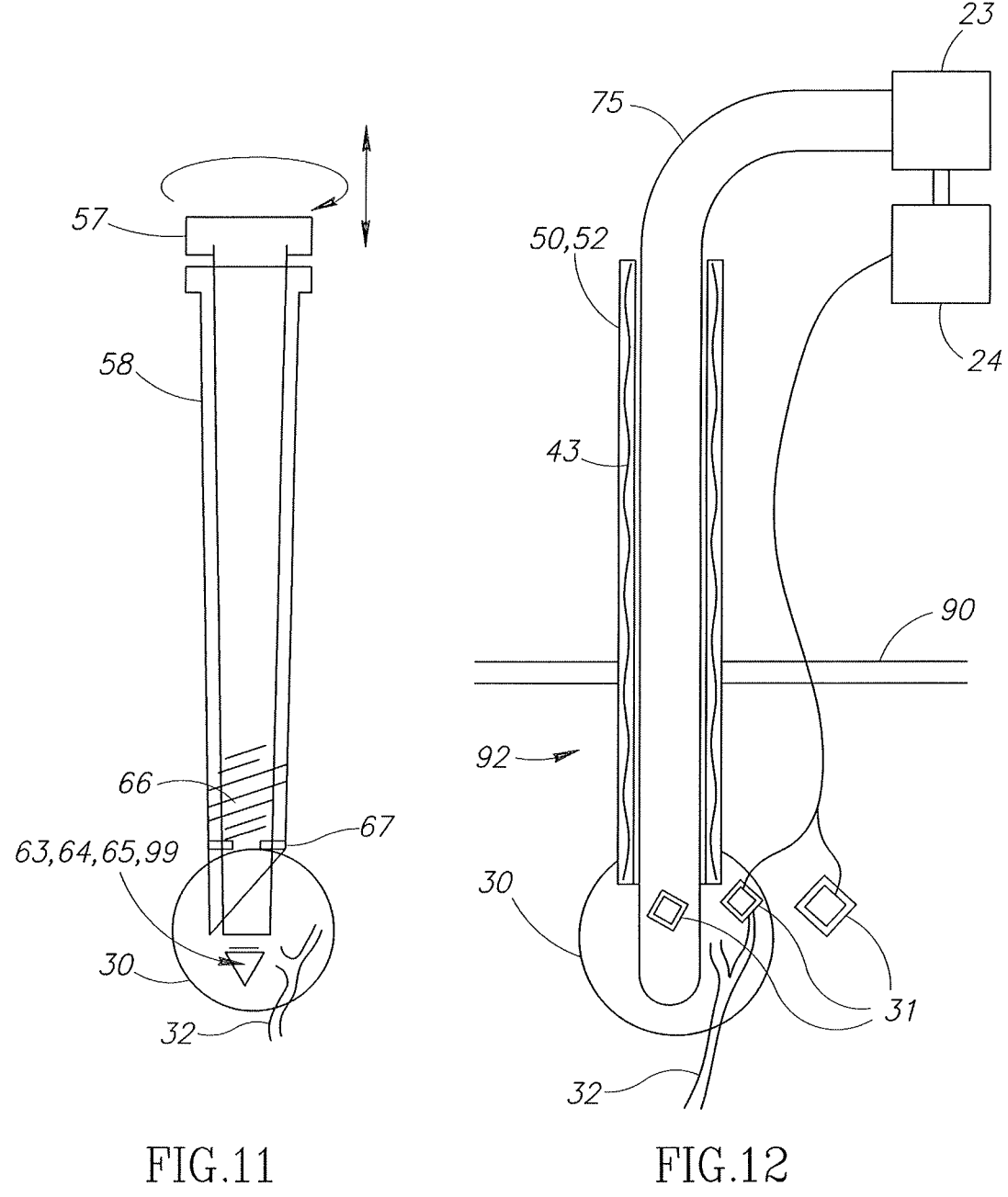
FIG. 11 is a tube or conduit or needle percutaneously depositing a substance/s, which in the preferred embodiment can include in standard radioactive seeds for brachytherapy. The delivery system can include a needle with a stylet with interlocking grooves or thread and a method and device for governing the transit of the stylet and needle for the delivery of the brachytherapy or non-brachytherapy substances.
FIG. 12 is an example of a device that can utilize but is not restricted to electromagnetic or kinetic or thermal or mechanical energy or methods. The device can be composed of an elongated member that can include a distal component that can deliver the treatment such as an RF or microwave or laser probe and a second component which can be located more proximal to the distal component that is insulated or prevents the deposition of treatment to the tissue that is more proximal to the distal component that can deliver the treatment. Sensors and controls and generators and feedback mechanisms and loops can be used to regulate treatment to both the target tissue, parathyroid gland and the local vicinity tissue.

FIG. 11 is a tube or conduit 52, needle 58 for percutaneously depositing a substance/s 99 to include but not restricted to solids 76, liquids/gels 78 or gases 77 material(s), which in the preferred embodiment can include in one embodiment a standard radioactive seed 63, a radioactive bead 64 that can measure less than or equal to 1 mm or can be greater than 1 mm or in another embodiment a biodegradable colloid radioactive 65 for brachytherapy. In one embodiment there is a stylet 57, which fits into the hollow needle and in one embodiment governors can be locking or non-locking and can serve as a delimiter and/or guiding mechanisms 66 can include but are not restricted to matching treads 53 or ruts, grooves 66 or locking delimiters or governors 67 or can be without these governors 67 or can be a combination of these elements such that the stylet can be screwed down or be rotated 36 or advanced 68 into position and can lock and unlock. The stylet 57 and tube/conduit 52 or needle 58 together can have a delimiter or governor that limits the distance or motion traveled by the stylet 57 and which can adjust to position or seat the treatment substance 99, or brachytherapy 63, 64, 65 into position within the parathyroid gland 30. A stylet 57 and tube/conduit 52 or needle 58 or device delivery 75 with governors and locking and guiding mechanisms 66 can be used for non-brachytherapy treatment and visualization systems.

FIG. 12 is an example of an energy device 75 that can utilize but is not restricted to electromagnetic or kinetic or thermal or mechanical energy or methods and that is composed of an elongated member that can include but is not restricted to a distal component where the treatment is delivered and a more mid component an proximal component that is insulated 43 or where a tube/conduit 52, guiding sheath 50 can be insulated 43.

The device can penetrate the target tissue, parathyroid gland 30 and deliver the treatment in a manner that protects the local vicinity tissue 17. The treatment device 75 can pierce the skin 90 and subcutaneous tissue 92 in a percutaneous manner in order to deliver the treatment. This can be combined with a transcutaneous treatment 80 or an imaging device 81 that can include but is not restricted to diagnostic ultrasound and MR and thermography and CT or a percutaneous imaging device to include but not restricted to a fiber-optic or laparoscopic or laser imaging device in order to define the target tissue, parathyroid gland 30. The energy delivery device 75 can be coupled to energy generator 23. In this embodiment, the energy delivery device 75 and the energy generator 23 can be coupled together and can receive feedback or information from a sensing device 31 that can be integrated into the member of the energy delivery device 75 or the sensor can be separate from the energy delivery device and can lie in or near the parathyroid 30 or in the vicinity non-target tissue 17 and the sensor 31 can serve as a controller of the treatment.

Figures 13, 14:
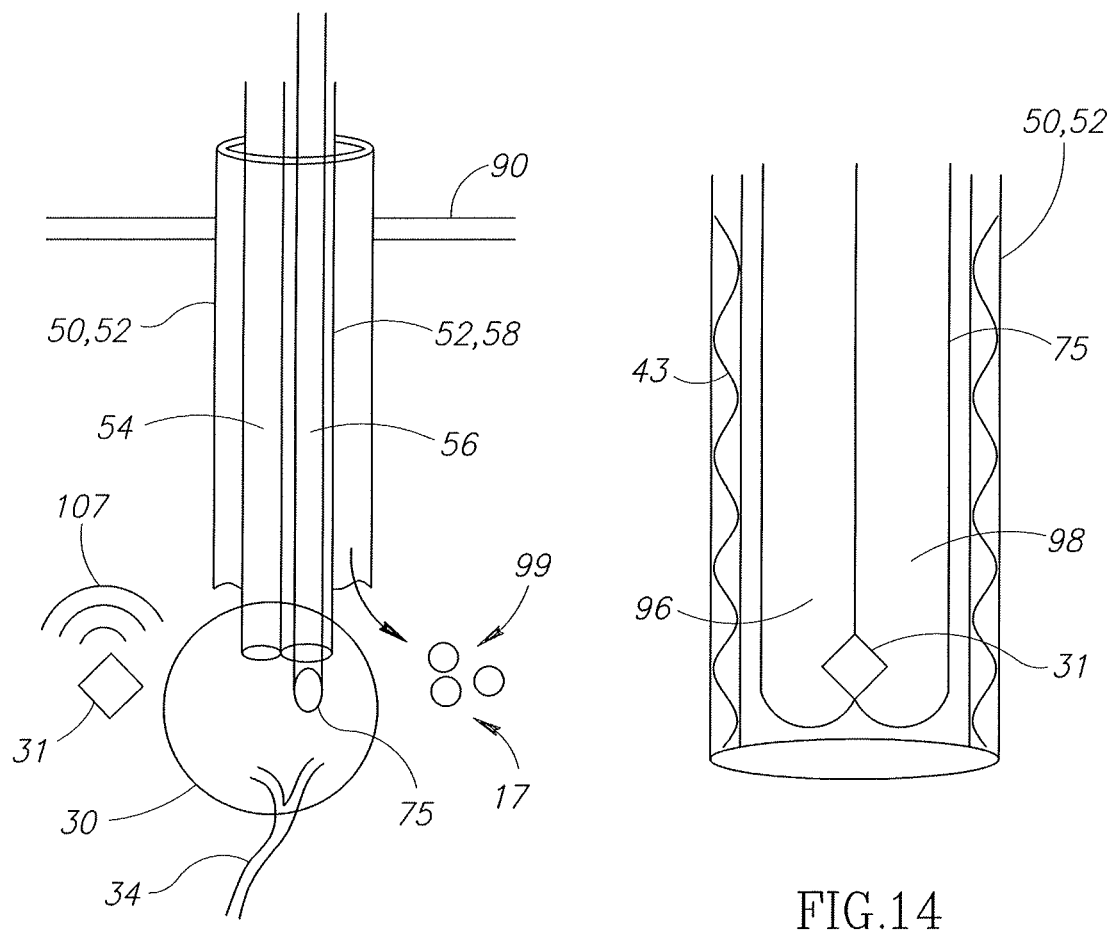
FIG. 13 is an embodiment of one or more tubes or conduits such as a needle or guiding sheath and each can contain one or more channels or lumens that extend through at least a portion of or the entire length of the tube or conduit and can be used to biopsy or deliver treatment to the target tissue, parathyroid gland, or the local vicinity tissue. Sensors can be used or be a component of the tubes or conduits.
FIG. 14 is an embodiment of a percutaneous device and a guiding tube that can combine hot thermal and cold thermal energy for treatment. The combination of differing thermal elements can be switched on and off to control the precise temperature, and the device can include a sensing device.

FIG. 13 is an embodiment of a tube/conduit 52 or needle 58 or guiding sheath 50 that can include one channel/lumen 54 or more than one channel or lumen 56 that extend through at least a portion, or the entire length, of the tube/conduit 52 or needle 58 and can contain one or more channels. One or more channels can be configured as pathways used for the delivery of solids 76, liquids, gels 78 or gasses 77. Channels 54, 56 can be used for localization/visualization of tissue 30 or treatment or a combination of either or both localization/visualization or treatment and permit the passage or transport of substances 99 or devices 75, 31, 81 to treat the target tissue parathyroid gland 30 and monitor with a sensor 31 and protect the vicinity non target tissue 17 with a substance 99.

FIG. 14 is an embodiment of a percutaneous device 75 and a guiding tube 50 that can combine hot thermal 98 and cold thermal 96 energy for treatment. The combination of differing thermal elements can be switched on and off to control the precise temperature, which can include a sensing device 31.

Figure 15A:
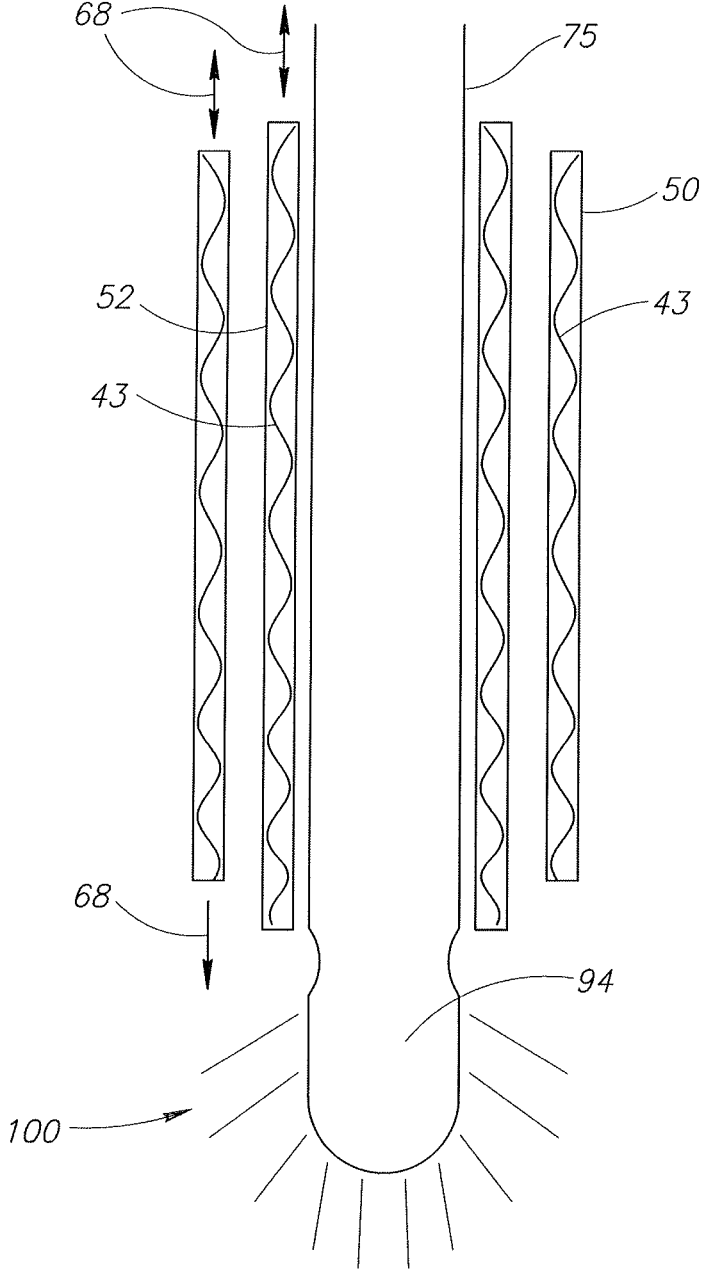
FIG. 15A is an embodiment of a treatment delivery device to include but not restricted to a laser, RF, or microwave probe that can have an energy delivery probe component and an insulating component that can be fixed or not fixed. In this embodiment an insulated guiding tube or conduit can assist in altering the energy delivery.

FIG. 15A is an embodiment of an energy delivery device 75 to include but not restricted to a laser, RF, or microwave probe that can have an energy 100 delivery device probe component 94 and an insulating 43 component that can be fixed or not fixed. In this embodiment an insulated 43 guiding tube/conduit 50 can also assist in altering the energy delivery.

Figures 15B, 15C:
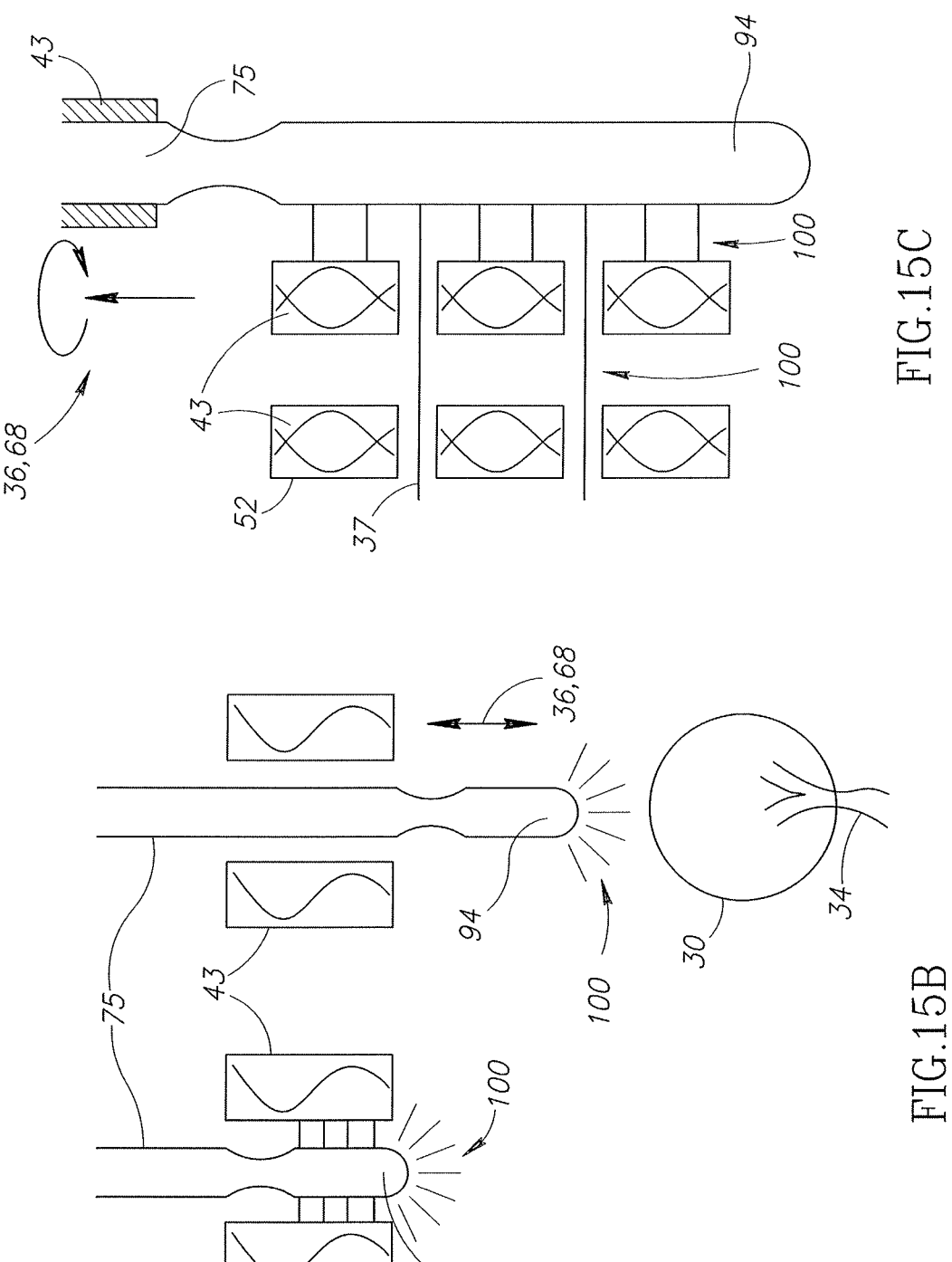
FIG. 15B is an embodiment where the relationship of the energy delivery device or probe component and the insulating component and the guide are not fixed and the length or surface area of the treatment device can be increased and/or decreased which is done in FIG. 15B and is done by rotating or advancing or retracting or any combination of movements of the insulation or the guide or the treatment device relative to each other.
In FIG. 15C one embodiment can include a laser treatment device and two conduits that contain openings that can include but are not restricted to slits or holes that serve as fenestrations or windows to the laser light. When the conduit fenestrations are not aligned the amount of light or heat escaping the two conduits and reaching the target tissue is more limited than when the fenestrations are aligned.

FIG. 15B is an embodiment where the relationship of the energy delivery device 75 or probe component 94 and the insulating component 43 and the guide 50 are not fixed and the treatment device 50 can be advanced/retracted 68 or rotated 36 relative to the insulation 43 and the guide 50 or any combination of movements of the insulation or the guide or the treatment device relative to the each other.

In FIG. 15C one embodiment can include a laser treatment device 75 and two conduits 52 that are insulated 43 that contain openings or fenestrations 37 that can include but are not restricted to slits or holes 37 that serve as fenestrations 37 or windows 37 to the laser light. When the conduit fenestrations 37 are not aligned the amount of light or heat escaping the two conduits 52 and reaching the target tissue 30, 1 (not shown) is more limited than when the fenestrations 37 are aligned. In one embodiment the two tubes/conduits 52 can be configured in a logarithmic pattern with strategic cut-outs that can be moved-linearly 68 or rotated 36.

Figure 16:
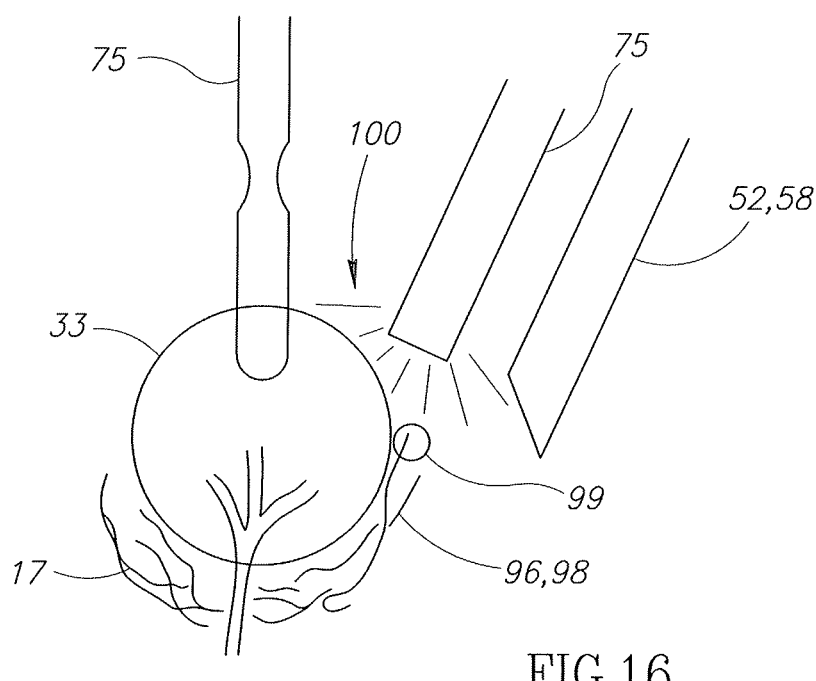
FIG. 16 is an embodiment in which a percutaneously placed treatment device resides within the target tissue, parathyroid gland and one or more tubes/conduits/catheters or needles or devices can be placed into the local vicinity tissue and can introduce a substance or energy, which can include but is not restricted to Dextrose 5% water that is chilled prior to instillation or chilled after or during instillation from a thermal treatment device, which can include but is not restricted to a thermal probe or a cooling needle that can include cold or heat and can be infused or placed into the local vicinity tissue and can serve as a heat-sink to protect the local vicinity tissue if heat is the primary thermal treatment to the target tissue or can include warming to protect the local vicinity tissue if cryotherapy is the primary thermal treatment to the target tissue.

FIG. 16 is an embodiment in which the target tissue, parathyroid gland 30, contains percutaneously place a treatment device 75 and a tube/conduit/catheter 52 or needle 58 can treat the local vicinity tissue 17 with a substance 99 or energy 100, which can include but is not restricted thermal cold 96 or heat 98. Either with or without the actual treatment of the vicinity tissue with thermal cold 96 or heat 98, the instillation of a cold 96 or body temperature or heated 98 substance such as but not restricted to a liquid 78 such as but not restricted to dextrose water this method can act as a heat-sink to protect the local vicinity tissue 17.

Figures 17A, 17B:
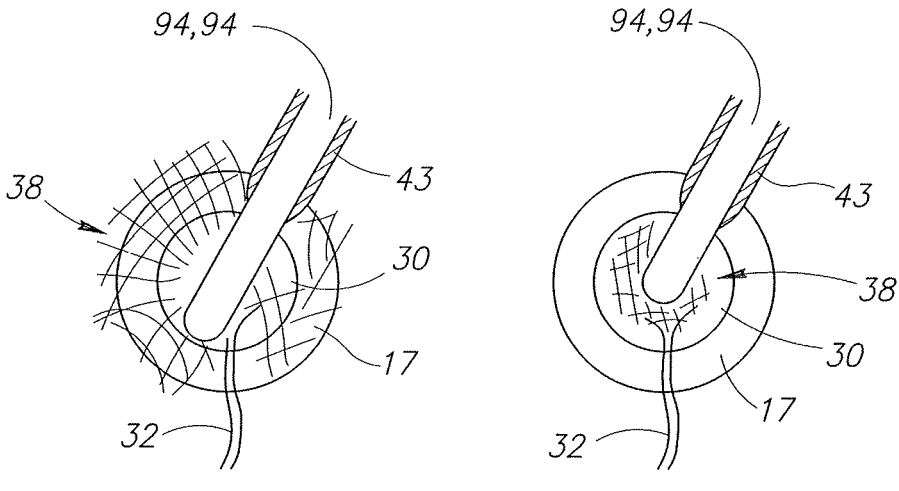
FIGS. 17A-B depict a simplified diagram of the zone of ablation. The treatment device is placed into the target tissue and a central area adjacent to the probe or treatment device is irreversibly ablated. In the MIT there are multiple zones of ablation that yield intermediate or partial damage to the vicinity tissue beyond the target tissue and extending into the vicinity or local non-target tissue. With TTMIT the energy deposition or the substance deposition or the local protective treatment are designed to reduce the vicinity or local non-target tissue to as minimal an area as possible even possibly with reduced effectiveness of the treatment of the target tissue.

FIGS. 17A-B depict a simplified diagram of the zone of ablation. The treatment device is placed into the target tissue 1, 30 and a central area adjacent to the probe 94 or treatment device 75 causes irreversible ablation 38. In the MIT there are multiple zones of ablation that are of intermediate or partial damage to the vicinity tissue 17 beyond the target tissue 1, 30 and extending into the vicinity or local non-target tissue 17. With TTMIT the energy deposition 100 or the substance deposition 99 (not shown) or the local protective treatment (not shown) are designed to reduce the vicinity or local non-target tissue 17 to as minimal an area as possible even possible at the reduced effectiveness of the treatment of the target tissue 30,1. In FIG. 17A the zone of irreversible ablation 38 affects both the parathyroid 30 target tissue 1 and the vicinity tissue 17. In FIG. 17B only the parathyroid 30 target tissue 1 is affect and the parathyroid tissue may even be incompletely ablated 38 but the vicinity tissue 17 is partially or completely spared from ablation 38.

Figure 18A:
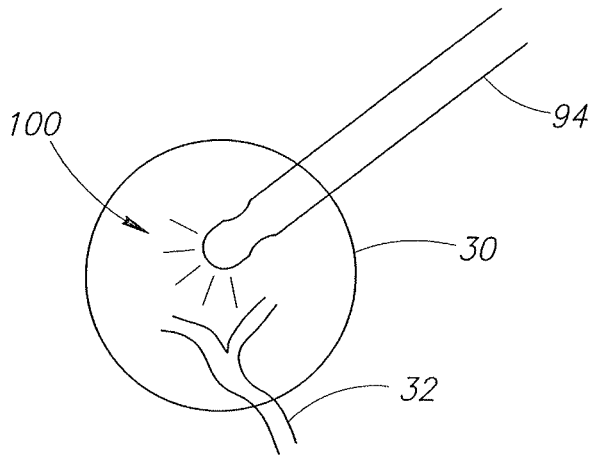
FIG. 18A is an embodiment of one probe or device.
Figure 18B:
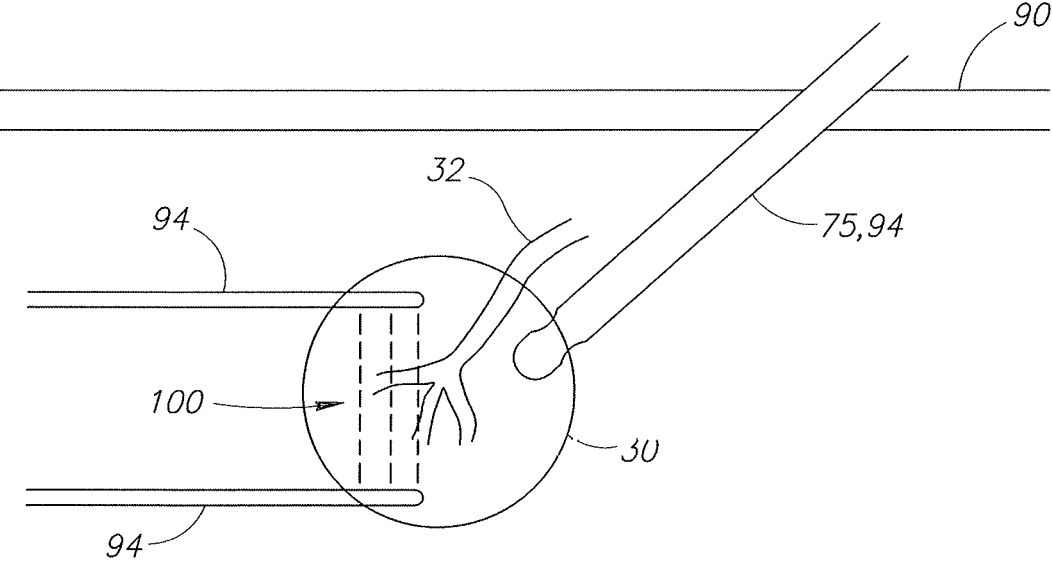
FIG. 18B depicts multiple probes within the target tissue 1 parathyroid gland.

FIG. 18A is an embodiment of one probe or device or FIG. 18B multiple probes within the target tissue 1 parathyroid gland. This embodiment can include one or more probes and is dependent on the size of the target tissue 1, parathyroid gland 30 that is being treated and on the treatment device being used. In one embodiment such as but not restricted to Irreversible Electroporation (IRE) two or more electrodes/probes/members/tines 75, 94 are utilized and the electromagnetic energy, current, is transmitted between these electrodes/probes/members/tines 75, 94. Since IRE does not effectively coagulate blood vessels a second treatment modality and device 75 such as but not restricted to electro-cautery may be needed to coagulate the blood vessels such as the arteries 32 and veins 34.

Figure 19A:
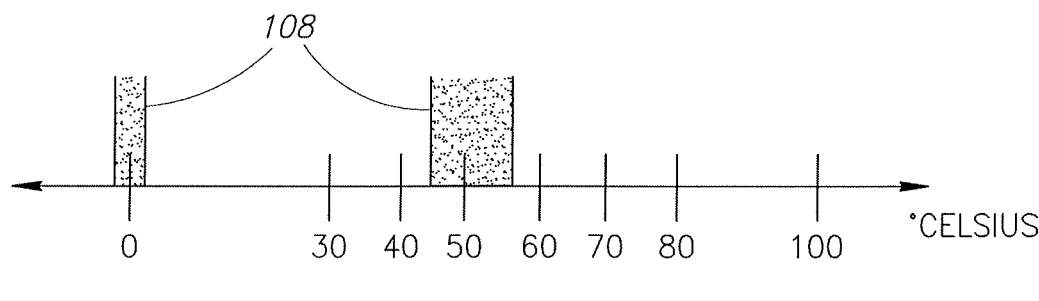
FIGS. 19A-C depict the temperatures of heating and their destructive nature. This can be altered by the duration of time that the target tissue is exposed to these temperatures and is dependent on the size and location of the target tissue that is being treated.

FIG. 19A is a depiction of the temperatures of heating and their destructive nature. This can be altered by the duration of time that the target tissue 1, 30 is exposed to these temperatures. In parathyroid gland 30 treatment, the optimal temperature and duration of exposure and the number of pulses differs from malignant tissue ablation since the acceptable percentage of cell cytolysis can be less with the FIG. 19B benign parathyroid 30 adenomas than with FIG. 19C a malignant tumor tissue. The zone of local vicinity tissue 17 exposures and risks for damage to that tissue from treatment of a malignant tumor is greater with the malignant tumor tissue than the benign tissue because the benign target tissue treatment can thus be directed and orchestrated to optimize the safety of local vicinity tissue 17 compared to target tissue 1, 30 because it is less necessary/critical to achieve high kill rates in the benign tissue compared to the malignant tissue especially with a single treatment. In one embodiment example the parathyroid gland 30 cytolysis is 70% and heating is 70 degrees C. for 10 minutes with 3 pulses and the local vicinity tissue damage is 1% whereas with the tumor the target tissue 1 for the malignant tumor killing is 99% and the temperature is 100 degrees C. for 10 minutes with 3 pulses but the local vicinity tissue damage is 30% or greater. This will vary depending on the size of the parathyroid gland 30 adenoma and its vicinity to critical local tissue 17 and the modality chosen to treat the parathyroid 30 adenoma.

FIG. 19A is a simplified temperature scale depicting that at approximately 46 degree to 56 degrees Celsius biological tissue begins to experience lethal thermal effects and sensitivity to cell death at equal or higher temperatures. At approximately 0 degrees Celsius or lower biological tissue begins to experience lethal thermal effects 108 and sensitivity to cell death at equal or lower temperatures.

Figure 19B:
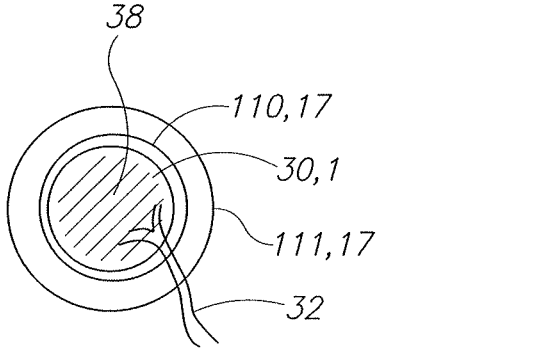

FIG. 19B depicts the parathyroid gland 30 target tissue 1 that is treated with TTMIT such that the parathyroid gland has 90% ablation 38 and the ablation 38 remains within the parathyroid gland 30 and the treatment can be effective and reduces the parathyroid gland 30 hormone elevated levels.

Figure 19C:
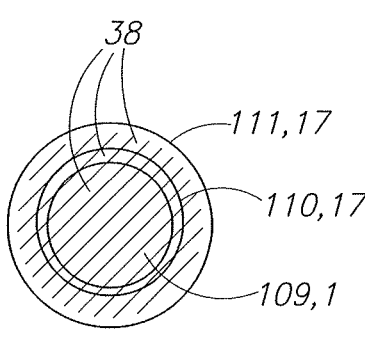

FIG. 19C depicts a tumor 109 target tissue 1 that is treated with MIT such that the tumor 109 to be fully treated or ablated 38 must include a 5-10% rim 110 of normal adjacent tissue 17 in order to have a reasonable possibility that the tumor has been ablated 38. To achieve this degree of ablation 38 and effective treatment this results in additional collateral damage to additional vicinity or local tissue 17 beyond the target tissue 109, 1 and beyond the 5-10% zone or rim 111, 17 around the tumor 109,1. In the treatment of a parathyroid adenoma 30 this form of MIT treatment would damage the local vicinity tissue such as non-parathyroid tissue such as but not restricted to arteries 32, veins 34 and nerves 19 and the trachea 46 and larynx 47.

FIG. 20 is a delivery device that can include but is not restricted to a tube/catheter or conduit 52, needle 58 or guide 50 that can have side holes 35 of variable size that can be greater in diameter proximal than distal or greater in diameter distal than proximal or any combination of sizes of side holes. In one embodiment the objective is for the side holes 35 to be greater diameter distally and smaller proximally such that if a substance 99 that can include a liquid is transported in the conduit 52 there will be more resistance to the proximal side hole 35 than the distal side holes 35 for the egress of the liquid/gel out of the conduit 52. In another embodiment the side holes 35 can be larger proximally to bath the local non-target tissue 17 with liquid/gel 77 or gas 77 and not deliver as much liquid/gel 77 or gas 77 to the target tissue 1, parathyroid gland 30. The substance can include but is not restricted to a solid 76 or liquid/gel 77 or gas 77. The end of the tube/conduit 52 can be open or closed. One use of this conduit/tube 52 with variable side holes 35 can be to deliver variable amounts of substance 99 or energy 100 to the tissue adjacent to the conduit/tube 52.

FIG. 21A is a tube or catheter or conduit, needle or guide, which can have a variable sized distal end hole, or the end of a conduit can be closed and contain no end-hole and be closed at the distal end. The conduits can be partially or fully composed of insulation and the insulation can include but is not restricted to insulation from electromagnetic, thermal, kinetic or mechanical forces or energy. In one embodiment a laser energy delivery device can reside within an insulator tube/catheter or conduit which can have a variable sized holes and can modulate or alter the lasers effect upon the target tissue, including the parathyroid gland. In FIG. 21B in one embodiment there can use side-holes or fenestrations that can be of variable size and shape including geometric and non-geometric and logarithmic and logarithmic paper shapes or cut-outs on a logarithmic pattern an can include one or more than one a tube/catheter or conduit, needle or guide, which can have a variable sized distal hole and a guide or sheath that is closed at the distal end and these insulating tubes or conduits can move or rotate to expose greater or lesser amounts of the energy treatment or substance for treatment to the target tissue, parathyroid gland. This embodiment can include a laser treatment device and two conduits that contain openings that can include but are not restricted to slits or holes that serve as fenestrations or windows to the laser light. When the conduit fenestrations are not aligned the amount of light or heat escaping the two conduits and reaching the target tissue is more limited than when the fenestrations are aligned. This can also be organized on a logarithmic graph pattern with cut out slits that can tightly control the amount of light that is emitted to the target tissue. A tube/catheter or conduit 52, needle 58 or guide 50, which can have a variable sized distal hole or a sheath 59 closed at the distal end. The insulation 43 can include but is not restricted to insulation from electromagnetic, thermal, kinetic or mechanical forces or energy. In one embodiment a laser energy delivery device 75 can reside within an insulator 43 tube/catheter or conduit 52, needle 58 or guide 50, which can have a variable sized distal hole or a sheath 59 closed at the distal end and the insulator 43 can modulate or alter the lasers effect upon the target tissue 1, including the parathyroid gland 30. In FIG. 21B in one embodiment this can be done using side holes 35 that can be of variable size and shape including geometric and non-geometric and logarithmic and logarithmic paper shapes or cut-outs on a logarithmic pattern 61. One or more than one a tube/catheter or conduit 52, needle 58 or guide 50, which can have a variable sized distal hole or a sheath 59 closed at the distal end 51 can be used and an insulating 43 device can move or rotate to expose greater or lesser amounts of the energy 100 or substance 99 treatment to the target tissue 1, parathyroid gland 30.

Figure 22:
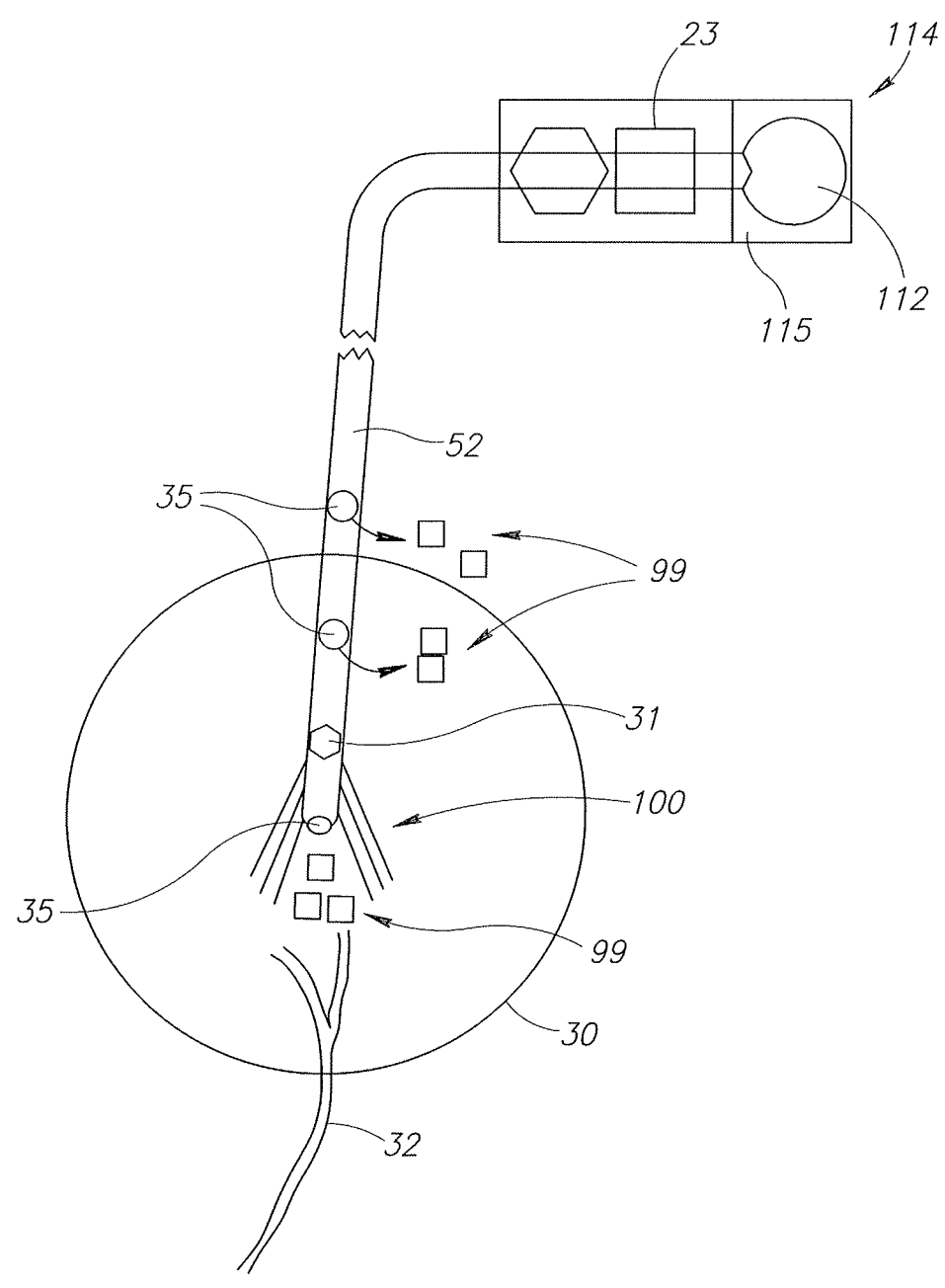
FIG. 22 is a device that delivers a substance to the target tissue, the parathyroid or the vicinity tissue. The substance is a substance that can modulate the function of the target tissue, the parathyroid. The device can include a pump and sensor that responds to physiologic parameters and the substance delivered can activate or deactivate the target tissue.

FIG. 22 is a treatment device that delivers a substance 99 to the target tissue 1, the parathyroid or the vicinity tissue 17. The treatment device 75 can deliver energy and can include a tube or conduit 52 that can include but is not restricted to a needle 58 or a hollow tube/conduit 52 that can include hole 35 such as side hole or end holes that can deliver a substance 99 to the parathyroid 99, target tissue 1 or the vicinity tissue 17. The substance 99 is a substance can modulate the function of the target tissue 1, the parathyroid 30 can include but is not restricted to peptides or peptide analogs to include but not restricted to portions of the parathyroid molecule which can include the active portion of the molecule or minerals such as Calcium or organic or inorganic compounds that can bind to receptors such as Sensapar (Cinacalcet), Sestamibi or Calcium analog compounds that are related to the parathyroid receptors that are the biological component that can include but are not restricted to the partial or the full parathyroid hormone or an added component as needed that can be used on the parathyroid binding receptors and can utilize methods for reversible or irreversible attachments. The delivery of the energy 100 or substance 99 can be performed manually or can include but is not restricted to a delivery device 114 that can include but is not restricted to contain a sensory controlling device that receives feedback from the organism's target gland 1, the parathyroid 30 or from the organism's blood or other organs or structures that contain biological feedback information with a sensor 31 that responds the physiologic nature of the organism (not shown) to include but not restricted to the blood calcium or ionize calcium levels or parathyroid levels and the delivery device 114 can include a pump 115 that can include a reservoir 112 and can include an energy generator 23 that can include but is not restricted to electromagnetic, mechanical, thermal, and kinetic energy In one embodiment if the parathyroid levels in the blood increase then a substance 99 such as but not restricted to calcium, Sestamibi, Sensapar (Cinacalcet) or calcium can be delivered to the tissue target 1, the parathyroid 30.

Figures 23A, 23B, 23C, 23D, 23E, 23F:
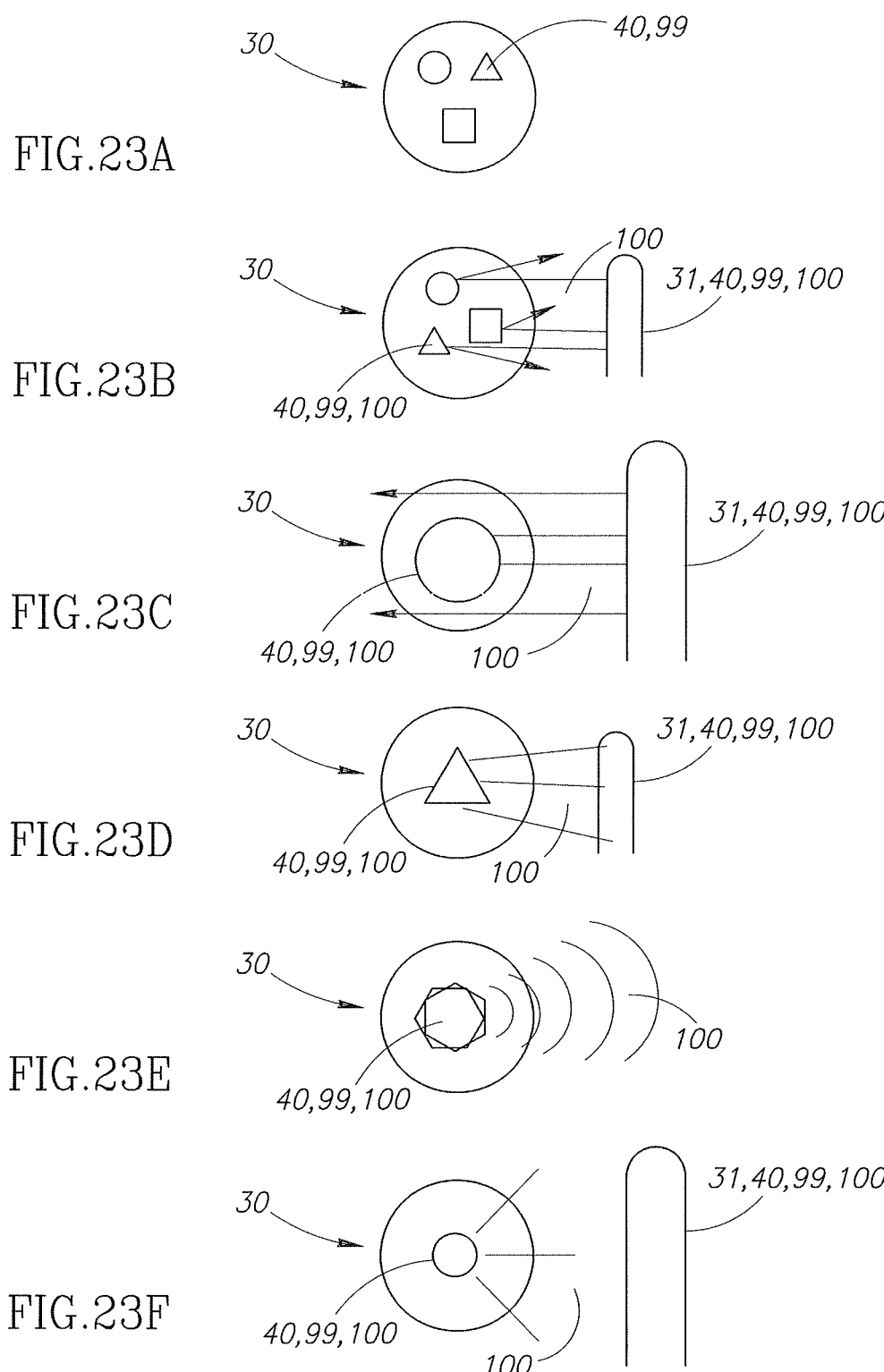
FIG. 23A is a target tissue marker or localizing device that can be used to include but not restricted to a surgical marker or localizing device, a percutaneous treatment marker or localizing device or a transcutaneous treatment marker or localizing device. The marker or localizing device can consist of a substance solid or liquid or gel or gas such as but not restricted to methylene blue and gentian violet, tattoo inks.
In FIG. 23B is a fluorescent or UV sensitive dyes, or fluorescein or in FIG. 23C an injected material can be metal or a radio-opaque material or FIG. 23D radioactive material or, in FIG. 23E, a GPS device or a FIG. 23F LED device. The marker or localizing device can be constructed to screw into the target tissue

FIG. 23A is a target tissue marker or localizing device that can be used to include but not restricted to a surgical marker or localizing device, a percutaneous treatment marker or localizing device or a transcutaneous treatment marker or localizing device. The marker or localizing device can consist of a substance solid or liquid or gel or gas such as but not restricted to methylene blue and gentian violet, tattoo inks. In FIG. 23B is a fluorescent or UV sensitive dyes, or fluorescein or in FIG. 23C an injected material can be metal or a radio-opaque material or FIG. 23D radioactive material or in FIG. 23E GPS device or a FIG. 23F LED device. The marker or localizing device can be constructed to screw into the target tissue. FIGS. 23A-F depict a target tissue 1, parathyroid 30 marker/localizing device 40 that can be used to include but not restricted to a surgical marker/localizing device, a percutaneous treatment marker/localizing device or a transcutaneous treatment marker/localizing device. The marker/localizing device 40 can consist of a substance 99 solid or liquid or gel or gas such as but not restricted to methylene blue and gentian violet, tattoo inks, fluorescent light or UV sensitive dyes which can include but are not restricted to nanoparticles to include but not restricted to Sol-gel derived silica is an excellent host material for creating fluorescent nanoparticles by the inclusion of covalently-bound organic dyes, Fluorophores that can be organic or inorganic, Fluorite (also called fluorspar) is a halide mineral composed of calcium fluoride, CaF2. Gemstones, minerals, may have a distinctive fluorescence or may fluoresce differently under short-wave ultraviolet, long-wave ultraviolet, or X-rays; calcite and amber will fluoresce under shortwave UV. Rubies, emeralds, and the Hope Diamond exhibit red fluorescence under short-wave UV light; diamonds also emit light under X ray radiation, Vitamin B2 (fluoresces yellow), quinine (blue), ninhydrin. And fluorescein or an injected material can be metal or a radio-opaque material that can be viewed with x-ray and can include but are not restricted to calcium, iodine, iron and other metals such as titanium, tungsten, barium sulfate, and zirconium oxide and in another embodiment the marker/localizing device can be a radioactive material that is low dose and used for diagnostic radiology that can include but is not restricted to technetium 99m, Iodine 123 and Iodine 131 or Sestamibi99mTc, which can be percutaneously injected directly into the Parathyroid gland. A percutaneous injection would have the advantage over intravenous sestamibi because of the lack of background counts in organs other than the Parathyroid gland 30 such as the local tissue 17, thyroid and fatty tissue and muscles. A radiation sensitive probe such as a pencil probe can be used to locate the Parathyroid gland during surgery more easily and the marker/localizing devices can contain a GPS device or contain a material that emits or provides for GPS detection.

The marker can include an LED device.

The marker or localizing device can have a shape that will pierce the target tissue but will offer resistance when it is attempted to remove the marker or localizing device. This can include but is not restricted to a corrugated or angulated or curved or spiral shape, a friction producing shape or a shape where target tissue becomes embedded in the marker. The resistance can be controlled such that it is not engaged or activated until the marker or localizing device lies within the target tissue, parathyroid. In one embodiment the marker can be composed of a metallic alloy such as nitinol that can straighten when thermally stressed with hot or cold and at biological temperatures is corrugated or angulated or curved or spiral in shape.

The marker or localizing device can be constructed to screw into the target tissue.

Figure 24A:
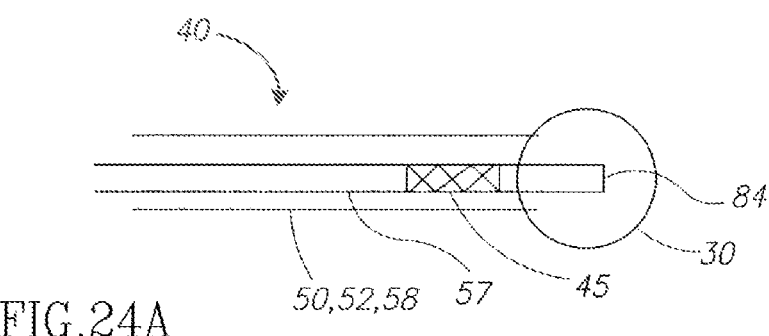
FIG. 24A is a guide/wire/placement device 70, a stylet 57 or a tube 52 or needle 58 that can leave a marker/localizing device 40 in the target tissue 1, parathyroid. In one embodiment, the marker/localizing device 40 can contain a transitional zone 45 that contains a transitional state sensitive substance 99 that can be converted from a solid or liquid/gel material that when exposed to a substance 99 or an energy source such as but not restricted to electromagnetic energy, kinetic or mechanical or thermal energy or forces changes its state and can separate from a more solid or gel state to a state where the placement device 70 is separated from the marker/localizing device 40. In one embodiment, the placement material and the transitional material and the marker/localizing device can all be metallic and if energy 100 such as an electrical current or a thermal force is transmitted though the placement wire the transitional zone 45 will separate from the marker/localizing device. In another embodiment the placement device material 70 can be composed of a gel that when cold 96 remains solid but when heated 98 the transitional zone will melt or dissolve after a given period of time and separate from the marker/localizing device 40.

FIG. 24A is a guide/wire/placement device 70, a stylet 57 or a tube 52 or needle 58 that can leave a marker/localizing device 40 in the target tissue 1, parathyroid. In one embodiment the marker/localizing device 40 can contain a transitional zone 45 that contains a transitional state sensitive substance 99 that can be converted from a solid or liquid/gel material that when exposed to a substance 99 or an energy source such as but not restricted to electromagnetic energy, kinetic or mechanical or thermal energy or forces changes its state and can separate from the a more solid or gel state to a state where the placement device 70 is separated from the marker/localizing device 40. In one embodiment the placement material and the transitional material and the marker/ localizing device can all be metallic and if energy 100 such as an electrical current or a thermal force is transmitted though the placement wire the transitional zone 45 will separate from the marker/localizing device. In another embodiment the placement device material 70 can be composed of a gel that when cold 96 remains solid but when heated 98 the transitional zone will melt or dissolve after a given period of time and separate from the marker/localizing device 40.

Figure 24B:
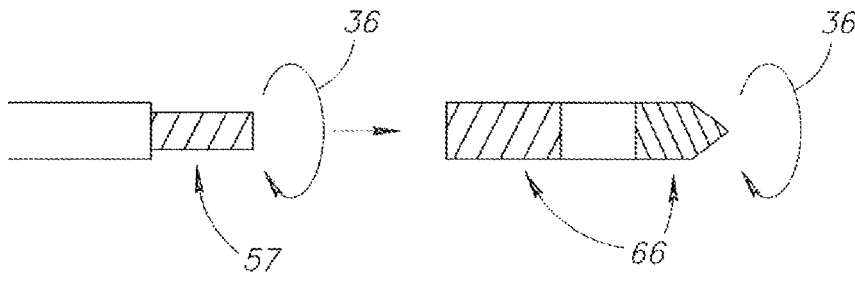
FIG. 24B is a placement device that can have groove/threads 66 that when turned or moved in the proper manner will unthread.

FIG. 24B is a placement device that can have groove/threads 66 that when turned or moved in the proper manner will unthread.

Figure 24C:
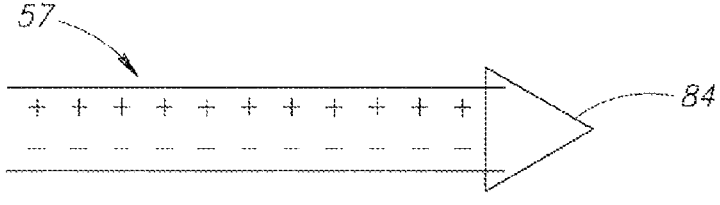
FIG. 24C is an embodiment where the gel can take on crystalline characteristics and become more rigid or less rigid when exposed to electromechanical or kinetic or mechanical energy.

FIG. 24C is an embodiment where the gel can take on crystalline characteristics and become more rigid or less rigid when exposed to electromechanical or kinetic or mechanical energy.

Figure 24D:
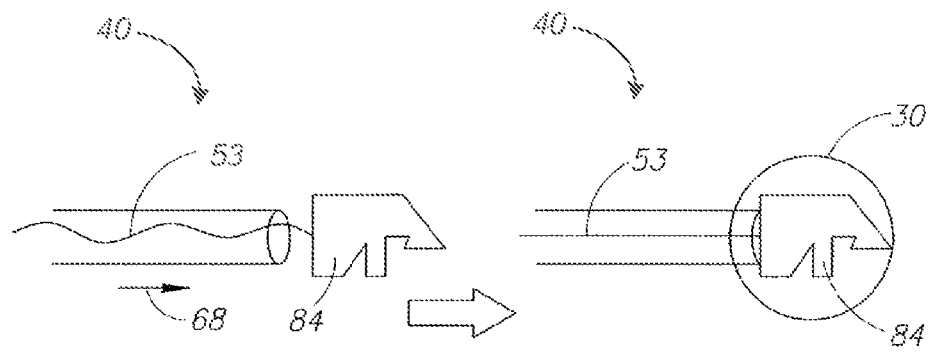
FIG. 24D is an embodiment of a marker/localizing device 40 that can be placed into the target tissue 1, the parathyroid gland 30, and the marker/localizing device can be attached to a continuous filament/thread 38 that can be made of a material that can be organic, which includes but is not restricted to silk, cotton or hemp or inorganic such as but not restricted to carbon filaments or metal.

FIG. 24D is an embodiment of a marker/localizing device 40 can be placed into the target tissue 1, the parathyroid gland 30 and the marker/localizing device can be attached to a continuous filament/thread 38 that can be made of a material that can be organic but not restricted to silk, cotton or hemp or inorganic such as but not restricted to carbon filaments or metal.

Figure 24E:
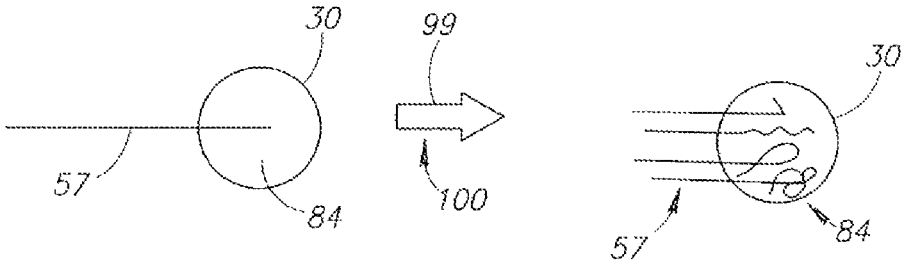
FIG. 24E is an embodiment of a marker/localizing device 40 can be placed into the target tissue 1, the parathyroid gland 30 that can be changed in shape by an energetic or thermal energy or substance 99 to include but not restricted to being straight to pierce the parathyroid 30 target tissue 1 and can take on a shape that creates resistance to being removed such as a corrugated shape.

FIG. 24E is an embodiment of a marker/localizing device 40 can be placed into the target tissue 1, the parathyroid gland 30 that can be changed in shape by and energetic or thermal energy or substance 99 to include but not restricted to being straight to pierce the parathyroid 30 target tissue 1 and can take on a shape that creates resistance to being removed such as a corrugated shape.

FIGS. 24A-E contain a guide or guide wire or placement device, a stylet or a tube or needle that can be left in or can leave a marker/localizing device in the target tissue, the parathyroid gland. In one embodiment the marker/localizing device can contain a transitional zone that when exposed to a substance or energy. The placement device can have groove/threads that when turned or moved in the proper manner will unthread. In one embodiment the gel can take on crystalline characteristics and become more rigid or less rigid when exposed to electromechanical or kinetic or mechanical energy. In another embodiment a marker/localizing device can be placed into the target tissue, the parathyroid gland 30 and the marker/localizing device can be attached to a continuous filament or thread that can be made of a material that can be organic but not restricted to silk, cotton or hemp or inorganic material such as but not restricted to carbon or carbon-carbon filaments, nylon or rayon, or plastic or metal. A marker or localizing device can have a shape that will pierce the target tissue but will offer resistance when it is attempted to remove the marker or localizing device. This can include but is not restricted to a corrugated or angulated or curved or spiral shape, a friction producing shape or a shape where target tissue becomes embedded in the marker. The resistance can be controlled such that it is not engaged or activated until the marker or localizing device lies within the target tissue, parathyroid. In one embodiment the marker can be composed of a metallic alloy such as nitinol that can straighten when thermally stressed with hot or cold and at biological temperatures is corrugated or angulated or curved or spiral in shape.

Figure 25A:
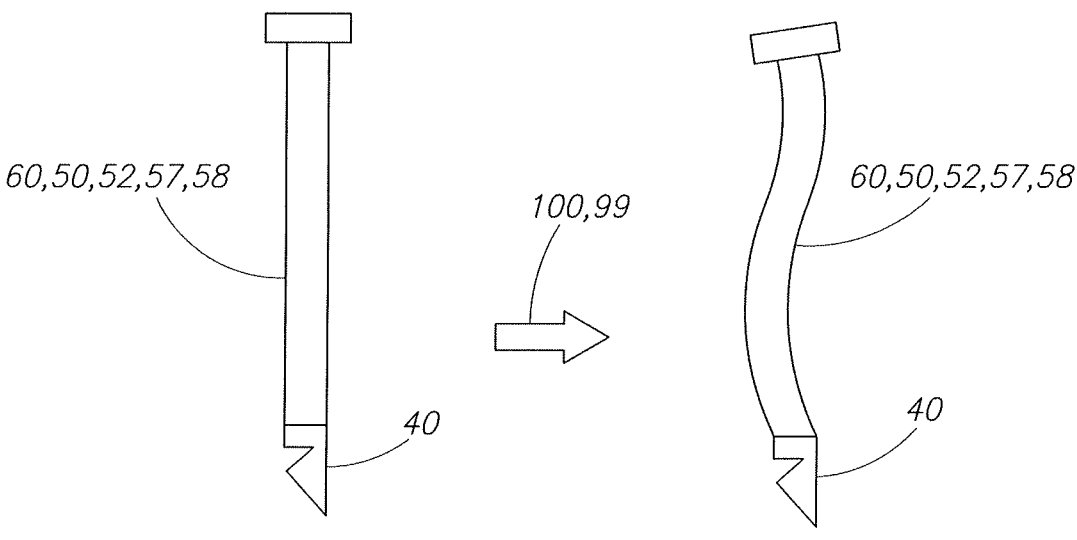
FIGS. 25A-B depict an embodiment in which a guide 50, guide wire 52, wire/thread 53, placement device 70, a stylet 57 or a tube 52 or needle 58 or hooks 60 or probes/tines/electrodes 94 can have transitional physical characteristics similar to and can be incorporated into the marker/localizing device but can also be used separately without a marker or localizing device.
Figure 25B:
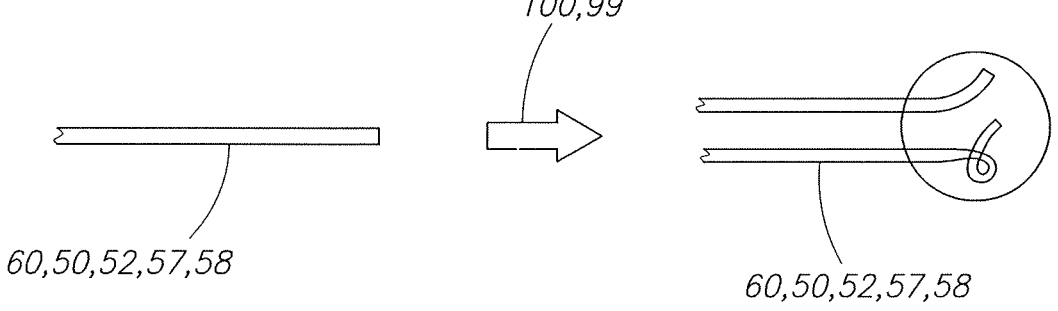

FIGS. 25A-B depict an embodiment in which a guide 50, guide wire 52, wire/thread 53, placement device 70, a stylet 57 or a tube 52 or needle 58 or hooks 60 or probes/tines/electrodes 94 can have transitional physical characteristics and can be composed of transitional materials that can include but are not restricted to metallic alloys such as but not restricted to nitinol, transitional gel and can be incorporated into the marker/localizing device 40 but can also be used separately without a marker or localizing device 40.

FIG. 25A depicts a tube/catheter or conduit 52, needle 58 or guide 50, guide 50, guide wire 52, wire/thread 53, placement device 70, or a stylet 57, that can be solid or hollow or can have one or more channels 54, 56 and when exposed to energy 100 or substance 99 that can include thermal energies such as but not restricted to cold becomes rigid and when exposed to heat becomes flexible.

FIG. 25B depicts a hook 60 or probes/tines/electrodes 94 that can be solid or hollow or can have one or more channels 54,54 and when exposed to energy 100 or substance 99 that can include thermal energies such as but not restricted to cold becomes rigid and when exposed to heat becomes flexible.

Figure 26A:
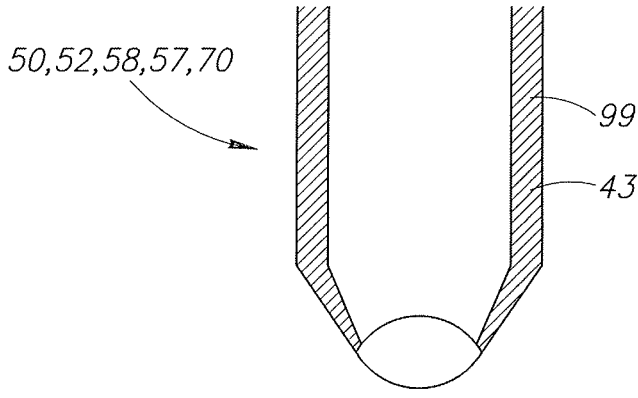
FIG. 26A is an insulated tube or catheter or conduit, needle or guide, guide wire, wire or thread, placement device, or a stylet; the insulation can be an insulation substance.
Figure 26B:
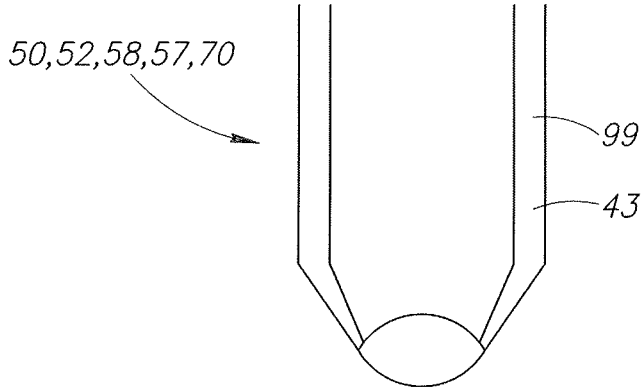
FIG. 26B depicts a chamber that can be filled with a substance that can insulate including a vacuum.
Figure 26C:
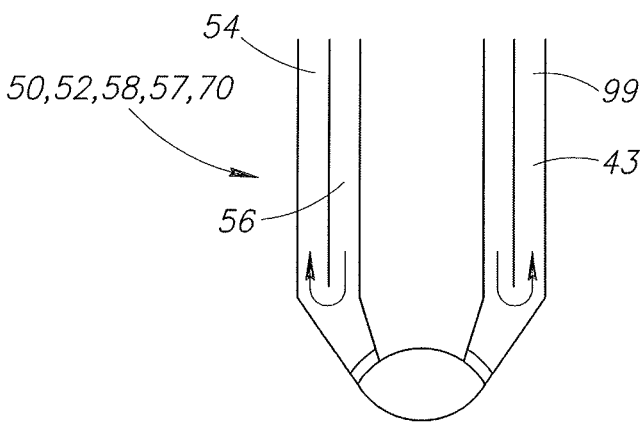
FIG. 26C depicts a substance that can circulate substances to form a heat sink.

FIGS. 26A-C depict an insulated tube/catheter or conduit 52, needle 58 or guide 50, guide 50, guide wire 52, wire/thread 53, placement device 70, or a stylet 57, insulation 43 can include but is not restricted to a vacuum FIG. 26A or a substance solid wall.

FIG. 26B or a wall with one 54 or more 56 channels. The insulation 43 can include a vacuum, or gases or liquids or gels or solids that can include but is not restricted to ceramic materials, high aluminum ceramics (Alumina Ceramic), beryllium, fiberglass, Zirconium, High Zirconium, adhesives and nansulators, reinforced carbon-carbon fiber construction (aka carbon-carbon, abbreviated C/C) is a composite material consisting of carbon fiber reinforcement in a matrix of graphite, Carbon fiber-reinforced silicon carbide (C/SiC) is a development of pure carbon-carbon (C/SiC utilizes silicon carbide with carbon fiber, and this compound is thought to be more durable than pure carbon-carbon), Fibrous refractory composite insulation (FRCI), LI-900 silica tiles, made from essentially very pure quartz sand, High-temperature reusable surface insulation (HRSI), Reaction Cured Glass (RCG), a nansulatecoating, Polytetrafluoroethylene (PTFE) or fluoropolymer of tetrafluoroethylene or a hypophillic or hydrophobic material, ultra-high-molecular-weight polyethylene (UHMWPE) or mineral oil or molybdenum disulfide embedded as additional lubricants in the needles matrix.

FIG. 26C is a chamber that can be filled with a substance 99 that can include a solid or liquid or gel or gas, or chambers that can circulate substances to form a heat sink can include are but not restricted to a substance 99 to include solids, liquids and gels and gasses or a vacuum.

Figures 27A, 27B:
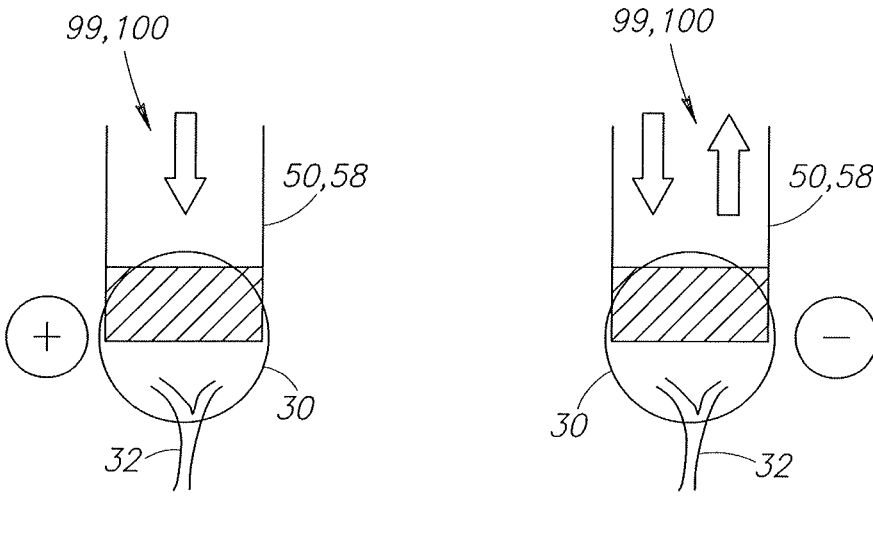
FIGS. 27A-B depict an embodiment in which a guide 50, guide wire 52, wire or thread, placement device, a stylet or a tube or needle is placed into or adjacent to the target tissue and hooks or probes/tines/electrodes can be used to maintain the position of the target tissue, parathyroid gland. In one embodiment FIG. 27A there can be a form of positive pressure created inside the target tissue 1, parathyroid gland 30. In another embodiment FIG. 27B the pressure exerted inside of the parathyroid can be negative pressure.

FIGS. 27A-B depict an embodiment in which a guide 50, guide wire 52, wire/thread 53, placement device 70, a stylet 57 or a tube 52 or needle 58 is placed into of adjacent to the target tissue a hooks 60 or probes/tines/electrodes 94 can be used to maintain the position of the target tissue 1, parathyroid gland 30. In one embodiment a form of positive pressure is created inside the target tissue 1, parathyroid gland 30. One embodiment can include but is not restricted to the placement of a substance 99 to include one or any combination of substances including but not restricted to solids 76, liquids 78 or gasses 77 or positive or negative pressure or vacuums into the target tissue 1, parathyroid gland 30. This can be used in combination or conjunction with an energy 100 device or source. In another embodiment the pressure exerted inside of the parathyroid can be negative pressure which can use of a substance 99 to include one or any combination of solids 76, liquids 78 or gasses 77 or a vacuum 79 exerted upon the target tissue 1, parathyroid gland 30. This can be used in combination or conjunction with an energy 100 device or source or a combination of positive and negative pressure. FIG. 27A represents overall positive pressure and FIG. 27B is negative pressure.

Figure 28:
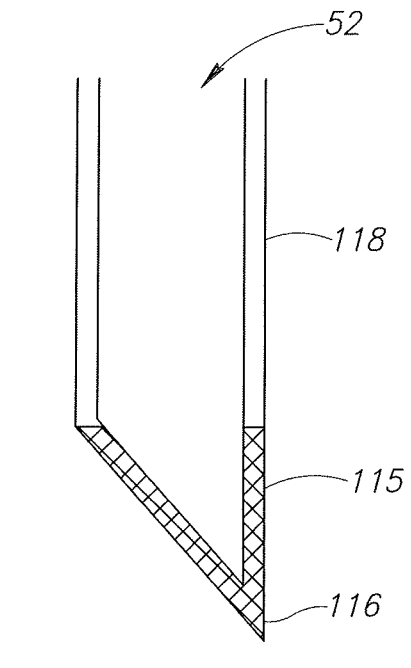
FIG. 28 is an embodiment of a guide, guide wire, wire or thread, placement device, a stylet or a tube or needle or hooks that can be composed of a carbon-carbon or ceramic based structure with a tensile strength that can be greater than, less than, or equal to an equivalent or similar device with the standard metal qualities for a similar use and that pierces the skin and subcutaneous tissue can be composed of a cutting material that can include but is not restricted to diamond or zirconium or hardened metal and can include but are not restricted to the leading edge or tip that has a sharpened cutting edge.

FIG. 28 is an embodiment of a tube or conduit 52 that can include but is not restricted to a guide 50, guide wire 52, wire/thread 53, placement device 70, a stylet 57 or needle 58 or hooks 60 that can be composed of a carbon-carbon or ceramic based structure with a tensile strength that can be greater than, less than, or equal to equivalent to a similar device with the standard metal qualities for a similar use. In one embodiment the component/s that pierce can be composed of but not restricted to diamond or zirconium and can include but are not restricted to the leading edge or tip 116. The surfaces inner or outer can be lubricated or made of a material with a low coefficient of friction 117. The transition between the body 118 of the tube or conduit 52 proximal to the tip 116 can be a hardened or reinforced 115 material.

FIGS. 29A-C depict an embodiment in which a form of delivery packets 103 or agitating 104 substance 99 can be used to increase or decrease the effect of an energy 100 source to the target tissue 1 and parathyroid gland 30. The delivery packets 103 or agitating 104 substance 99 can include but is not restricted to liposomes 101 or microbubbles 102.

FIG. 29A is an embodiment in which a form of delivery packets 106 or agitating substance 106 can be delivered percutaneously or non-percutaneously and can be used to deliver a substance 99, such as medication, to ablate the target tissue 30,1. In FIG. 29A the substance delivered through the delivery packet does not require a second substance 99 or energy source 100 for activation.

In FIG. 29B the substance 99 delivered through the agitation substance 106 or delivery packet 106 does require a second substance 99 or energy 100 source for activation.

In FIG. 29C the substance 99 delivered through the agitation substance 99 or delivery packet 106 does require a second substance 99 or energy source 100 for activation and the energy source can through a transcutaneous device 80 such as but not restricted to ultrasound and HIFU. In one embodiment agitation of the delivery packets 103 can create ablation and treatment of the target tissue 1, the parathyroid gland 30.

Figure 30:
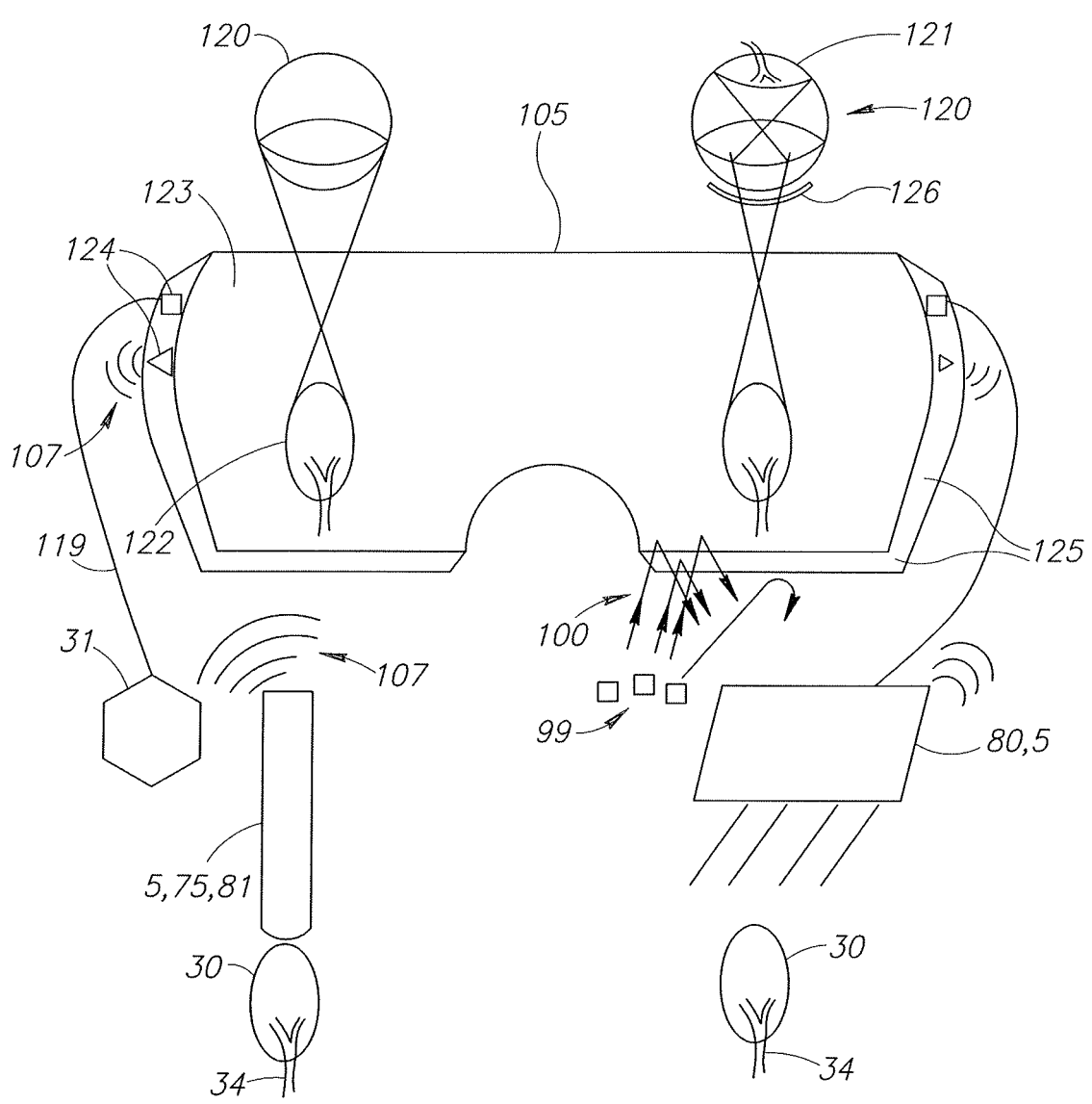
FIG. 30 is an embodiment of a viewing screen or display. In one embodiment the screen can be in the form of goggles or mask or glasses. Data and images can be displayed on the screen or projected from the goggles to the retina. The data can be transmitted by hardwiring or by non-wire methods, such as but not restricted to WI-FI. In addition, the goggles or mask or glasses display can also protect a portion of the user's body or face from harmful substances or from energy.

FIG. 30 is an embodiment of a viewing screen 105 that can be created to move with and/or track with the viewers' eyes 120 or head or body and in one embodiment can include but is not restricted to glasses/goggle/mask 105 that can serve as but is not restricted to a display, screen or visual representation 121, 122. The visual representations can include but are not restricted to displaying the images 122 or data 123 from an imaging device/s 5, 75, 81, 80 or the treatment device/s 75 or diagnostic devices 80, 81 or sensor or feedback devices 31 into receivers 124. Imaging sources can include imaging from but not restricted to ultrasound, MRI, CT scans, thermal or laser imaging. Data sources can include but are not restricted to energy 100 deposition, dimensional data such as length and width and depth, temporal data, devices engaged and sensor feedback 31. The data can be transmitted by hard-wiring 119 such as but not restricted to cables and fiber-optics and metal wires 119 or by non-wire sources 107 such as but not restricted to WI-FI. In addition, the display 105 can have the form of glasses/goggle/mask 105 that can also protect a portion of the surface or depth of the body or face or of the skin 6, 90. In one embodiment the viewers' face or portions of the face 109 can be protected from energy 100 or substances 99 that can include but are not restricted to organic or inorganic substances 99 or energy 100. In one embodiment the protective device 105 and the viewing device 105 can be combined or can be separate and can contain unique protections such as but not restricted to electromagnetic or insulating/thermal protections 43. In another embodiment the protective device 105 and/or the viewing device 105 can incorporate a seal or barrier 125 that can lie between the display/screen/goggles/glasses 105 and the user's skin or body part that can be airtight or watertight or can be breathable and non-airtight or watertight but provide a protective cushion or interface that prevents energy 100 or substances from reaching the user to include but not restricted to the user's skin 90 or eyes 120 or face or other body parts. A portion or all of the display/screen/goggles/glasses 105 can be opaque, transparent or translucent. The goggles can be especially hardened to resist mechanical debris 99 or energy 100. The display of the imaging of the parathyroid 30 target tissue 1 or data 123 can include but is not restricted to the image being displayed or projected on the screen 105 or can be displayed or projected onto the retina 121 or can be displayed onto an eternal lens such as but not restricted to a contact lens 126.

The general location of parathyroid glands inside a patient's neck skin and trans-cutaneous tissue and nerves. As illustrated, there are usually four, pea-sized parathyroid glands, usually located near the thyroids. In the present invention, devices, systems and methods for applying energy (percutaneously or transcutaneously) to a treatment location within, or adjacent, to one or more of these parathyroid gland, in order to ablate them, or alternatively, to increase glandular functioning (as facilitated by the application of non-ablative energy to said treatment location) are provided. These methods, systems and devices can further be employed as techniques and methods for treating a variety of parathyroid-based or related diseases, including but not limited to: hyperparathyroidism, hypercalcemia, and hypoparathyroidism.

For purposes of this disclosure, the parathyroid glands shall in general be referenced as 30.

For purposes of this disclosure, "ablation" refers to one or more of the following affects, including but not limited to: thermal tissue damage; tissue destruction; tissue shrinkage; tissue scarring; tissue swelling; tissue remodeling; resection or any process that results in the reduction or altered function, membrane disruption, altered blood flow, cellular death or de-bulking of the parathyroid gland 30.

In addition, "energy" refers to any form of energy, including various forms of electromagnetic energy, such as: radiofrequency (RF) energy; therapeutic ultrasound energy; microwave, laser, x-ray, or optical energy; magnetism, head and cryotherapy; or any combination thereof. Energy shall also refer to mechanical energy to include but not restricted to Brownian movement, heat, freezing, cryotherapy, cutting, tearing, crushing, spinning, piercing, poking prodding, dividing, removing and segregating or any combination thereof. Nevertheless, for ease of illustration, and not limitation, the specific devices and systems facilitating the treatment methods provided herein, in general employ RF or ultrasound energy or laser or piercing or mechanical energy to induce the desired effect in one or more glands. Medication refers to organic and non-organic agents to include but not restricted to solids 76, liquids 78 or gasses 77 that can ablate or alter the function of the parathyroid gland 30 directly or indirectly.

Altered function refers to either increasing or decreasing or modulating the function of the parathyroid gland 30.

Visualization of the anatomy can be performed using an imaging device 5 that can include but not restricted to ultrasound, x-ray, CT scans, MRI, visual or not visual light sources. The imaging device can include but is not restricted to percutaneous or can be transcutaneous intravascular.

A parathyroid gland 30 can be represented as a normal, an enlarged gland, a hyperplasic gland, an adenomatous gland and/or a hyper-functioning gland of the parathyroid 30. There are arterial blood vessels that create inflow 32 and veins 34 that provide outflow of blood from the parathyroid gland. The innervating nerves 19 of the parathyroid 30.

A device can be used to penetrate the skin 90 and the subcutaneous tissue 92 to reach the parathyroid gland. One embodiment can include a needle 58, which is pointed and has a guiding sheath 50, which allows repetitive access to the parathyroid tissue 30.

In one embodiment of treatment is percutaneous where a device punctures the skin 90 to access the parathyroid gland through the transdermal tissue 92. Such percutaneous access can utilize but is not restricted to the use of a needle 58 or guiding sheath/tube/catheter 52. Other forms of percutaneous access can include but are not restricted to a knife, a probe or a glass or plastic or fiber-optic tube. The puncture device can be hollow such as but not restricted to a tube. The puncture device can be solid such as but not restricted to a pointed needle 58, solid knife, member or probe.

A guiding sheath 50 can have a pointed or a blunt end 61. Inside of the sheath 50 can be a tube 52 that can have one 54 or more than one 56 channel for the introduction of solids 76, liquids 78 or gasses 77.

The guide stealth or introduction probe device can have rounded margins and can be but not restricted to a cylinder or ellipse or have pointed margins and can include but is not restricted to a needle 58 or catheter 50. The guide and introduction probe device can have but is not restricted to non-rounded margins and can be polygonal with multiple flat surfaces and can be but not restricted to triangular, a square, a rectangle or pentagon shaped or can have a combination of rounded and square surfaces or can be pointed with one of multiple pointed surfaces or can be pointed with one of multiple flat or blunt surfaces.

The guide/introduction probe device 50 can have one 54 or multiple channels 56. Said channels can be solid or hollow or can be a combination of solid and hollow. The hollow channel can be filled with or transmit a solid 76 or liquid 78 or gas 77. Each of the channels can have the same or different uses and purposes. One channel can be used for visualization of the parathyroid and the second channel can be utilized for treatment and/or treatment of the parathyroid. In another embodiment but not restricted to this embodiment, there can be two channels with one channel used for visualization of the parathyroid and the second channel can be utilized for biopsy of the parathyroid. Channels can have multiple combinations of uses.

In another embodiment but not restricted to this embodiment, there can be two channels one channel can be used for treatment of the parathyroid and the second channel can be utilized for biopsy of the parathyroid. In this example shown the visualization is external and one channel 54 is used for biopsy and the other channel is used for introduction of medication 99.

In another embodiment but not restricted to this embodiment, there can be more than two channels in which one channel can be used for treatment of the parathyroid and the second channel can be utilized for biopsy of the parathyroid and a third channel can be used for visualization (not shown). This visualization can be with a fiber-optic tube/camera, an ultrasound probe but is not restricted to ultrasound and/or fiber-optic visualization.

A guiding sheath 50 penetrating the parathyroid tissue 30 can have an accessory tube 52, which provides for the passage of solids 76, liquids 78 or gasses 77 material(s) 99. The tube 52 is in proximity to the parathyroid tissue 30 the artery 32 the nerve 19 and the vein 34. This provides for direct insinuation of the solids 76, liquids 78 or gasses 77 material into the parathyroid tissue 30 without leakage outside of the parathyroid gland 30. The tubes, which can include but are not restricted to the guiding sheath 50 and accessory tube 52 can, include methods for securing the tube to the tissue including permanent or retractable burs/projections and screw like threads.

In association with the sheath 50 there can be an additional tube 51, which provides for the passage of solid 76 or liquid 78 or gas 77 material(s) and can serve multiple functions to include but not restricted to insulation. The tube 52 is in proximity to the parathyroid tissue 30 the artery 32 and the vein or nerve (not shown). The solid device/probe/member can have multiple uses that include but are not restricted to treatment, localization and visualization of the parathyroid 30. Traversing the tube/conduit 52 is a solid device/probe/member that can be used to partially or fully ablate the parathyroid tissue 30 or the parathyroid arteries 32 or veins or nerve (not shown).

Methods for external device and internal probe/member/device 75 visualization can include but are not restricted to fiber-optic, ultrasound, thermographic, motion detection chromatography, blood flow detection, x-ray, ultraviolet, infrared as well as other detectors using the electromagnetic spectrum or kinetic/mechanical imaging or measuring devices. The visualization of the parathyroid 30 can occur on the skin 90 or within the body to include but not restricted to the subcutaneous tissue 92, blood vessels (34,32), hollow organs, orifices and other body parts (not shown) that can serve as windows of visualization.

The abnormal parathyroid 30 glands are usually an orange color and this unique quality can be used to visualize the abnormal parathyroid gland using a color/chromatographic detection technology to include but not restricted to transcutaneous, percutaneous, within the body or a combination of the above forms of imaging. The color identification system can involve using a light or energy source that is external or internal and that can be detected externally or internally or any combination of the above.

One method depicted in FIG. 6, is a probe/member/device 75 that can be used as a method for treatment of the parathyroid tissue 30 that can utilize a probe/member/device 75 that can include but not restricted to electromagnetic energy; radiofrequency energy; photoelectric energy; laser energy to include but not be restricted to hot lasers and cold lasers and intermediate lasers; ultraviolet energy, infrared energy, radioactive energy or x-ray energy in its various configurations.

In another method a probe/member/device 75 that can be used as a method for treatment of the parathyroid tissue 30 that can utilize a probe/member/device 75 that can include but not restricted to the forms of mechanical/kinetic energy including but not restricted to ultrasound energy including but not restricted to high frequency ultrasound (HIFU); heat, including but not restricted to laser directed heating; a direct heat source including but not restricted to metal or ceramic materials or a combination of different metals and ceramic materials; cold, including but not restricted to laser directed cooling or freezing device; a direct cooling or freezing source including but not restricted to metal or ceramic materials or a combination of different metals and ceramic materials; dry ice, hot or cold solids 76, liquids 78 or gasses 77.

With a sheath 50 penetrating the parathyroid tissue 30, there can be an additional tube 52, which provides for the passage of solids 76, liquids 78 or gasses material(s) and can serve multiple functions to include but not restricted to insulation. The tube 52 is in proximity to the parathyroid tissue 30 the artery 32 and the vein 34. Traversing the tube/conduit 70 can be a hollow device 75 that can be used to partially or fully ablate the parathyroid 30 or the parathyroid arteries 32 or veins (not shown) that can deliver one or any combination of solids 76, liquids 78 or gasses 77.

One method can include parathyroid treatment that can utilize but not restricted to the many forms of chemical agents to include solids 76, liquids 78 or gasses 77 that can include but are not restricted to sclerosing agents that can include but are not restricted to ETOH, Bleomycin, Tetracycline and Doxycycline; chemical reactions that induce heat or cold; direct injection or heated materials to include but not restricted to heated metal; direct injection of cooling or freezing agents to include but not restricted to dry ice solid carbon dioxide and liquid nitrogen; the expansion of tissue interrupting blood flow by increasing the tissues internal pressure such that the tissue pressure approached or exceeds arterial systolic and diastolic pressure or whereby the venous channels become obliterated thus trapping blood and preventing egress of blood outside of the parathyroid tissue thus decreasing both venous outflow and arterial inflow with agents to include but not restricted to water or gels (not shown) or solids 76, liquids 78 or gasses 77 to include but not restricted to oxygen, carbon dioxide and nitrogen. Agents that can poison the parathyroid tissue 30 can include but are not restricted to solids 76, liquids 78 or gasses 77 including but not restricted to ammonia, arsenic, acids and bases. The agents and techniques described in FIG. 7 can be directed to other tissue in the vicinity of the target tissue to include but not restricted to nerves 19 or subcutaneous tissue 92 to obtain similar effects.

Another method is the treatment of the parathyroid tissue, by introducing the treatment agent to the parathyroid gland 30 and local tissue 92, or at or in the parathyroid tissue 30 or the parathyroid feeding vessels 32,34 and nerves 19, including but not restricted to the arteries and veins can utilize but not restricted to bleeding agents and devices, such that the bleed occurs inside of the parathyroid and increases the pressure inside of the parathyroid and perturbs blood flow into or out of the parathyroid and ultimately destroys either a part or all of the parathyroid gland.

In another method, treatment of the parathyroid tissue can include introducing the treatment agent to the local tissue, or at or in the parathyroid tissue or the parathyroid feeding vessels 32,34, including but not restricted to the arteries 32 and veins 34 can utilize but not restricted to clotting agents and devices, such that the clot occurs inside of the parathyroid and increases the pressure inside of the parathyroid and perturbs blood flow into or out of the parathyroid and ultimately destroys either a part or all of the parathyroid gland 30.

In another method the treatment of the parathyroid tissue 30, by introducing the treatment agent to the local tissue 92, or at or in the parathyroid tissue 30 or the parathyroid feeding vessels (32, 34) or nerves 19, can utilize but not restricted to the many forms of poisoning of the parathyroid tissue to include but not restricted to chemical agents both inorganic and organic agents to include but not restricted to biological agents such as but not restricted to parathyroid directed antibodies or antibodies to the agents specific to the parathyroid; serum or blood that has incompatibility with the patient such as but not restricted to blood type A, B, O, AB or RH factors positive or negative; biochemical agents such as but not restricted to angiotoxic agents that damage blood vessels such as but not restricted to thalidomide; and inert agents to include but not restricted to chemical poisons such as but not restricted to arsenic, and sulfur. Expansile agents such as but not restricted to hydro-gels; bleeding agents such as platelet and clotting factor inhibitors; clotting agents such as but not restricted to kaolin and zeolite.

Another method is the treatment of the parathyroid tissue 30, by introducing the treatment agent to the local tissue 92, or at or in the parathyroid tissue 30 or the parathyroid feeding vessels (32, 34) or nerves 19, can utilize but not restricted to the many forms of macro, micro, and nano technology whereby the parathyroid tissue is disturbed in a manner that makes it non-functioning by using maceration of tissue, grinding of tissue, destruction of tissue through friction or cutting or piercing through mechanic methods or through the deposition of energy that can include but is not restricted to electromagnetic and kinetic/mechanical energy.

The treatment of the parathyroid tissue 30, by introducing the treatment agent to the local tissue 92, or at or in the parathyroid tissue 30 or the parathyroid feeding vessels (32, 34) or nerves 19, can utilize but not restricted to inject of antibodies in the blood stream that target the parathyroid 30. Organic and inorganic agents can be used that modulate or poison or make the parathyroid gland inactive or destroys a component or all of the parathyroid gland 30.

In another method the abnormal parathyroid gland 30 can be exposed to one of more treatment agent that can be activated when exposed to another treatment agent. In one example an energy activated poison can be activated when the parathyroid tissue 30 is exposed to energy that can include energies such as but not restricted to electromagnetic energy and kinetic/mechanical energy and can include but are not restricted to the photo sensitive or radioactive, ultrasonic or heat or cold sensitive poisons that are exposed to the proper electromagnetic spectral wavelength, ultrasonic wavelength, heat or cold from an external device (5, 80) or an internal device 75. In another example one agent can be protective and can modulate the treatment agent while the other agent can be the active treatment that. In another example one agent can be an adjuvant facilitating or increasing the effectiveness of the treating agent. In another example one agent can slow or stop the reaction of the treating agent.

In one embodiment the treatment of the parathyroid 30 can be performed using a coagulation agent's device. The coagulation agent's device can be on the skin 6 the coagulation agent's device can be external and separated from the skin with or without a membrane or substance that bridges the coagulation agents and the skin 6. The coagulation agent's device can be internal relative 92 to the body and below the surface of the skin 90. Coagulation agent's device can lie on or near the surface of the parathyroid in order to treat the parathyroid 30. The coagulation agent's device can puncture the parathyroid 30 to treat the parathyroid 30. The coagulation agent's device can lie on or near the surface of a parathyroid artery 32 or vein 34 in order to ablate the parathyroid blood flow. The coagulation agent's device 75 can puncture a parathyroid artery 32 or vein 34 in order to ablate the parathyroid blood flow. The coagulation agent's device can fully or partially ablate the parathyroid. The coagulation agent's device can fully or partially ablate the artery 32 or vein 34 to the parathyroid.

Antibody agent (anti-parathyroid antibody either produced from patients parathyroid or generic). In one embodiment the parathyroid treatment can be performed using an antibody agent. The antibody agent delivery device 75 can puncture the parathyroid to ablate the parathyroid. The antibody agent delivery device 75 can lie on or near the surface of a parathyroid artery 32 or vein 34 in order to treat the parathyroid blood flow. The antibody agent can puncture a parathyroid artery 32 or vein 34 in order to ablate the parathyroid blood flow. The antibody agent can fully or partially ablate the parathyroid the antibody agent can fully or partially ablate the artery or veins to the parathyroid. The antibody agent can be delivered systemically to include but not restricted to being delivered in an artery 32 or vein 34.

In one embodiment the treatment of the parathyroid 30 can be performed using a medication delivery system device (75, 77, 80). Medication can include but is not restricted to sclerosing agents, Sensipar, antibodies, modulating agents to include but not restricted to agents that stimulate the parathyroid genome, and Calcium and Vitamin D that suppress the protective agents such as but not restricted to anti-radiation and anti-oxidation agent, bases and acids. The medication delivery system device (75, 80) can be on the skin. The medication delivery system device (75, 80) can be external and separated from the skin with or without a membrane or substance that bridges the medication delivery system device (75, 80) and the skin 90. Medication delivery system device (75, 77, 80) can be internal relative to the body 92 and below the surface of the skin 90. Medication delivery system device (75, 80) can lie on or near the surface of the parathyroid in order to ablate the parathyroid. The medication delivery system device (75, 80) can puncture the parathyroid to ablate the parathyroid 30. The medication delivery system device (75, 80) can lie on or near the surface of a parathyroid arteries 32 or veins 34 in order to ablate the parathyroid blood flow. The medication delivery system device (75, 80) can puncture a parathyroid arteries 32 or veins 34 in order to ablate the parathyroid blood flow. The medication delivery system device (75, 80) can fully or partially ablate the parathyroid the medication delivery system device (75, 80) can fully or partially ablate the artery or veins to the parathyroid. The medication delivery system device (75, 80) can deactivate the parathyroid either by destroying the gland rapidly or over a more prolonged period of time. The medication delivery system can decrease parathyroid functions without destroying the gland. The medication can be titrated to insure proper parathyroid levels within the body. The medication delivery device can treat the local tissue 92, the nerves 19, the arteries 32 or veins 34. The medication can be protective to the parathyroid 30 or it can modulate function or it can be destructive.

One embodiment can include but is not restricted to an energy delivery device 75, 80 for ablating one or more parathyroid glands 30. The energy delivery device 75, 80 delivers energy 100 to ablate parathyroid tissue 30 preferably while surrounding tissues 17, anatomical structures (including, e.g., nerves 19, vessels 32, thyroids 20) are preserved. In one possible embodiment, energy delivery device 75, 80 comprises an elongated member having an energy 100 delivery member disposed at a distal end thereof. In one possible implementation, one or more lumens extend through a portion, or the entire length, of elongated member and are configured as pathways for the used for the delivery of delivery of solids 76, liquids 78 or gasses 77. The energy delivery device is deliverable though a transcutaneous device 80 allowing for the minimally invasive, or non-invasive, ablation of the parathyroid glands 30. The energy delivery member can be coupled to energy generator 23. In this embodiment, the energy delivery device 80 and the energy delivery device can be coupled together. In this embodiment, energy delivery device 26 comprises other device components; including controller 7 coupled to feedback sensors disposed on the distal end of energy delivery device.

In one embodiment the device uses electromagnetic energy 100 for either diagnostic or therapeutic purposes. The energy is directed at a body tissue to include but not restricted to the parathyroid 30 and can be directed toward its vascular supply including the arteries 32, veins (not shown) and the nerves. The electromagnetic energy can pass through the skin 6 and subcutaneous tissue 92. In one embodiment one of the channels can be used for localization/visualization of tissue 27.

In one embodiment of an energy delivery device delivers energy to ablate tissue of the target tissue, preferably while surrounding tissues, anatomical structures (including, e.g., nerves 19, vessels 32, thyroids 20, 22) adjacent glands 30 are preserved.

In one possible embodiment, the energy delivery device 80 comprises an elongated member having an energy delivery member that can be exposed at its distal end. In one possible implementation the active component of the energy delivery probe can use cables or connectors, catheters, guidewires, pullwires, insulated wires, optical fibers, and/or imaging devices, feedback systems, to expose the energy delivery component relative to the insulated component. In a preferred embodiment, the energy delivery device is deliverable though an imaging device through a tube or conduit 52 or guide 50 and can include but is not restricted to an endoscope, catheter, and introducer device, allowing for the tightly targeted minimally invasive, or non-invasive, ablation of target tissue 1. The energy delivery probe can be coupled to an energy generator 23.

In one embodiment, an energy delivery member, or at least a portion or that device, can be directly inserted into gland 30 to facilitate contact between the delivery device probe and the target tissue 1, the parathyroid gland.

In another embodiment, energy delivery member may be a RF probe comprising a monopolar or bipolar or multipolar electrode(s) coupled to a distal end of a probe. The distal end of the RF probe can be configured to be directly inserted into parathyroid gland 30 facilitating direct contact between the one or more RF electrodes and glandular tissue 30.

As will be readily appreciated by one skilled in the art, several techniques can be implemented to facilitate identification and location of glands 30 to be treated or ablated. In one possible implementation, and as a described in U.S. Pat. No. 6,263,232, glands 30 may be identified and located through radio-labeling and employing one or more radioactivity sensors coupled to energy delivery device to detect them. In the present, preferred embodiment, energy delivery device comprises one or more radioactivity sensors coupled to the distal end; thus allowing for detection of a radiolabel administered to the patient prior to, or during, the treatment procedure and accumulated in glands 30 facilitating identification, location and treatment thereof.

In yet another possible implementation, standard visualization techniques, including: ultrasound; MRI; and/or CT imaging (just to name a few), can be separately or simultaneously employed to aid in the identification and location of parathyroid glands 30 to be treated or ablated. In this embodiment, the energy delivery device is image-guided to the appropriate location where energy delivery can be initiated. A user viewable monitor is coupled to energy delivery device to facilitate image-guidance of energy delivery device.

In yet another embodiment, image and radio-guidance techniques can be implemented together to ensure identification, location and position of energy delivery device.

In yet another embodiment, energy delivery device comprises other device components, including controller coupled to feedback sensors disposed on the distal end of energy delivery device. Controller is configured to receive and process one or more signals from feedback sensors disposed on the distal end of energy delivery device. Feedback sensors provide signals, which can be processed to regulate one or more of the following processes, including but not limited to: energy delivery; extent of tissue ablation; termination of energy delivery, etc. Said feedback sensors can be configured to detect, and/or, monitor, for example, tissue temperatures, tissue impendence, electrical signals or nerve impulses. Yet another feedback mechanism, which can be employed to regulate one or more of the processes described above, includes periodic vocalization from the patient, before, during or after the treatment. As will be readily appreciated by those skilled in the art, period vocalization can be used to ensure no or minimal vocal cord paralysis as a result of treatment.

In a further embodiment, a patient's parathyroid hormone serum levels and/or calcium levels can also be monitored (before, during and/or after treatment) to assist in the regulation of the energy delivery process, as well as, determine the appropriate extent of tissue ablation or stimulation. For instance, parathyroid gland 30 can be ablated until a detectable decrease in a patient's parathyroid hormone or calcium levels are reached. Alternatively, glands 30 can be stimulated until an increase in a patient's parathyroid hormone levels are detected.

One general method of using energy delivery device includes advancing a guiding catheter, endoscope, introducer or other like device through, a preferably small puncture or incision on the patient's skin until the distal tip of said catheter/endoscope/introducer is seated adjacent to the parathyroid gland 30 to be treated. Image and/or radio-guidance, as provided above, can be employed to position said catheter/endoscope/introducer adjacent gland 30 to be treated.

Energy delivery device is then introduced though the catheter/endoscope/introducer and the distally located energy delivery member positioned to affect ablation or treatment of the parathyroid gland 30. When energy delivery device or energy delivery member is adequately positioned, energy, for example high frequency electrical energy, to include but not restricted to MW, IRE, laser and in the RF range, is directed through energy delivery member to the one or more RF electrodes or probes to the parathyroid gland 30 to ablate the target tissue or form an ablative lesion of a desired size and shape. Typically high frequency electrical energy levels of about 5 to about 100 Watts, preferably about 30 to about 70 Watts, are suitable to ablate tissue. Typical lesions formed are about 3 mm to about 20 mm in diameter and about 3 mm to about 20 mm in length. As will be readily apparent to one skilled in the art, these operational parameters can be modified and the system configured in order to facilitate the suitable partial or whole ablation of one or more parathyroid glands. Other generally suitable devices and system that can also be employed are described in U.S. Pat. No. 6,016,452, U.S. application Ser. No. 10/621,839, U.S. Pat. No. 6,494,886 the contents of which are hereby incorporated by reference. As discussed, various feedback sensors and monitoring techniques may be employed to regulate or monitor energy delivery.

Another implementation of energy delivery device for the partial or complete ablation of one or more parathyroid glands 30. In this embodiment, energy delivery device is configured as a percutaneously inserted probe 24 as described in co-pending U.S. patent application Ser. No. 10/671,417 filed Sep. 24, 2003, the contents of which are hereby incorporated by reference in their entirety. Similar to energy delivery device, probe is preferably configured to be introducible though an endoscope, catheter, introducer or other like device to facilitate the non-invasive, or minimally invasive, delivery of said probe. As further described in co-pending U.S. patent application Ser. No. 10/671,417, insertable probe 24 can be used to ultrasonically ablate tissue using therapeutic ultrasound energy or high intensity focused ultrasound energy ("HIFU" energy). As described above, the probe, is image and/or radio-guided to glands 30 and one or more feedback mechanisms is employed for purposes of: controlling energy delivery, ensuring controlled ablation of tissue, determining an endpoint of the treatment, etc. as provided above. The probe can house at a minimum therapeutic acoustic transducers (or emitters), which, when actuated by an energy generator 23, transmit therapeutic ultrasound or HIFU energy sufficient to ablate glandular tissue.

Another embodiment of energy delivery device allows for the transcutaneous ablation of the parathyroid gland 30. As will be readily appreciated by one skilled in the art, one of the design advantages of utilizing therapeutic ultrasound energy or high intensity focus ultrasound ("HIFU") is that the ultrasound energy may be deposited to a remote location without damaging intervening tissues or structures. This is accomplished by focusing the therapeutic ultrasound energy or HIFU to a focal location as generally HIFU employs high-intensity convergent, or "focused," ultrasound energy, or beams (generated by a high power ultrasound transducers or therapeutic transducers), to affect tissue heating and ablation. In this implementation, HIFU is intended to allow ablation of parathyroid tissue without damaging intervening and surrounding tissue, eliminating the need for incisions or insertion of devices, etc. and any resulting complications. Moreover, the size or volume of tissue to be ablated may be optimized and/or changed depending on the specific operational parameters (frequency, phasing/timing, voltages) or drive strategies employed to activate the high power or therapeutic transducer. General descriptions of various therapeutic or HIFU devices and systems that generally may be adopted to ultrasonically ablate a parathyroid gland are provided in U.S. Pat. Nos. 5,354,258; 5,150,711; 6,685,639; 6,508,774; 6,217,530; 5,995,875; 6,016,452; 6,666,835; and 6,656,136 the entire contents of which are hereby incorporated by reference.

An energy delivery device is adapted to transcutaneously focus therapeutic ultrasound energy to a focal location within a parathyroid gland to ablate tissue. In this embodiment, energy delivery device generally comprises an ultrasound applicator housing at least one ultrasound transducer or transducer assembly configured to emit therapeutic ultrasound energy or HIFU when actuated by an energy generator. The ablative therapeutic ultrasound energy or HIFU energy is delivered through a patient's skin to the treatment location on the gland. The treatment, or duration in which energy is applied, can change or be optimized according to the amount, extent or volume of tissue 30 to be ablated.

Generally, the ultrasound applicator is placed against the patient's neck and configured to be hand-held for easy manipulability.

As with the other devices, the transcutaneous energy delivery device can incorporate various other devices and system components which may aid in the identification and localization of glands and/or for the controlled delivery of ablative energy. In one embodiment, energy delivery device can be configured to allow for image-guidance of the therapeutic ultrasound energy to the gland 30. In yet another embodiment, radio-guidance of the therapeutic ultrasound energy may be implemented. Various strategies that can be further implemented for directing the appropriate amount or dose of therapeutic ultrasound energy to treat or ablate one or more glands 30 are provided in U.S. Pat. Nos. 4,922,917; 6,425,867; and 6,726,627 the entire contents of which are hereby incorporated by reference.

In accordance with yet another aspect of the invention, devices and systems described herein can be adapted to allow for the delivery of non-ablative energies thus facilitating the stimulation of glandular function and providing a treatment for hyperparathyroidism.

While the present invention has been described in detail with reference to preferred embodiments thereof, it will be apparent to one skilled in the art that various changes can be made, and equivalents employed, without departing from the scope of the invention. For example, the described methods can be implemented for the treatment of other glands, such as the adrenal gland.

In another embodiment a device that uses electromagnetic or mechanical energy for either diagnostic or therapeutic purposes. The energy is directed at a body tissue to include but not restricted to the parathyroid 30 and can be directed toward its vascular supply which can include the arteries 32, the veins (not shown) or the nerves 19. The electromagnetic or mechanical energy 82 can pass through the skin 90 and subcutaneous tissue 92. A delivery tube/needle 84 can penetrate the skin 90 and subcutaneous tissue 92 and the target tissue to include but not restricted to the parathyroid 30 and its vascular supply and nerves (not shown, in this embodiment the arteries 32. A solid 76, liquid 78 or a gas 77 substance or a combination of these substances can be delivered to the parathyroid. In one embodiment the guidance of the needle and substance placement is visualized or measured by the device 80. In another embodiment the device 80 can activate or deactivate the solid 76, liquid 78 or a gas 77 substance. More than one device or delivery tube/needle can be used or multiple combinations of these devices or delivery tube/needles 52, 58 or electromagnetic or mechanical energies 80 can be used (not shown). The local subcutaneous tissue 92 and nerves 19 can be modified using by the delivery of energy 80 or substance 99, non-energetic methods to protect the local tissue which in this embodiment is the subcutaneous tissue.

In one embodiment the parathyroid gland may be over functioning, normal functioning or under functioning. A method for modulation which can include stimulation or reduction or cessation of the parathyroid gland 30 is described which can be temporary or permanent. A form of parathyroid pacemaker can be used to modulate the parathyroid function. This can be used for the treatment of an overactive parathyroid causing osteoporosis or an underactive parathyroid or a normal parathyroid that needs to be stimulated to induce bone growth and development. Even though the parathyroid gland when over-active will reduce bone mineral, the parathyroid gland 30 does control osteoclast and osteoblast activity and when timed and dosed in the proper many can induce an equilibrium that may increase bone growth. This can be done using parathyroid hormone release alone or in combination with organic substances such as but not restricted to parathyroid hormone, calcitonin, growth hormone, peptides, hydroxyapatite and can be use with inorganic substances such as but not restricted to Calcium, Phosphorus and other bone minerals. The substances and the stimulation can be used together in multiple combinations and with multiple temporal relations or stimulation and delivery.

In one embodiment energy which can include but is not restricted to electromagnetic and mechanical energy and can be used to stimulate the parathyroid gland 30. This can be performed by stimulating the nerves 19, the arteries 32, the veins 34 and the parathyroid tissue 30 or any combination of these structures.

In one embodiment, non-energy substances, which can include but is not restricted to parathyroid hormone, a component of the parathyroid hormone, a new derivative peptide with the elements of the parathyroid hormone and contains the active amino acid sequence, and neurotransmitters can be used to stimulate the parathyroid gland 30. This can be performed by stimulating the nerves 19, the arteries 32, the veins 34 and the parathyroid tissue 30 or any combination of these structures.

The modulation, activating and de-activating methods which include but are not restricted to medication/substance or energy source can be instilled into the parathyroid or around the parathyroid or from the skin in a transcutaneous manner.

In one embodiment the energy source and the energy can be placed on the skin or near the skin but not through the skin near the parathyroid.

In this embodiment a substance/medication that has been delivered to the parathyroid must be activated or de-activated by the energy source. The delivery method of the substance can be but is not restricted to a delivery method that includes through a blood vessel (intravenous or intra-arterial); or through a needle to include through the skin or subcutaneous tissue; or via a transcutaneous method. The substance/medication 99 can utilize and organic substance such as but not restricted to a targeted antibody or cell receptor; or a non-organic substance such as but not restricted to an element or molecule such as but mot restricted to Calcium; a medication to include but not restricted to sestamibi or Sensipar (cinacalcet).

In one embodiment there can be more than one substance that must act in concert with the energy to prevent local tissue damage. These substances can be dependent upon each other for activation prior to, after or during energy activation.

In another embodiment the energy source and the energy can be placed or delivered to or near the parathyroid using a percutaneous; transcutaneous technique such that the energy source is within; or in direct contact with the parathyroid; or intimate but not into or in direct contact with the parathyroid gland.

In another embodiment, the energy source and the energy can be placed through a blood vessel and delivered to or near the parathyroid using a technique such that the energy source is within; or in direct contact with the parathyroid; or intimate but not into or in direct contact with the parathyroid gland.

In one embodiment there can be one or multiple energy sources.

In another embodiment there can be one or multiple medication/substances.

By combining one or a combination of substances and one or a combination of energies or energy sources or one or more delivery systems the parathyroid can be modulated, activated, de-activated or even ablated over time from disuse and the ablation can be partial or complete or the parathyroid can be induce to grow and increase its function especially in patients with under-active parathyroid glands which can occur but not restricted to aggressive surgical resection, transplantation of the parathyroid gland 30, or prior radiation that damages the parathyroid gland 30.

One embodiment can include a method to activate or de-activate the treatment effect on the parathyroid 30 and surrounding tissue 17 or can have any combination or modulation or variation of activation and deactivation on the parathyroid 30 or local tissue 17 by altering the effects of the medication/substance or energy source on the parathyroid 30 or local tissue 17. The treatment agent can be energy and can include but is not be restricted to electromagnetic or mechanical/kinetic energy. The treatment agent can be a substance that can be but is not restricted to a medication that can be but is not restricted to organic or non-organic and can be instilled into the parathyroid gland 30 or around the parathyroid local tissue 17 by using a method that can be but is not restricted to a percutaneous technique to include but not restricted to a needle; an osmotic method to include but not restricted to DMSO or ultrasonic activated lipophilic packets or UV light on a cement-like or glue like material to include UV light and glass ionomer cement (GIC). In one embodiment, the energy source and the energy and the treatment agent can be placed on the skin 6 or near the skin but not through the skin 6, 90.

In another embodiment, the energy source and the energy and the treatment agent can be placed through the skin/percutaneous. In another embodiment, the energy source and the energy and the treatment agent can be placed in any combination of through the skin/percutaneous 92 or not through the skin but rather on the skin (6, 90). In one embodiment a treating substance/medication that has been delivered to the parathyroid must be de-activated by the energy source. The delivery method of the substance can be but is not restricted to a delivery method that includes through a blood vessel (intravenous or intra-arterial); or through a needle to include through the skin or subcutaneous tissue; or via a transcutaneous method. The substance/medication can utilize and organic substance such as but not restricted to a targeted antibody or cell receptor; or a non-organic substance such as but not restricted to an element or molecule such as but mot restricted to Calcium; a medication to include but not restricted to sestamibi or Sensipar (cinacalcet).

In one embodiment there can be more than one substance that must act in concert with the energy to activate or deactivate or cause or prevent local tissue damage. These substances can be dependent upon each other for activation or deactivation. Prior to or after or during energy application.

In another embodiment, The energy source and the energy can be placed or delivered to or near the parathyroid using a percutaneous; transcutaneous technique such that the energy source is within the parathyroid tissue 30; or in direct contact with the parathyroid gland 30; or intimate but not into or in direct contact with the parathyroid gland 30.

In another embodiment The energy source and the energy can be placed through a blood vessel and delivered to or near the parathyroid using a technique such that the energy source is within; or in direct contact with the parathyroid; or intimate but not into or in direct contact with the parathyroid gland.

In one embodiment there can be one or multiple energy sources.

In another embodiment there can be one or multiple medication/substances.

By combining one or a combination of substances and one or a combination of energies or energy sources, the parathyroid 30 can be ablated partially or completely, the parathyroid 30 can be activated or de-activated or the surrounding tissue 92 and vital structures to include but not restricted to the vital nerves 19 can be protected or partially or completely ablated or injured.

One embodiment uses a protective material in the zone around the parathyroid 30 that can be activated with or without another substance/medication or energy and facilitates the protection of the local tissue 17 which can include but is not restricted to a weak base if an acid is used to ablate the parathyroid 30.

One embodiment uses a destructive material in the parathyroid 30 that can be activated with or without another substance/medication or energy and facilitated the destruction of the parathyroid which can include but is not restricted to UV light and glass ionomer cement to ablate the parathyroid 30.

In one embodiment the treatment can be performed by Radio Frequency Ablation Device (RFAD). Utilizing parathyroid imaging including an internal device 75 or an external device 80 that can include but is not restricted to ultrasound device directed to identify the hyper-functioning parathyroid gland 30.

Examples of methods of treatment can include but are not restricted to:

In one embodiment the treatment device can include but is not restricted to an RF treatment device in which the energy is directed into the body utilizing imaging that can include but is not restricted to ultrasound and the RF energy is focused to treat the organ to include but not restricted to the parathyroid gland 30.

In one embodiment the treatment can be performed using an internal device 75. The Radiofrequency device can be internal relative to the body and below the surface of the skin (6, 90) and within the body parts that can include but is not restricted to subcutaneous tissue, hollow organs, blood vessels, orifices and other body parts or a combination of these body parts that provide access to the parathyroid 30. The Radiofrequency device can lie on or near the surface of the parathyroid in order to treat the parathyroid 30. The Radiofrequency device 75 can puncture the parathyroid 30 to treat the parathyroid or it can enter a body part that is a hollow organ or orifice or a combination of these body parts. The Radiofrequency device can lie on or near the surface of a parathyroid artery or vein in order to treat the parathyroid 30. The Radiofrequency device can puncture a parathyroid artery or vein in order to ablate the parathyroid blood-flow. The Radiofrequency device can fully or partially ablate the parathyroid 30 The Radiofrequency device can fully or partially ablate the artery or veins or nerves to the parathyroid or damage the local tissue in and near the parathyroid 30.

In another embodiment the Radiofrequency device 75 can be on the skin. The Radiofrequency device 75 can be external 80 and separated from the skin with or without a membrane or substance that bridges the Radiofrequency and the skin.

In one embodiment the treatment can be performed by High Frequency Ultrasound (HIFU) utilizing parathyroid imaging including an internal device 75 or an external device 80 that can include but is not restricted to ultrasound device directed to identify the hyper-functioning parathyroid gland 30.

In one embodiment the treatment device can include but is not restricted to an HIFU treatment device in which the energy is directed into the body utilizing imaging that can include but is not restricted to ultrasound and the HIFU energy is focused to treat the organ to include but not restricted to the parathyroid gland 30.

In one embodiment the treatment can be performed using an internal device 75. The HIFU device can be internal relative to the body and below the surface of the skin (6, 90) and within the body parts that can include but is not restricted to subcutaneous tissue, hollow organs, blood vessels, orifices and other body parts or a combination of these body parts that provide access to the parathyroid 30. The HIFU device can lie on or near the surface of the parathyroid in order to treat the parathyroid 30. The HIFU device 75 can puncture the parathyroid 30 to treat the parathyroid or it can enter a body part that is a hollow organ or orifice or a combination of these body parts. The HIFU device can lie on or near the surface of a parathyroid artery or vein in order to treat the parathyroid 30. The HIFU device can puncture a parathyroid artery or vein in order to ablate the parathyroid blood-flow. The HIFU device can fully or partially ablate the parathyroid 30 The HIFU device can fully or partially ablate the artery or veins or nerves to the parathyroid or damage the local tissue in and near the parathyroid 30.

In another embodiment the HIFU device can be on the skin. The HIFU device can be external and separated from the skin with or without a membrane or substance that bridges the HIFU and the skin.

An Electromagnetic device (EMD) can include but is not restricted to Radiofrequency ablation (RF) and microwave (MW) and laser (L), Cryotherapy (CryT), High Intensity Focused Ultrasound (HIFU), Radioactive Therapy (Brachytherapy: BrT), Irreversible Electroporation (IRE), Electrical Current Therapies, Electrocautery, Magnetic Resonance (MR), Ultrasound, (US), Thermal energies both heat 98 and cold 96. And EMD can be used with mechanical or kinetic energies and with adjuvant combinations that can include but are not restricted to medication delivery, Medication packets, blood flow reduction, Chemical and Medication Ablation, Activation and Deactivation and Modulation Therapy, Adhesives and Glues and Molecular Crystal and Lattice therapies, Target Tissue Delivery Device Therapies, Peptide and Biological Conversion Therapies, MR and RF and Magnetic External Heating Therapies, Hyperthermia with Adjuvant Therapy, Hypothermia with Adjuvant Therapy, Local protective therapy in the Vicinity of the Target Organ Therapy, Suction and Expansion Therapy, Positive Pressure and Expansion Therapy, Mechanical Ablation Therapy and Combinations of Therapies.

In one embodiment the ablation can be performed using an Electromagnetic Energy Delivery Device (EMED). The EMED can deliver continuous energy The EMED can deliver non-continuous energy including but not restricting to pulsed energy. The EMED can deliver continuous energy that can be modulated to increase or decrease the energy delivered. The EMED can deliver non-continuous energy that can be modulated to increase or decrease the energy delivered.

In one embodiment the treatment can be performed by (EMED) utilizing parathyroid imaging including an internal device 75 or an external device 80 that can include but is not restricted to ultrasound device directed to identify the hyperfunctioning parathyroid gland 30.

In one embodiment the treatment device can include but is not restricted to an EMED treatment device in which the energy is directed into the body utilizing imaging that can include but is not restricted to ultrasound and the EMED energy is focused to treat the organ to include but not restricted to the parathyroid gland 30.

In one embodiment the treatment can be performed using an internal device 75. The EMED device can be internal relative to the body and below the surface of the skin (6, 90) and within the body parts that can include but is not restricted to subcutaneous tissue, hollow organs, blood vessels, orifices and other body parts or a combination of these body parts that provide access to the parathyroid 30. The EMED device (75, 80) can lie on or near the surface of the parathyroid in order to treat the parathyroid 30. The EMED device 75 can puncture the parathyroid 30 to treat the parathyroid or it can enter a body part that is a hollow organ or orifice or a combination of these body parts. The EMED device can lie on or near the surface of a parathyroid artery or vein in order to treat the parathyroid 30. The EMED device can puncture a parathyroid artery or vein in order to ablate the parathyroid blood-flow. The EMED device can fully or partially ablate the parathyroid 30 The EMED device can fully or partially ablate the artery or veins or nerves to the parathyroid or damage the local tissue in and near the parathyroid 30.

In another embodiment the EMED device 80 can be on the skin. The EMED device can be external and separated from the skin with or without a membrane or substance that bridges the EMED and the skin.

In one embodiment the ablation can be performed using a laser device. The laser device can be a Laser (Hot or Cold or Intermediate) Device.

In one embodiment the treatment can be performed by a laser utilizing parathyroid imaging including an internal device 75 or an external device 80 that can include but is not restricted to ultrasound device directed to identify the hyperfunctioning parathyroid gland 30.

In one embodiment the treatment device can include but is not restricted to a laser treatment device in which the energy is directed into the body utilizing imaging that can include but is not restricted to ultrasound and the laser energy is focused to treat the organ to include but not restricted to the parathyroid gland 30.

In one embodiment the treatment can be performed using an internal device 75. The laser device can be internal relative to the body and below the surface of the skin (6, 90) and within the body parts that can include but is not restricted to subcutaneous tissue, hollow organs, blood vessels, orifices and other body parts or a combination of these body parts that provide access to the parathyroid 30. The laser device 75 can lie on or near the surface of the parathyroid in order to treat the parathyroid 30. The laser device 75 can puncture the parathyroid 30 to treat the parathyroid or it can enter a body part that is a hollow organ or orifice or a combination of these body parts. The laser device can lie on or near the surface of a parathyroid artery or vein in order to treat the parathyroid 30. The laser device can puncture a parathyroid artery or vein in order to ablate the parathyroid blood-flow. The laser device can fully or partially ablate the parathyroid 30 The LASER device can fully or partially ablate the artery or veins or nerves to the parathyroid or damage the local tissue in and near the parathyroid 30.

In another embodiment the laser device 80 can be on the skin. The laser device can be external and separated from the skin with or without a membrane or substance that bridges the laser and the skin.

In one embodiment the ablation can be performed using a mechanical/kinetic/vibrational energy (KME) device which can include but is not restricted to the use or production of heat 98 or cold 96 or Brownian or vibrational motion.

In one embodiment the treatment can be performed by (KME) utilizing parathyroid imaging including an internal device 75 or an external device 5 that can include but is not restricted to ultrasound device directed to identify the hyperfunctioning parathyroid gland 30.

In one embodiment the treatment device can include but is not restricted to a KME treatment device in which the energy is directed into the body utilizing imaging that can include but is not restricted to ultrasound and the KME energy is focused to treat the organ to include but not restricted to the parathyroid gland 30.

In one embodiment the treatment can be performed using an internal device 75. The KME device can be internal relative to the body and below the surface of the skin (6, 90) and within the body parts that can include but is not restricted to subcutaneous tissue, hollow organs, blood vessels, orifices and other body parts or a combination of these body parts that provide access to the parathyroid 30. The KME device 75 can lie on or near the surface of the parathyroid in order to treat the parathyroid 30. The KME device 75 can puncture the parathyroid 30 to treat the parathyroid or it can enter a body part that is a hollow organ or orifice or a combination of these body parts. The KME device can lie on or near the surface of a parathyroid artery or vein in order to treat the parathyroid 30. The KME device can puncture a parathyroid artery or vein in order to ablate the parathyroid blood-flow. The KME device can fully or partially ablate the parathyroid 30 The KME device can fully or partially ablate the artery or veins or nerves to the parathyroid or damage the local tissue in and near the parathyroid 30.

In another embodiment the KME device 80 can be on the skin. The KME device 80 can be external and separated from the skin with or without a membrane or substance that bridges the KME and the skin.

In one embodiment the ablation can be performed using a Thermal device which can be a heating energy device. In one embodiment the method of therapy is to cauterize the parathyroid and/or the parathyroid feeding arteries.

In one embodiment the treatment can be performed by heating or warming utilizing parathyroid imaging including an internal device 75 or an external device 5 that can include but is not restricted to ultrasound device directed to identify the hyper-functioning parathyroid gland 30.

In one embodiment the treatment device can include but is not restricted to a heating treatment device in which the energy is directed into the body utilizing imaging that can include but is not restricted to ultrasound and the heating energy is focused to treat the organ to include but not restricted to the parathyroid gland 30.

In one embodiment the treatment can be performed using an internal device 75. The heating device can be internal relative to the body and below the surface of the skin (6, 90) and within the body parts that can include but is not restricted to subcutaneous tissue, hollow organs, blood vessels, orifices and other body parts or a combination of these body parts that provide access to the parathyroid 30. The heating device can lie on or near the surface of the parathyroid in order to treat the parathyroid 30. The heating device 75 can puncture the parathyroid 30 to treat the parathyroid or it can enter a body part that is a hollow organ or orifice or a combination of these body parts. The heating device can lie on or near the surface of a parathyroid artery or vein in order to treat the parathyroid 30. The heating device can puncture a parathyroid artery or vein in order to ablate the parathyroid blood-flow. The heating device can fully or partially ablate the parathyroid 30. The heating device can fully or partially ablate the artery or veins or nerves to the parathyroid or damage the local tissue in and near the parathyroid 30.

In another embodiment the heating device can be on the skin. The heating device can be external and separated from the skin with or without a membrane or substance that bridges the HEATING and the skin.

In one embodiment the treatment can be performed using a thermal device to include a cooling/freezing device.

In one embodiment the treatment can be performed by a cryotherapy or cooling/freezing device utilizing parathyroid imaging including an internal device 75 or an external device 80 that can include but is not restricted to ultrasound device directed to identify the hyper-functioning parathyroid gland 30.

In one embodiment the treatment device can include but is not restricted to a cooling/freezing treatment device in which the energy is directed into the body utilizing imaging that can include but is not restricted to ultrasound and the cooling/freezing energy is focused to treat the organ to include but not restricted to the parathyroid gland 30.

In one embodiment the treatment can be performed using an internal device 75. The cooling/freezing device can be internal relative to the body and below the surface of the skin (6, 90) and within the body parts that can include but is not restricted to subcutaneous tissue, hollow organs, blood vessels, orifices and other body parts or a combination of these body parts that provide access to the parathyroid 30. The cooling/freezing device can lie on or near the surface of the parathyroid in order to treat the parathyroid 30. The cooling/freezing device 75 can puncture the parathyroid 30 to treat the parathyroid or it can enter a body part that is a hollow organ or orifice or a combination of these body parts. The cooling/freezing device can lie on or near the surface of a parathyroid artery or vein in order to treat the parathyroid 30. the cooling/freezing device can puncture a parathyroid artery or vein in order to ablate the parathyroid blood-flow. The cooling/freezing device can fully or partially ablate the parathyroid 30 the cooling/freezing device can fully or partially ablate the artery or veins or nerves to the parathyroid or damage the local tissue in and near the parathyroid 30.

In another embodiment the cooling/freezing device can be on the skin. The cooling/freezing device can be external and separated from the skin with or without a membrane or substance that bridges the cooling/freezing and the skin (6, 90).

In one embodiment the treatment can be performed by a mechanical ablation device utilizing parathyroid imaging including an internal device or an external device that can include but is not restricted to ultrasound device directed to identify the hyper-functioning parathyroid gland 30.

In one embodiment the treatment device can include but is not restricted to a mechanical ablation treatment device in which the energy is directed into the body utilizing imaging that can include but is not restricted to ultrasound and the mechanical ablation energy is focused to treat the organ to include but not restricted to the parathyroid gland 30.

In one embodiment the treatment can be performed using an internal device 75. The mechanical ablation device can be internal relative to the body and below the surface of the skin (6, 90) and within the body parts that can include but is not restricted to subcutaneous tissue, hollow organs, blood vessels, orifices and other body parts or a combination of these body parts that provide access to the parathyroid 30. The mechanical ablation device can lie on or near the surface of the parathyroid in order to treat the parathyroid 30. The mechanical ablation device 75 can puncture the parathyroid 30 to treat the parathyroid or it can enter a body part that is a hollow organ or orifice or a combination of these body parts. The mechanical ablation device can lie on or near the surface of a parathyroid artery or vein in order to treat the parathyroid 30. The mechanical ablation device can puncture a parathyroid artery or vein in order to ablate the parathyroid blood-flow. The mechanical ablation device can fully or partially ablate the parathyroid 30 the mechanical ablation device can fully or partially ablate the artery or veins or nerves to the parathyroid or damage the local tissue in and near the parathyroid 30.

In another embodiment the mechanical ablation device can be on the skin. The mechanical ablation device can be external and separated from the skin with or without a membrane or substance that bridges the mechanical ablation and the skin (6, 90).

The mechanical ablation device can be formed such that the majority of sharp or cutting edges are enclosed and that only a small element or aspect of the cutting surface is exposed this can include but is not restricted to a tube with a side hole where the mechanical ablation occurs. The mechanical ablation can include blades, cutting elements to include but not restricted to diamonds or other gems or stones, other solids liquids or gasses. These ablative tools can be performing their task under equal, greater or less pressure than the body's internal pressure.

Parathyroid ablation can be directed at the parathyroid tissue, at the local tissue, to the nerves or at or to the parathyroid feeding vessels, including but not restricted to the parathyroid tissue, arteries and veins.

In one embodiment the ablation can be performed using a radioactive substance/radioactive seeds device.

In one embodiment the treatment can be performed using a radioactive substance including but not restricted to radioactive seeds device (63, 64, 65).

In one embodiment the treatment can be performed by a radioactive substance including but not restricted to radioactive seeds device utilizing parathyroid imaging including an internal device or an external device that can include but is not restricted to ultrasound device directed to identify the hyper-functioning parathyroid gland 30.

In one embodiment the treatment device can include but is not restricted to an radioactive substance including but not restricted to radioactive seeds treatment device in which the energy is directed into the body utilizing imaging that can include but is not restricted to ultrasound and the radioactive substance including but not restricted to radioactive seeds energy is focused to treat the organ to include but not restricted to the parathyroid gland 30.

In one embodiment the treatment can be performed using an internal device 75. The radioactive substance including but not restricted to radioactive seeds device can be internal relative to the body and below the surface of the skin (6, 90) and within the body parts that can include but is not restricted to subcutaneous tissue, hollow organs, blood vessels, orifices and other body parts or a combination of these body parts that provide access to the parathyroid 30. The radioactive substance including but not restricted to radioactive seeds device can lie on or near the surface of the parathyroid in order to treat the parathyroid 30. The radioactive substance including but not restricted to radioactive seeds device 75 can puncture the parathyroid 30 to treat the parathyroid or it can enter a body part that is a hollow organ or orifice or a combination of these body parts. The radioactive substance including but not restricted to radioactive seeds device can lie on or near the surface of a parathyroid artery or vein in order to treat the parathyroid 30. The radioactive substance including but not restricted to radioactive seeds device can puncture a parathyroid artery or vein in order to ablate the parathyroid blood-flow. The radioactive substance including but not restricted to radioactive seeds device can fully or partially ablate the parathyroid 30 the radioactive substance including but not restricted to radioactive seeds device can fully or partially ablate the artery or veins or nerves to the parathyroid or damage the local tissue in and near the parathyroid 30.

In another embodiment the radioactive substance including but not restricted to radioactive seeds device can be on the skin. The radioactive substance including but not restricted to radioactive seeds device can be external and separated from the skin with or without a membrane or substance that bridges the radioactive substance including but not restricted to radioactive seeds and the skin (6, 90).

In one embodiment the ablation can be performed using a laparoscopic removal system device, which can include but is not restricted to laparoscopic surgery. The laparoscopic system can utilize but is not restricted to a led to light the field and fiber-optic viewing, fiber-optic lighting and viewing simultaneously, a tube or channel placed percutaneously.

In one embodiment the treatment can be performed using a laparoscopic removal system device.

In one embodiment the treatment can be performed by using a laparoscopic removal system device, utilizing parathyroid imaging including an internal device or an external device that can include but is not restricted to ultrasound device directed to identify the hyper-functioning parathyroid gland 30.

In one embodiment the treatment device can include but is not restricted to an laparoscopic removal system treatment device in which the energy is directed into the body utilizing imaging that can include but is not restricted to ultrasound and the laparoscopic removal system energy is focused to treat the organ to include but not restricted to the parathyroid gland 30.

In one embodiment the treatment can be performed using an internal device. The laparoscopic removal system device can be internal relative to the body and below the surface of the skin 6 and within the body parts that can include but is not restricted to subcutaneous tissue, hollow organs, blood vessels, orifices and other body parts or a combination of these body parts that provide access to the parathyroid 30. The laparoscopic removal system device can lie on or near the surface of the parathyroid in order to treat the parathyroid 30. The laparoscopic removal system device can puncture the parathyroid 30 to treat the parathyroid or it can enter a body part that is a hollow organ or orifice or a combination of these body parts. The laparoscopic removal system device can lie on or near the surface of a parathyroid artery or vein in order to treat the parathyroid 30. The laparoscopic removal system device can puncture a parathyroid artery or vein in order to ablate the parathyroid blood-flow. The laparoscopic removal system device can fully or partially ablate the parathyroid 30 the laparoscopic removal system device can fully or partially ablate the artery or veins or nerves to the parathyroid or damage the local tissue in and near the parathyroid 30.

In another embodiment the laparoscopic removal system device can be on the skin. The laparoscopic removal system device can be external and separated from the skin with or without a membrane or substance that bridges the laparoscopic removal system and the skin 6, 90.

In one embodiment the treatment can be performed using a pressure/suction ablation system device.

In one embodiment a pressure device is constructed to create negative pressure on the parathyroid gland 30. This negative pressure reduces the venous 34 outflow from the parathyroid gland 30 and increases the capillary bed pressure and decreases arterial 32 inflow. As a result, the parathyroid tissue 30 will undergo necrosis from a loss of arterial 32 inflow and tissue edema and loss of venous 34 outflow, which creates cell death and necrosis.

In another embodiment a pressure device is constructed to create positive pressure on the parathyroid gland 30. This positive pressure reduces the venous 34 outflow from the parathyroid gland 30 and increases the capillary bed pressure and decreases arterial 32 inflow. As a result, the parathyroid tissue 30 will undergo necrosis from a loss of arterial 32 inflow and tissue edema and loss of venous 34 outflow, which creates cell death and necrosis.

In one embodiment the treatment can be performed by a pressure/suction ablation system device utilizing parathyroid imaging including an internal device or an external device that can include but is not restricted to ultrasound device directed to identify the hyper-functioning parathyroid gland 30.

In one embodiment the treatment device can include but is not restricted to an pressure/suction ablation system treatment device in which the energy is directed into the body utilizing imaging that can include but is not restricted to ultrasound and the pressure/suction ablation system energy is focused to treat the organ to include but not restricted to the parathyroid gland 30.

In one embodiment the treatment can be performed using an internal device 75. The pressure/suction ablation system device can be internal relative to the body and below the surface of the skin 6, 90 and within the body parts that can include but is not restricted to subcutaneous tissue, hollow organs, blood vessels, orifices and other body parts or a combination of these body parts that provide access to the parathyroid 30. The pressure/suction ablation system device can lie on or near the surface of the parathyroid in order to treat the parathyroid 30. The pressure/suction ablation system device 75 can puncture the parathyroid 30 to treat the parathyroid or it can enter a body part that is a hollow organ or orifice or a combination of these body parts. The pressure/suction ablation system device can lie on or near the surface of a parathyroid artery or vein in order to treat the parathyroid 30. the pressure/suction ablation system device can puncture a parathyroid artery or vein in order to ablate the parathyroid blood-flow. The pressure/suction ablation system device can fully or partially ablate the parathyroid 30 the pressure/suction ablation system device can fully or partially ablate the artery or veins or nerves to the parathyroid or damage the local tissue in and near the parathyroid 30.

In another embodiment the pressure/suction ablation system device can be on the skin. The pressure/suction ablation system device can be external and separated from the skin with or without a membrane or substance that bridges the pressure/suction ablation system and the skin 6.

In one embodiment, the coordination of robotic surgery with the above techniques and imaging can be combined.

In another embodiment, a method for treatment of the parathyroid gland can include implanting a substance into the parathyroid gland 30 which can include but not restricted to a ferromagnetic substance which when stimulated by an outside energy source to include but not restricted to magnetic resonance ultrasound, electromagnetic energy, which can be external to the skin 6 or percutaneous. The substance in the preferred embodiment can create heat and cauterize the injected tissue.

The primary substance can also be non-active in its primary state but when exposed to an outside energy source is activated either by an organic or non-organic reaction which can include but is not restricted to forming a new compound or creating energy within the parathyroid gland 30 that can include but is not restricted to heat or a mechanical ablative process such as gyration or vibration. The energy source, activating compound, the primary substance or any combination of the above can be delivered external to the skin 6. The energy source can be delivered internal to the skin 92 within the body. The delivery can include but is not restricted to percutaneous.

In another embodiment a nanotechnology device can be implanted into the parathyroid gland 30 that can perform the treatment of the parathyroid gland 30 and can be used in combination with but not restricted to Radio Frequency Ablation Device (RFAD) Ultrasound High Frequency, Ultrasound (HIFU) Device, Electromagnetic Energy/Wave Delivery Device, Laser (Hot or Cold or Intermediate) Device, Mechanical/kinetic Energy/Vibration Device, Heating Energy/Cauterizing Device, Cooling/Freezing Device, Medication, Sclerosing Device.

In another embodiment to protect the local tissue an introducer 50 for the guidance or delivery system can be composed of material that insulates the surrounding tissue from the treatment agent to include but not restricted to insulation of the surrounding tissue from Radio Frequency Ablation Device (RF, RFAD), Ultrasound High Frequency Ultrasound (HIFU) Device, Electromagnetic Energy/Wave Delivery Device, Laser (Hot or Cold or Intermediate) Device, Mechanical/kinetic Energy/Vibration Device, Heating Energy/Cauterizing Device, Cooling/Freezing Device, Medication and Sclerosing Device.

In another embodiment the treatment system can be combined with a guidance system to include but not restricted to: Ultrasound, Computerized Tomography (CT), Magnetic Resonance Imaging (MR/MRI), X-ray and other Electromagnetic Energy imaging methods to include but not restricted to: Ultraviolet and Infrared, Thermography/Heat Detection, Blood Flow detection devices, Positron Emission Tomography, Nuclear Medicine Imaging, Magnetic Imaging, Or a combination of any of the listed methods.

In another embodiment, prior to the parathyroid treatment a percutaneous biopsy can be performed. The introducer 50 can be used to facilitate the biopsy such that the biopsy and ablation are all performed through the introducer 50 or channels (54, 56).

In another embodiment, an Abnormal Parathyroid Gland 30 can be detected when it has a rich blood supply and with this produces greater proportional heat, which can be measured with a thermographic image detector.

In another embodiment, an Abnormal Parathyroid Gland 30 can be detected when it has a rich blood supply and utilizes a greater proportionate oxygen, which can be measured with an O2 image detector.

In another embodiment, an Abnormal Parathyroid Gland 30 can be detected when it has a rich blood supply and with this produces and because of this produce an orange color greater than local tissue.

In another embodiment, an Abnormal Parathyroid Gland 30 can be detected when it has a rich blood supply and the greater blood flow and color Doppler flow signals than local tissue.

In another embodiment, an Abnormal Parathyroid Gland 30 has a lower echo texture than local tissue and can have a well-defined capsule and increased blood flow and this pattern can be used to identify the parathyroid during ablation and treatment of the parathyroid.

The methods of treatment can be used alone or in multiple combinations and can apply to multiple biological structures and tissue to include but not restricted to the parathyroid gland 30 and parathyroid tissue 30. In one example, a method of combination can include but is not restricted to the use of negative pressure/suction to alter the parathyroid's blood flow using a pressure device 75. In this example negative pressure is utilized which will alter the blood flow to the parathyroid gland 30. This will make the parathyroid tissue 30 more susceptible to cell damage or cell death. In this example, a second method of treatment can include but is not restricted to a cold laser delivery device 75. By combining the negative pressure to the parathyroid gland 30 and the cold laser to the parathyroid tissue 30 the time for effective ablation can be significantly reduced. This will spare the local tissue from any collateral damage that may be caused by the use of the cold laser.

The trachea lies adjacent to and posterior to the thyroid 20 and the two parathyroid glands 30. The Recurrent Laryngeal Nerve 13, which innervated the Larynx can be monitored or protected from the ablative energetic or non-energetic methods (not shown). Nerves can either be treated such as the parathyroid nerves 19 or protected such as the Recurrent Laryngeal Nerve 13.

In one embodiment a monitoring device 31 is used to protect afferent or efferent nerves 19 or structure innervated or in association with the nerve 19. The monitoring device 31 can be placed on or near a nerve 19, or on or near the structure 17 innervated or associated with the nerve 19. In one embodiment, the monitoring device 31 can be used but not restricted to parathyroid gland 30 and can involve but not restricted to monitoring of the recurrent laryngeal nerve 13 and the larynx 15. The monitoring device can measure but is not restricted to the measurement of either the parathyroid gland 30, local tissue environment or the nerve 19 or the structure associated with or innervated by the nerve or a combination of the above, and the monitoring can include but is not restricted to the monitoring of heat, cold, acid or base pH, electromagnetic energy or kinetic energy. The monitoring device 31 can automatically control the treatment delivery device 75 or can inform the user of the treatment delivery device 75 that an action needs to be taken to avoid damage to vital structures. The monitoring device 31 can be used to insure adequate treatment but also to avoid excessive damage to the structure or structures being monitored and can regulate the treatment delivery device 75.

In another embodiment the monitoring device 31 can be used to monitor the effectiveness of treatment of the target organ to include but not restricted to the parathyroid 30. The monitoring device can measure but is not restricted to the measurement of either the parathyroid gland 30, local tissue environment or the nerve 19 or the structure associated with or innervated by the nerve or a combination of the above, and the monitoring can include but is not restricted to the monitoring of heat, cold, acid or base pH, electromagnetic energy or kinetic energy. The monitoring device 31 can automatically control the treatment delivery device 75 or can inform the user of the treatment delivery device 75 that an action needs to be taken to avoid damage to vital structures. The monitoring device 31 can be used to insure adequate treatment but also to avoid excessive damage to the structure or structures being monitored and can regulate the treatment delivery device 75.

A method for localizing the parathyroid gland for a treatment to but not restricted to surgical removal of the target tissue to include but not restricted to parathyroid tissue 30. A needle/tube (52, 58, 70, 84), sheath 50, or device (75, 24) can be used to localize the site of the target organ to include but not restricted to the parathyroid gland 30.

In one embodiment, the method for localization can be using a radioactive tracer which can include but is not restricted to radioactive technetium Tc-99, or Iodine I-123, I-131. These isotopes can be used in the unbound or bound for to include but not restricted to technetium bound to a molecule to include but not restricted to Sestamibi and albumin, or it can be bound to a solid or gel that can include but not restricted to a biodegradable gel, surgical colloidal, a radioactive bead or clip or seed. The radioactivity can be placed within the body using a method that can reach the target organ to include but not restricted to the parathyroid 30 which can include but not restricted to percutaneous techniques, endoscopy, laparoscopy, catheterization and angiography. The radioactive isotope can be identified using a localizing device (5, 75, 80), to include but not restricted to a Geiger counter or radioactivity detecting probe which can direct therapy from or external to the skin to include but not restricted to SPECT-CT, PET-CT, SPECT-MRI, ultrasound, surgery, or within the body to include but not restricted to a percutaneous device 75 or a device that lies within the body by other means such as but not restricted to endoscopy, laparoscopy, catheterization and angiography. The localizing substance 99 can be implanted or left in position prior to, during or after the procedure. The localizing substance 99 can be used to guide external, internal or any combination of external and internal treatment modalities.

In another embodiment the localizing substance 99 can be a Global Positioning Satellite device, a Local Positioning Device (LPD) that can use a specialty built localizing device for the treatment room and can measure distances in measuring quantities less than 1 cm.

In another embodiment the localizing substance 99 can be an inert, organic, non-organic, biodegradable or non-biodegradable device.

In another embodiment the localizing substance 99 can be a device that can externally or internally be monitored to local the target organ that can include but is not restricted to a GPS device, an LPD, and RF localization device.

In another embodiment the localizing device can be a wire or thread-like substance that can be straight and pass through tissue to include but not restricted to the thyroid 20 or can be flexible and can be maneuvered around tissue to include but not restricted to the thyroid 20.

The localizing device and use any combination of localizing elements and methods.

A method for treating the target organ can include but not restricted to the parathyroid the method can deliver the treatment externally or internally to include but is not restricted to percutaneous laparoscopic methods or surgery.

Another method for treatment is to deliver an ablative substance to the target organ that can include but is not restricted to the parathyroid. The ablative substance or device can be inserted into the target preferentially by a needle percutaneously but also to include but not restricted to by laparoscope. The ablative substance or device can include but is not restricted to an RF receiver that can be implanted into the target organ to include but not restricted to the parathyroid.

In another method microscopic ferrous particles can be inserted into the parathyroid and the neck 3 and parathyroid 30 placed into an MRI device that can heat and mechanically ablated the parathyroid tissue 30.

A needle for percutaneously depositing the localizing substance 99, which in the preferred embodiment can include a radioactive biodegradable colloid with a titanium bead that measures less than 1 mm. The internal surface of the needle can include but is not restricted to threads. The stylet 57 which fits into the hollow needle 58 can have multiple shapes to include but not restricted to tips with points, blunt tips, matching treads or grooves with the needle in which the stylet can be screwed down into position. The stylet 57 and needle together can have a delimiter or governor 55 that limits that adjusts to seat the localizing substance 99 into position within the parathyroid gland 30.

Other embodiments of this needle can include grooves to include but are not restricted to horizontal or vertical grooves or threads or any combination of grooves that can be locked and unlocked into place to seat and deliver the localizing substance 99 into the target organ.

Another embodiment includes a membrane inside of the needle on one or both sides of the localizing substance 99, which can be pushed through the needle 58 and delivered to the target tissue to include but not restricted to the parathyroid tissue 30.

In another embodiment the localizing substance 99 can be deposited into the needle after the needle is secured to the target tissue 30 and one or more stylets 57 can be used.

A sheath can include but is not restricted to a tube or conduit or guide or guide and it can be hollow.

A member can include but is not restricted to a tube, cylinder, probe wire, guide wire, guide, device and it can be solid or hollow.

Controller can include but is not restricted to a device that takes an action in response to an input.

A measuring device can include but is not restricted to a sensor, or a device to measure a quality or quantity of a substance or energy or a phenomenon or a biological event.

Biological function can include but is not restricted parathyroid hormone activity, temperature, calcium levels, ionizing calcium, electrolytes, local temperature around parathyroid, neuronal function (laryngeal nerves), larynx and innervation, respiratory function, sympathetic and parasympathetic (primary and secondary) function, arterial flow, venal flow, brain function, cardiac functions, blood pressure, chromatography, and vital and hormonal and physiologic measurements, signs and symptoms.

A substance can include but is not restricted to solids or liquids or gels or plasmas or gases to include but not restricted to organic and inorganic materials such as but not restricted to medications, pharmaceuticals, adhesives, glues, metals, alloys, plastics, carbon-carbon fibers, oxygen, argon, nitrogen, carbon monoxide, ferromagnetic materials, alcohols, peptides, fats, proteins, nucleic acids, or carbohydrates.

Energy can refer to any form of energy, including various forms of electromagnetic energy, such as: radiofrequency (RF) energy; therapeutic ultrasound energy; microwave, laser, x-ray, or optical energy; magnetism, head and cryotherapy; or any combination thereof. Energy shall also refer to mechanical energy to include but not restricted to Brownian movement, heat, freezing, cryotherapy, cutting, tearing, crushing, spinning, piercing, poking prodding, dividing, removing and segregating or any combination thereof. Energy can include an energy from a device to include but not restricted to an Electromagnetic device (EMD) which can include but is not restricted to Radiofrequency ablation (RF) and microwave (MW) and laser (L), Cryotherapy (CryT), High Intensity Focused Ultrasound (HIFU), Radioactive Therapy (Brachytherapy: BrT), Irreversible Electroporation (IRE), Electrical Current Therapies, Electrocautery, Magnetic Resonance (MR), Ultrasound, (US), Thermal energies both heat and cold or can include but is not restricted to forces such but not restricted to suction, positive and negative pressure, or forces or not exerted by a vacuum.

Placement of the needle can include but is not restricted to placement by at least one organism with or without robotic assistance.

Treatment and Insulation and protection of the target and non-target vicinity tissue can include the delivery and the removal of energy and/or substances.

The energy delivered and the insulation experienced at any given moment during treatment by the user's target and non-target tissue can both vary and can be variable to include but not restricted to duration, direction, exposure, periodicity or frequency.

The following methods and devices and applications can be applied to Humans or Non-human.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

The invention claimed is:

1. A tightly targeted minimally invasive therapy (TTMIT) parathyroid tissue ablating instrument, comprising:

a substance that cytotoxically ablates parathyroidal tissue within a parathyroid gland of a living human during application in the parathyroidal tissue of therapeutically sufficient units of an electromagnetic energy having a frequency only ranging from ultraviolet to visible to near infrared;

wherein the substance is at least one of a non-mitochondrial cell component agent, a bio-activation agent, a bio-degradation agent, a chemical change agent, a methylation agent, a carboxylation, an acetylation agent, a de-methylation agent, a de-carboxylation agent, a carbon monoxide agent, a carbon dioxide agent, an antibody agent, an antibody analog agent, nanotechnology, an enzymatic agent, an enzymatic analog agent, a protein agent, a peptide agent, a peptide analog agent, a peptide modification agent, a parathyroid receptor agent, a parathyroid receptor analog agent, a partial parathyroid hormone receptor agent, a full parathyroid hormone receptor agent, cinacalcet, a cinacalcet analog agent, sestamibi, a sestamibi analog agent, a parathyroid hormone agent, a parathyroid precursor agent, an active portion of the parathyroid hormone agent, a partial portion of the parathyroid hormone agent, a full portion of the parathyroid hormone agent, a calcium agent, a calcium analog compound agent, an organic compound agent that can bind to parathyroid receptors, an inorganic compound agent that can bind to parathyroid receptors, an organic compound agent that can bind to parathyroid calcium receptors, and an inorganic compound agent that can bind to parathyroid calcium receptors;

a substance delivery device configured to introduce the substance into the parathyroidal tissue;

an electromagnetic energy treatment device configured to apply the therapeutically sufficient units of the electromagnetic energy within a thermal range that is non-cytotoxic to the parathyroidal tissue to the substance after the substance has been introduced by the substance delivery device into the parathyroidal tissue; and a sensor operationally coupled to the electromagnetic energy treatment device and the sensor configured to monitor activation of the substance for the electromagnetic energy treatment device as the therapeutically sufficient units of the electromagnetic energy are applied, the electromagnetic energy treatment device further configured to modulate applying the therapeutically sufficient units of the electromagnetic energy once the substance has been activated.

2. The TTMIT parathyroid tissue ablating instrument in accordance with claim 1, further comprising an agent that modifies at least one of the C-end of the peptide and the N component of the peptide.

3. The TTMIT parathyroid tissue ablating instrument in accordance with claim 1, further comprising:

the electromagnetic energy treatment device further configured to stop applying the electromagnetic energy once the substance has been activated.

4. The TTMIT parathyroid tissue ablating instrument in accordance with claim 1, further including at least one of:

a component comprised as part of the substance delivery device configured to be percutaneously introduced through the living human's skin and intervening tissue into the parathyroidal tissue and to deliver the substance into the parathyroidal tissue;

a component comprised as part of the substance delivery device configured to be intravascularly introduced via the living human's vascular channels into the parathyroidal tissue and to deliver the substance into the parathyroidal tissue;

a component comprised as part of the substance delivery device configured to transcutaneously introduce the substance into the parathyroidal tissue from outside the living human's body;

a component comprised as part of the substance delivery device configured to introduce the substance through an endoscopic instrument into the parathyroidal tissue; and a component comprised as part of the substance delivery device configured to introduce the substance through a surgically incised access into the parathyroidal tissue.

5. The TTMIT parathyroid tissue ablating instrument in accordance with claim 1, the substance further including one of:

a liquid within which the substance is dissolved;

a gel within which the substance is mixed;

a gas within which the substance is permeated;

one or more packets within which the substance is provided;

solid particles of the substance from which a safe amount of the substance is formed; and binding agents comprised with the substance.

6. A tightly targeted minimally invasive therapy (TTMIT) parathyroid tissue ablating instrument, comprising:

a substance that cytotoxically ablates parathyroidal tissue within a parathyroid gland of a living human during application in the parathyroidal tissue of therapeutically sufficient units of an electromagnetic energy having a frequency only ranging from ultraviolet to visible to near infrared;

a substance delivery device configured to introduce the substance into the parathyroidal tissue and to limit quantity and distribution of the substance being introduced;

wherein the substance is at least one of a non-mitochondrial cell component agent, a bio-activation agent, a bio-degradation agent, a chemical change agent, a methylation agent, a carboxylation, an acetylation agent, a de-methylation agent, a de-carboxylation agent, a carbon monoxide agent, a carbon dioxide agent, an antibody agent, an antibody analog agent, nanotechnology, an enzymatic agent, an enzymatic analog agent, a protein agent, a peptide agent, a peptide analog agent, a peptide modification agent, a parathyroid receptor agent, a parathyroid receptor analog agent, a partial parathyroid hormone receptor agent, a full parathyroid hormone receptor agent, cinacalcet, a cinacalcet analog agent, sestamibi, a sestamibi analog agent, a parathyroid hormone agent, a parathyroid precursor agent, an active portion of the parathyroid hormone agent, a partial portion of the parathyroid hormone agent, a full portion of the parathyroid hormone agent, a calcium agent, a calcium analog compound agent, an organic compound agent that can bind to parathyroid receptors, an inorganic compound agent that can bind to parathyroid receptors, an organic compound agent that can bind to parathyroid calcium receptors, and an inorganic compound agent that can bind to parathyroid calcium receptors;

an electromagnetic energy treatment device configured to apply the therapeutically sufficient units of the electromagnetic energy within a thermal range that is non-cytotoxic to the parathyroidal tissue to the substance after the substance has been introduced by the substance delivery device into the parathyroidal tissue; and a sensor operationally coupled to the electromagnetic energy treatment device and the sensor configured to monitor activation of the substance for the electromagnetic energy treatment device as the therapeutically sufficient units of the electromagnetic energy are applied, the electromagnetic energy treatment device further configured to modulate applying the therapeutically sufficient units of the electromagnetic energy once the substance has been activated.

7. The TTMIT parathyroid tissue ablating instrument in accordance with claim 6, further comprising an agent that modifies at least one of the C-end of the peptide and the N component of the peptide.

8. The TTMIT parathyroid tissue ablating instrument in accordance with claim 6, further comprising:

the electromagnetic energy treatment device further configured to stop applying the electromagnetic energy once the substance has been activated.

9. The TTMIT parathyroid tissue ablating instrument in accordance with claim 6, further including at least one of:

a component comprised as part of the substance delivery device configured to be percutaneously introduced through the living human's skin and intervening tissue into the parathyroidal tissue and to deliver the substance into the parathyroidal tissue;

a component comprised as part of the substance delivery device configured to be intravascularly introduced via the living human's vascular channels into the parathyroidal tissue and to deliver the substance into the parathyroidal tissue;

a component comprised as part of the substance delivery device configured to transcutaneously introduce the substance into the parathyroidal tissue from outside the living human's body;

a component comprised as part of the substance delivery device configured to introduce the substance through an endoscopic instrument into the parathyroidal tissue; and a component comprised as part of the substance delivery device configured to introduce the substance through a surgically incised access into the parathyroidal tissue.

10. The TTMIT parathyroid tissue ablating instrument in accordance with claim 6, the substance further including one of:

a liquid within which the substance is dissolved;

a gel within which the substance is mixed;

a gas within which the substance is permeated;

one or more packets within which the substance is provided;

solid particles of the substance from which a safe amount of the substance is formed; and binding agents comprised with the substance.

11. A tightly targeted minimally invasive therapy (TTMIT) parathyroid tissue ablating instrument, comprising:

an electromagnetic energy treatment device configured to apply therapeutically sufficient units of an electromagnetic energy having a frequency only ranging from ultraviolet to visible to near infrared into parathyroidal tissue of a parathyroid gland of a living human;

a substance that cytotoxically ablates parathyroidal tissue within the parathyroid gland during application in the parathyroidal tissue of the therapeutically sufficient units of the electromagnetic energy having a frequency only ranging from ultraviolet to visible to near infrared;

wherein the substance is at least one of a non-mitochondrial cell component agent, a bio-activation agent, a bio-degradation agent, a chemical change agent, a methylation agent, a carboxylation, an acetylation agent, a de-methylation agent, a de-carboxylation agent, a carbon monoxide agent, a carbon dioxide agent, an antibody agent, an antibody analog agent, nanotechnology, an enzymatic agent, an enzymatic analog agent, a protein agent, a peptide agent, a peptide analog agent, a peptide modification agent, a parathyroid receptor agent, a parathyroid receptor analog agent, a partial parathyroid hormone receptor agent, a full parathyroid hormone receptor agent, cinacalcet, a cinacalcet analog agent, sestamibi, a sestamibi analog agent, a parathyroid hormone agent, a parathyroid precursor agent, an active portion of the parathyroid hormone agent, a partial portion of the parathyroid hormone agent, a full portion of the parathyroid hormone agent, a calcium agent, a calcium analog compound agent, an organic compound agent that can bind to parathyroid receptors, an inorganic compound agent that can bind to parathyroid receptors, an organic compound agent that can bind to parathyroid calcium receptors, and an inorganic compound agent that can bind to parathyroid calcium receptors;

a substance delivery device configured to introduce the substance into the parathyroidal tissue; and a sensor operationally coupled to the substance delivery device and the sensor configured to monitor activation of the substance for the substance delivery device as the therapeutically sufficient units of the electromagnetic energy are applied, the substance delivery device further configured to limit the therapeutically sufficient units of the electromagnetic energy to a thermal range that is non-cytotoxic to the parathyroidal tissue and to control introducing the substance once the substance has been activated.

12. The TTMIT parathyroid tissue ablating instrument in accordance with claim 11, further comprising an agent that modifies at least one of the C-end of the peptide and the N component of the peptide.

13. The TTMIT parathyroid tissue ablating instrument in accordance with claim 11, further comprising:

the substance delivery device further configured to stop introducing the substance once the substance has been activated.

14. The TTMIT parathyroid tissue ablating instrument in accordance with claim 11, further including at least one of:

a component comprised as part of the substance delivery device configured to be percutaneously introduced through the living human's skin and intervening tissue into the parathyroidal tissue and to deliver the substance into the parathyroidal tissue;

a component comprised as part of the substance delivery device configured to be intravascularly introduced via the living human's vascular channels into the parathyroidal tissue and to deliver the substance into the parathyroidal tissue;

a component comprised as part of the substance delivery device configured to transcutaneously introduce the substance into the parathyroidal tissue from outside the living human's body;

a component comprised as part of the substance delivery device configured to introduce the substance through an endoscopic instrument into the parathyroidal tissue; and a component comprised as part of the substance delivery device configured to introduce the substance through a surgically incised access into the parathyroidal tissue.

15. The TTMIT parathyroid tissue ablating instrument in accordance with claim 11, the substance further including one of:

a liquid within which the substance is dissolved;

a gel within which the substance is mixed;

a gas within which the substance is permeated;

one or more packets within which the substance is provided;

solid particles of the substance from which a safe amount of the substance is formed; and binding agents comprised with the substance.

16. A tightly targeted minimally invasive therapy (TTMIT) parathyroid tissue ablating instrument, comprising:

an electromagnetic energy treatment device configured to apply therapeutically sufficient units of an electromagnetic energy having a frequency only ranging from ultraviolet to visible to near infrared into a targeted radius within parathyroidal tissue of a parathyroid gland of a living human;

a substance that cytotoxically ablates parathyroidal tissue within the parathyroid gland during application in the parathyroidal tissue of the therapeutically sufficient units of the electromagnetic energy having a frequency only ranging from ultraviolet to visible to near infrared;

wherein the substance is at least one of a non-mitochondrial cell component agent, a bio-activation agent, a bio-degradation agent, a chemical change agent, a methylation agent, a carboxylation, an acetylation agent, a de-methylation agent, a de-carboxylation agent, a carbon monoxide agent, a carbon dioxide agent, an antibody agent, an antibody analog agent, nanotechnology, an enzymatic agent, an enzymatic analog agent, a protein agent, a peptide agent, a peptide analog agent, a peptide modification agent, a parathyroid receptor agent, a parathyroid receptor analog agent, a partial parathyroid hormone receptor agent, a full parathyroid hormone receptor agent, cinacalcet, a cinacalcet analog agent, sestamibi, a sestamibi analog agent, a parathyroid hormone agent, a parathyroid precursor agent, an active portion of the parathyroid hormone agent, a partial portion of the parathyroid hormone agent, a full portion of the parathyroid hormone agent, a calcium agent, a calcium analog compound agent, an organic compound agent that can bind to parathyroid receptors, an inorganic compound agent that can bind to parathyroid receptors, an organic compound agent that can bind to parathyroid calcium receptors, and an inorganic compound agent that can bind to parathyroid calcium receptors;

a substance delivery device configured to introduce the substance into the parathyroidal tissue; and a sensor operationally coupled to the substance delivery device and the sensor configured to monitor activation of the substance for the substance delivery device as the therapeutically sufficient units of the electromagnetic energy are applied within the targeted radius, the substance delivery device further configured to limit the therapeutically sufficient units of the electromagnetic energy to a thermal range that is non-cytotoxic to the parathyroidal tissue and to control introducing the substance once the substance has been activated.

17. The TTMIT parathyroid tissue ablating instrument in accordance with claim 16, further comprising an agent that modifies at least one of the C-end of the peptide and the N component of the peptide.

18. The TTMIT parathyroid tissue ablating instrument in accordance with claim 16, further comprising:

the substance delivery device further configured to stop introducing the substance once the substance has been activated.

19. The TTMIT parathyroid tissue ablating instrument in accordance with claim 16, further including at least one of:

a component comprised as part of the substance delivery device configured to be percutaneously introduced through the living human's skin and intervening tissue into the parathyroidal tissue and to deliver the substance into the parathyroidal tissue;

a component comprised as part of the substance delivery device configured to be intravascularly introduced via the living human's vascular channels into the parathyroidal tissue and to deliver the substance into the parathyroidal tissue;

a component comprised as part of the substance delivery device configured to transcutaneously introduce the substance into the parathyroidal tissue from outside the living human's body;

a component comprised as part of the substance delivery device configured to introduce the substance through an endoscopic instrument into the parathyroidal tissue; and a component comprised as part of the substance delivery device configured to introduce the substance through a surgically incised access into the parathyroidal tissue.

20. The TTMIT parathyroid tissue ablating instrument in accordance with claim 16, the substance further including one of:

a liquid within which the substance is dissolved;

a gel within which the substance is mixed;

a gas within which the substance is permeated;

one or more packets within which the substance is pro-
  vided;

solid particles of the substance from which a safe amount
  of the substance is formed; and binding agents comprised with the substance.

\* \* \* \* \*